US010188661B2

(12) United States Patent
Singer et al.

(10) Patent No.: US 10,188,661 B2
(45) Date of Patent: Jan. 29, 2019

(54) TOPICAL DOSAGE REGIMEN

(71) Applicant: Topokine Therapeutics, Inc., Newton, MA (US)

(72) Inventors: Michael S. Singer, Newton Center, MA (US); Murat V. Kalayoglu, Silver Spring, MD (US)

(73) Assignee: Topokine Therapeutics, Inc., Parsippany, NJ (US)

( * ) Notice: Subject to any disclaimer, the term of this patent is extended or adjusted under 35 U.S.C. 154(b) by 0 days.

(21) Appl. No.: 15/321,241

(22) PCT Filed: Jun. 24, 2015

(86) PCT No.: PCT/US2015/037323
§ 371 (c)(1),
(2) Date: Dec. 22, 2016

(87) PCT Pub. No.: WO2015/200425
PCT Pub. Date: Dec. 30, 2015

(65) Prior Publication Data
US 2017/0202852 A1 Jul. 20, 2017

Related U.S. Application Data

(60) Provisional application No. 62/018,233, filed on Jun. 27, 2014.

(51) Int. Cl.
| A61K 31/5575 | (2006.01) |
| A61K 9/00 | (2006.01) |
| A61K 47/06 | (2006.01) |
| A61K 47/14 | (2017.01) |
| A61K 9/06 | (2006.01) |

(52) U.S. Cl.
CPC ........ *A61K 31/5575* (2013.01); *A61K 9/0014* (2013.01); *A61K 9/06* (2013.01); *A61K 47/06* (2013.01); *A61K 47/14* (2013.01)

(58) Field of Classification Search
CPC .................................................. A61K 31/5575
USPC .......................................................... 514/53
See application file for complete search history.

(56) References Cited

U.S. PATENT DOCUMENTS

| 4,270,537 A | 6/1981 | Romaine |
| 4,596,556 A | 6/1986 | Morrow et al. |
| 4,599,353 A | 7/1986 | Bito |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,011,062 A | 4/1991 | Nakanishi et al. |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,296,504 A | 3/1994 | Stjernschantz et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,422,368 A | 6/1995 | Stjernschantz et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,631,287 A | 5/1997 | Schneider |
| 5,649,912 A | 7/1997 | Peterson |
| 5,688,819 A | 11/1997 | Woodward et al. |
| 5,704,911 A | 1/1998 | Parsons |
| 5,849,792 A | 12/1998 | Schneider |
| 5,886,035 A | 3/1999 | Shirasawa et al. |
| 5,889,052 A | 3/1999 | Klimko et al. |
| 5,893,397 A | 4/1999 | Peterson et al. |
| 5,972,991 A | 10/1999 | Burk |
| 5,990,139 A | 11/1999 | Yano et al. |

(Continued)

FOREIGN PATENT DOCUMENTS

| CN | 101427993 A | 5/2009 |
| EA | 006556 B1 | 2/2006 |

(Continued)

OTHER PUBLICATIONS

International Preliminary Report on Patentability, dated Sep. 23, 2008, in connection with Application No. PCT/US2007/005424.
International Search Report and Written Opinion, dated Nov. 26, 2007, in connection with Application No. PCT/US2007/005424.
Invitation to Pay Additional Fees, dated Aug. 10, 2007, in connection with PCT/US2007/005424.
Extended European Search Report, dated Jul. 10, 2015, in connection with Application No. EP 12859422.3.
International Preliminary Report on Patentability, dated Jul. 3, 2014, in connection with Application for PCT/US2012/070581.
International Search Report and Written Opinion, dated May 30, 2013, in connection with Application No. PCT/US2012/070581.
International Search Report and Written Opinion, dated Sep. 29, 2014, in connection with Application No. PCT/US2014/038067.

(Continued)

Primary Examiner — Taofiq A Solola
(74) Attorney, Agent, or Firm — Wolf, Greenfield & Sacks, P.C.

(57) ABSTRACT

Described herein is a novel dosage regimen, and related uses and methods, for a prostaglandin FP receptor agonist (PFPRA) compound topically administered to the skin. The dosage regimen is useful for reduction of subcutaneous fat, for example, in patients who suffer from local excesses of subcutaneous fat. A particular advantage of the dosage regimen is the ability to reduce composition exposure and thereby promote convenience and comfort, while maintaining the desired exposure and therapeutic effect in subcutaneous fat. Further provided are kits according to the novel dosage regimen, comprising a PFPRA composition and instructions for use.

20 Claims, No Drawings

(56) References Cited

U.S. PATENT DOCUMENTS

| | | | |
|---|---|---|---|
| 5,993,412 | A | 11/1999 | Deily et al. |
| 6,232,344 | B1 | 5/2001 | Feng et al. |
| 6,235,781 | B1 | 5/2001 | Weiner et al. |
| 6,262,105 | B1 | 7/2001 | Johnstone |
| 6,403,649 | B1 | 6/2002 | Woodward et al. |
| 6,646,001 | B2 | 11/2003 | Hellberg et al. |
| 6,730,707 | B2 | 5/2004 | Pintor et al. |
| 6,864,282 | B2 | 3/2005 | Ling et al. |
| 6,911,474 | B2 | 6/2005 | Piomelli et al. |
| 6,933,289 | B2 | 8/2005 | Lyons et al. |
| 7,070,768 | B2 | 7/2006 | Krauss |
| 7,125,542 | B2 | 10/2006 | Miller et al. |
| 7,351,404 | B2 | 4/2008 | Woodward et al. |
| 7,622,130 | B2 | 11/2009 | Kolodney et al. |
| 7,666,912 | B2 | 2/2010 | Grosskreutz et al. |
| 8,273,362 | B2 | 9/2012 | Philips et al. |
| 8,367,606 | B2 | 2/2013 | Tennenbaum et al. |
| 8,426,471 | B1 | 4/2013 | Kalayoglu et al. |
| 8,569,376 | B2 | 10/2013 | Kalayoglu et al. |
| 8,722,097 | B2 | 5/2014 | Chang et al. |
| 8,778,981 | B2 | 7/2014 | Kalayoglu et al. |
| 8,829,050 | B2 | 9/2014 | Grosskreutz et al. |
| 8,841,345 | B2 | 9/2014 | Lu et al. |
| 8,877,807 | B2 | 11/2014 | Grosskreutz et al. |
| 9,040,584 | B2 | 5/2015 | Singer et al. |
| 9,089,579 | B2 | 7/2015 | Kalayoglu |
| 9,144,574 | B2 | 9/2015 | Grosskreutz |
| 9,180,130 | B2 | 11/2015 | Kalayoglu et al. |
| 9,421,215 | B2 | 8/2016 | Grosskreutz et al. |
| 9,504,695 | B2 | 11/2016 | Kalayoglu |
| 9,795,614 | B2 | 10/2017 | Grosskreutz et al. |
| 9,820,993 | B2 | 11/2017 | Singer |
| 9,849,179 | B2 | 12/2017 | Singer et al. |
| 9,861,641 | B2 | 1/2018 | Kalayoglu et al. |
| 2002/0172693 | A1 | 11/2002 | DeLong et al. |
| 2003/0181354 | A1 | 9/2003 | Abdulrazik |
| 2004/0023954 | A1 | 2/2004 | Ling et al. |
| 2004/0082660 | A1 | 4/2004 | Ueno |
| 2004/0115234 | A1 | 6/2004 | Gewirtz |
| 2004/0241245 | A1 | 12/2004 | Lu et al. |
| 2005/0058614 | A1 | 3/2005 | Krauss |
| 2005/0117830 | A1 | 6/2005 | Hartog et al. |
| 2005/0261373 | A1 | 11/2005 | Ueno |
| 2005/0261641 | A1 | 11/2005 | Warchol et al. |
| 2006/0246145 | A1 | 11/2006 | Chang et al. |
| 2007/0224246 | A1 | 9/2007 | Hughes et al. |
| 2007/0248658 | A1 | 10/2007 | Zurdo Schroeder et al. |
| 2008/0015257 | A1 | 1/2008 | Grosskreutz et al. |
| 2008/0107738 | A1 | 5/2008 | Philips et al. |
| 2008/0233053 | A1 | 9/2008 | Gross et al. |
| 2009/0042909 | A1 | 2/2009 | Karnik |
| 2010/0104654 | A1 | 4/2010 | Robinson et al. |
| 2010/0105771 | A1 | 4/2010 | deLong et al. |
| 2010/0234466 | A1 | 9/2010 | Grosskreutz et al. |
| 2010/0291226 | A1 | 11/2010 | Mazzone et al. |
| 2011/0124736 | A1 | 5/2011 | Trogden et al. |
| 2012/0046256 | A1 | 2/2012 | Dobak |
| 2012/0129789 | A1 | 5/2012 | Yoelin |
| 2012/0295972 | A1 | 11/2012 | Woodward et al. |
| 2013/0178525 | A1 | 7/2013 | Kalayoglu et al. |
| 2014/0045933 | A1 | 2/2014 | Kalayoglu |
| 2014/0163098 | A1 | 6/2014 | Grosskreutz et al. |
| 2014/0350104 | A1 | 11/2014 | Kalayoglu et al. |
| 2015/0025150 | A1 | 1/2015 | Kalayoglu |
| 2015/0025151 | A1 | 1/2015 | Grosskreutz et al. |
| 2015/0105462 | A1 | 4/2015 | Singer et al. |
| 2015/0164765 | A1 | 6/2015 | Yoelin |
| 2015/0231251 | A1 | 8/2015 | Singer et al. |
| 2015/0359801 | A1 | 12/2015 | Grosskreutz et al. |
| 2016/0051562 | A1 | 2/2016 | Kalayoglu et al. |
| 2016/0067263 | A1 | 3/2016 | Singer et al. |
| 2016/0354386 | A1 | 12/2016 | Grosskreutz et al. |
| 2017/0136032 | A1 | 5/2017 | Kalayoglu |

FOREIGN PATENT DOCUMENTS

| | | |
|---|---|---|
| EP | 302147 A1 | 2/1989 |
| EP | 1 864 666 A1 | 12/2007 |
| EP | 2 228 058 A1 | 9/2010 |
| EP | 3 124 015 A1 | 2/2017 |
| KR | 20140043562 A | 10/2014 |
| RU | 2157689 C2 | 10/2000 |
| RU | 2325912 C1 | 6/2008 |
| RU | 2009140073 A | 5/2011 |
| WO | WO 1997/013537 A1 | 4/1997 |
| WO | WO 1997/037705 A1 | 10/1997 |
| WO | WO 1999/034850 A1 | 7/1999 |
| WO | WO 2003/066008 A1 | 8/2003 |
| WO | WO 2005/034889 A2 | 4/2005 |
| WO | WO 2005/034890 A2 | 4/2005 |
| WO | WO 2006/048750 A2 | 5/2006 |
| WO | WO 2007/111806 A2 | 10/2007 |
| WO | WO 2010/039535 A1 | 4/2010 |
| WO | WO 2010/100217 A1 | 9/2010 |
| WO | WO 2011/057129 A2 | 5/2011 |
| WO | WO 2012/068515 A2 | 5/2012 |
| WO | WO 2012/099942 A2 | 7/2012 |
| WO | WO 2012/131734 A1 | 10/2012 |

OTHER PUBLICATIONS

International Preliminary Report on Patentability, dated Nov. 26, 2015, in connection with Application No. PCT/US2014/038067.

Extended European Search Report, dated Dec. 6, 2016, in connection with Application No. EP 16177742.0.

International Preliminary Report on Patentability, dated Nov. 19, 2015, in connection with Application No. PCT/US2014/037512.

International Search Report and Written Opinion, dated Dec. 4, 2014, in connection with Application No. PCT/US2014/037512.

Invitation to Pay Additional Fees, dated Aug. 21, 2014, in connection with Application No. PCT/US2014/037512.

Extended European Search Report, dated Jul. 8, 2014, in connection with Application No. EP 12736090.7.

Extended European Search Report, dated Dec. 21, 2015, in connection with Application No. EP 15180363.2.

International Preliminary Report on Patentability, dated Aug. 1, 2013, in connection with Application for PCT/US2012/021692.

International Search Report and Written Opinion, dated May 3, 2013, in connection with Application for PCT/US2012/021692.

Invitation to Pay Additional Fees, mailed Feb. 21, 2013, in connection with PCT/US2012/021692.

Second Written Opinion, dated Jun. 17, 2016, in connection with Application No. PCT/US2015/037323.

International Search Report and Written Opinion, dated Aug. 12, 2015, in connection with Application No. PCT/US2015/037323.

Initial Information Disclosure Statement for U.S. Appl. No. 11/712,839, filed May 19, 2008 (4 pages).

Email from Dr. Louis Pasquale to Lisa Putukian sent at 10:16 am, May 20, 2008, and forwarded to Daniel Wilson at 10:22 am, May 20, 2008, and related e-mail thread (3 pages).

E-mail from Dr. Michael Singer to Randall Morin sent at 1:57 pm, Jun. 4, 2008, and attached letter (8 pages) and Exhibits 1-10 from Dr. Singer to Mr. Morin dated Jun. 4, 2004.

Letter from Dr. Michael Singer to Lisa Putukian dated Sep. 22, 2008 (1 page—email correspondence attachment and MEEI Patent Policy and Procedures attachment omitted).

Letter from Dr. Michael Singer to Lisa Putukian dated Sep. 26, 2007 (3 pages and facsimile cover sheet).

Letter from Lisa Putukian to Dr. Michael Singer dated Sep. 22, 2008 (1 page.).

Letter from Lisa Putukian to Dr. Michael Singer dated Sep. 28, 2007 (2 pages), and attached Preliminary Amendment (3 pages).

[No Author Listed], Adrenal Disorders: Cushing Syndrome. Merck Manual Professional. Last revised Nov. 2007. Available at http://www.merck.com/mmpe/sec12/ch153/ch153e.html. Last visited Dec. 22, 2008.

[No Author Listed], Allergan Announces FDA Approval of LUMIGAN as First-Line Treatment for Elevated Eye Pressure in Open-Angle

(56) References Cited

OTHER PUBLICATIONS

Glaucoma; Indication Expands Approved Uses of LUMIGAN in the Management of Glaucoma. Business Wire. Jun. 23, 2006. Available at http://findarticles.com/p/articles/mi_m0EIN/is_2006June_23/ai_n26905641. Last visited Aug. 7, 2008. 2 pages.
[No Author Listed], Allergan Announces FDA Approval of Lumigan® as First-Line Treatment for Elevated Eye Pressure in Open-Angle Glaucoma; Indication Expands Approved Uses of Lumigan(R) in the Management of Glaucoma. Allergan Press Release. Jun. 23, 2006. Avaiable at http://agn360.client.shareholder.com/releasedetail.cfm?ReleaseID=201809. Last visited Sep. 9, 2008. 3 pages.
[No Author Listed], Chapter 42. Pharmacology of Eicosanoids. In: Principles of Pharmacology. The Pathophysiologic Basis of Drug Therapy. 3rd ed. Golan et al., eds. 2012: 743.
[No Author Listed], Definition of "prevent". WordNet Search 3.1. http://wordnet.princeton.edu [last accessed Sep. 18, 2012]. 1 page.
[No Author Listed], Dexamethasone Crystalline Product Information, Sigma Prod. No. D1756, dated Mar. 2001. 2 pages.
[No Author Listed], Excerpts from BodybuildingForYou—Bodybuilding Forums: Anabolic Steroids/Prohormones, and Testosterone Enhancers <http://www.bodybuildingforyou.com/forums/anabolic-steroids-prohormones-testosterone-enhancers/>/ Anabolic Steroids & Anabolic Chemistry & Testosterone Enhancers <http://www.bodybuildingforyou.com/forums/anabolic-steroids-anabolic-chemistry-testosterone-enhancers/>/ Anabolic Steroid, HGH, IGF, Insulin and Ancillary Profiles, pgf2a parts 3-5, post Nos. 35-37 by RRAdam on Jul. 12, 2005, http://www.bodybuildingforyou.com/forums/anabolic-steroids-anabolic-chemistry-testosterone-enhancers/22591-anabolic-steroid-hgh-igf-insulin-ancillary-profiles-2.html (14 pages).
[No Author Listed], Excerpts from Wanna Be Big Bodybuilding and Weightlifting Forums: Community Central <http://www.wannabebigforums.com/archive/index.php/f-20.html>/ General Chat <http://www.wannabebigforums.com/archive/index.php/f-12.html>/ The Myostatin Gene, posted at 4:22pm, Feb. 5, 2001, by Cackerot69, http://www.wannabebiciforums.com/archive/index.php/t-359.html (4 pages).
[No Author Listed], FDA CDER Approval Letter (3 pages) and Toxicology Study #5 from CDER Pharmacology Review (cover page and pp. 43-44 of 107 included) for Lumigan (Bimatoprost Ophthalmic Solution), NDA Application No. 21-275 (FDA Approval Date: Mar. 16, 2001), available at http://www.fda.gov/cder/foi/nda/2001/21275_Lumigan.htm (last visited May 23, 2008).
[No Author Listed], FDA CDER Toxicology Study #18 from CDER Pharmacology Review (cover page and pp. 67-69 of 107 included) for Lumigan (Bimatoprost Ophthalmic Solution), NDA Application No. 21-275 (FDA Approval Date: Mar. 16, 2001), available at http://www.fda.gov/cdergoi/nda/2001/21275_Lumigan.htm (last visited Dec. 22, 2008).
[No Author Listed], KEGG Database, Eicosanoids—Reference Pathway, available at http://www.genome.jp/kegg/pathway/map/map07034.html (last visited Jun. 10, 2008, 1 page).
[No Author Listed], Kegg Drug: D02724, [online] retrieved on Nov. 30, 2007, (2007), retrieved from http://www.genome.ad.jp/dbget-bin/www_bget?drug+D02724 and http://www.genome.ad.jp/dbget-bin/www_bget?pathway+map07035, printed p. 1 and printed pp. 1-3, respectively.
[No Author Listed], Latisse and Safety. Last accessed on Jul. 24, 2012 at http://www.latisseonline.com/latisse-safety/ 2 pages.
[No Author Listed], Material Safety Data Sheet for LUTALYSE® Sterile Solution, dated Jun. 23, 1997, available at httpIApfww.lutelysacomipahirnageslmsde...usiLutalvse.pdf (last visited Dec. 22, 2006).
[No Author Listed], Material Safety Data Sheet: Dimethyl Sulfoxide. OSHA-DOT. www.pattersonvet.com/msds/078406593 [last accessed Apr. 2, 2015]. 3 pages.
[No Author Listed], Ointments: Preparation and Evaluation of Drug Release. The Pharmaceutics and Compounding Laboratory. Mar. 4, 2013. http://pharmlabs.unc.edu/ointments/bases.htm. 2 pages.
[No Author Listed], Original New Animal Drug Application for ProstaMateTm (dinoprost tromethamine injection) Sterile Solution (ANADA No. 200-253). Dated Feb. 12, 1999. Available at http://www.fdagovlohrmsidockets/98fr1200253fi.pdf. Last visited Dec. 22, 2008.
[No Author Listed], Pfizer Inc., Citizen Petition to the Food and Drug Administration: Revoke Approval of Allergen's Supplemental NDA #21-257/S-013 for Lumigan (Bimatoprost Ophthalmic Solution 0.03%) and Deny Alcon's Supplemental NDA for Travatan (Travoprost Ophthalmic Solution 0.004%), Docket No. 2006P-0450, submitted on Nov. 1, 2006, available at http://www.fda.gov/ohrms/dockets/dockets/06p0450/06p-0450-cp00001-toc.htm.
[No Author Listed], Prescribing Information for SAFLUTAN® 15 micrograms/ml eye drops, solution, single-dose container (tafluprost), dated Aug. 2009.
[No Author Listed], Product label of DECADRON® dexamethasone tablets, label for May 17, 2004 approval (NDA No. 011664), available at http://dailymed.nlm.nih.gov/dailvmed/druuInfo.cfm?id=2934 (last visitedDec. 22, 2008).
[No Author Listed], Product Label of LUMIGAN (bimatoprost ophthalmic solution) 0.03%, label for Jun. 22, 2006 approval of new or modified indication, available at http://www.fda.gov/cder/foi/label/2006/021275s013Ibl.pdf (last visited Sep. 9, 2008).
[No Author Listed], Product Label of TRAVATAN® (travoprost ophthalmic solution) 0.004%, label for Feb. 13, 2003 approval of efficacy supplement with clinical data to support, available at http://www.fda.gov/cder/foUlabe1/2003/021257s0061bl.pdf (last visited Sep. 9, 2008).
[No Author Listed], Product Label of Xalatan® (latanoprost ophthalmic solution), label for Dec. 20, 2002 approval of new or modified indication, available at http://www.fda.gov/cder/foi/label/2002/20597SE1-010_Xalatan_lbl.pdf (last visited Sep. 9, 2008).
[No Author Listed], Prostaglandin analogues. Entrepreneur.com. 2008. Available at http://www.entrepreneur.com/tradejournals/article/print/166777491.html. 2 pages.
[No Author Listed], The American Heritage® Dictionary of the English Language, Fourth Edition, 2000, p. 1701 (with the definition of "steroid").
[No Author Listed], TRAVATAN™ (travoprost ophthalmic solution) 0.004% Sterile. NDA 21-257. Alcon Laboratories Inc. 2001. 7 pages.
Aihara et al., Incidence of deepening of the upper eyelid sulcus after switching from latanoprost to bimatoprost. Jpn J Ophthalmol. Nov. 2011;55(6):600-4. Epub Sep. 28, 2011.
American Diabetes Association, Diagnosis and Classification of Diabetes Mellitus. Diabetes Care. Jan. 2004;27(1):S5-10.
American Diabetes Association, Standards of Medical Care in Diabetes—2008. Diabetes Care. Jan. 2008;31(1):S12-54.
Anderson et al., High-carbohydrate, high-fiber diets for insulin-treated men with diabetes mellitus. Am J Clin Nutr. Nov. 1979;32(11):2312-21.
Asano et al., The PI 3-kinase/Akt signaling pathway is activated due to aberrant Pten expression and targets transcription factors NF-kappaB and c-Myc in pancreatic cancer cells. Oncogene. Nov. 11, 2004;23(53):8571-80. Erratum in: Oncogene. Jun. 16, 2005;24(26)4320.
Atkins et al., Randomized phase II study of multiple dose levels of CCI-779, a novel mammalian target of rapamycin kinase inhibitor, in patients with advanced refractory renal cell carcinoma. J Clin Oncol. Mar. 1, 2004;22(5):909-18.
Aydin et al., Recovery of orbital fat pad prolapsus and deepening of the lid sulcus from topical bimatoprost therapy: 2 case reports and review of the literature. Cutan Ocul Toxicol. Sep. 2010;29(3):212-6.
Baer et al., Measurement of body composition of live rats by electromagnetic conductance. Physiol Behav. Jun. 1993;53(6):1195-9.
Bai et al., Nucleophosmin-anaplastic lymphoma kinase associated with anaplastic large-cell lymphoma activates the phosphatidylinositol 3-kinase/Akt antiapoptotic signaling pathway. Blood. Dec. 15, 2000;96(13):4319-27.
Berenson et al., Changes in weight, total fat, percent body fat, and central-to-peripheral fat ratio associated with injectable and oral contraceptive use. Am J Obstet Gynecol. Mar. 2009;200(3):329.e1-8.

(56) References Cited

OTHER PUBLICATIONS

Berge et al., Pharmaceutical salts. J Pharm Sci. Jan. 1977;66(1):1-19.
Bertin et al., Evaluation of dual-energy X-Ray absorptiometry for body-composition assessment in rats. J Nutr. Sep. 1998;128(9):1550-4.
Billottet et al., A selective inhibitor of the p110delta isoform of PI 3-kinase inhibits AML cell proliferation and survival and increases the cytotoxic effects of VP16. Oncogene. Oct. 26, 2006;25(50):6648-59. Epub May 15, 2006.
Bissler et al., Sirolimus for angiomyolipoma in tuberous sclerosis complex or lymphangioleiomyomatosis. N Engl J Med. Jan. 10, 2008;358(2):140-51.
Blank et al., Mechanism of percutaneous absorption. 3. The effect of temperature on the transport of non-electrolytes across the skin. J Invest Dermatol. Dec. 1967;49(6):582-9.
Bos, ras oncogenes in human cancer: a review. Cancer Res. Sep. 1, 1989;49(17):4682-9.
Bowker et al., Increased cancer-related mortality for patients with type 2 diabetes who use sulfonylureas or insulin. Diabetes Care. Feb. 2006;29(2):254-8.
Byun et al., Frequent monoallelic deletion of PTEN and its reciprocal associatioin with PIK3CA amplification in gastric carcinoma. Int J Cancer. Apr. 10, 2003;104(3):318-27.
Cairns et al., Frequent inactivation of PTEN/MMAC1 in primary prostate cancer. Cancer Res. Nov. 15, 1997;57(22):4997-5000.
Cao et al., Addiction to elevated insulin-like growth factor I receptor and initial modulation of the AKT pathway define the responsiveness of rhabdomyosarcoma to the targeting antibody. Cancer Res. Oct. 1, 2008;68(19):8039-48.
Casimir et al., Preadipocyte differentiation blocked by prostaglandin stimulation of prostanoid FP2 receptor in murine 3T3-L1 cells. Differentiation. Jul. 1996;60(4):203-10.
Casimir, Regulation of early preadipocyte differentiation: cAMP and prostaglandin F-2-alpha. ProQuest Dissertations and Theses; 1996; ProQuest Dissertations & Theses (PQDT). UMI No. 9634889. 162 pages.
Chapman et al., Glucocorticoid regulation of adipocyte differentiation: hormonal triggering of the developmental program and induction of a differentiation-dependent gene. J Cell Biol. Oct. 1985;101(4):1227-35.
Chen et al., Simultaneous determination and pharmacokinetic study of metformin and rosiglitazone in human plasma by HPLC-ESI-MS. J Chromatogr Sci. Feb. 2011;49(2):94-100.
Choi et al., In vitro study of antiadipogenic profile of latanoprost, travoprost, bimatoprost, and tafluprost in human orbital preadiopocytes. J Ocul Pharmacol Ther. Apr. 2012;28(2):146-52. Epub. Nov. 22, 2011. E-pub version.
Chun et al., Effects of deguelin on the phosphatidylinositol 3-kinase/Akt pathway and apoptosis in premalignant human bronchial epithelial cells. J Natl Cancer Inst. Feb. 19, 2003;95(4):291-302.
Culebras et al., Total Body Water and the Exchangeable Hydrogen. II. Total body water and the exchangeable hydrogen. II. A review of comparative data from animals based on isotope dilution and desiccation, with a report of new data from the rat. Am J Physiol. Jan. 1977;232(1):R60-5.
Dahms et al., Correlation of percent body fat with body specific gravity in rats. J Nutr. Feb. 1982;112(2):398-400.
Dal Col et al., Distinct functional significance of Akt and mTOR constitutive activation in mantle cell lymphoma. Blood. May 15, 2008;111(10):5142-51. Epub Mar. 13, 2008.
Damodharan et al., Skin Permeation of Rosiglitazone from Transdermal Matrix Patches. Pharmaceutical Technology. 2010;34(5):56-72.
Database WPI, Week 201434. Thomson Scientific, London, GB; AN 2014-G76718 XP002729483 & KR 2014 0043562. Apr. 10, 2014. 3 pages.
Davidson et al., Weight control and risk factor reduction in obese subjects treated for 2 years with orlistat: a randomized controlled trial. JAMA. Jan. 20, 1999;281(3):235-42. Erratum in: JAMA Apr. 7, 1999;281(13):1174.
Dayan et al., Delivery System Design in Topically Applied Formulations: An Overview. In: Delivery System Handbook for Personal Care and Cosmetic Products. Rosen, ed. William Andrew. 2005:103-104.
Ettmayer et al., Lessons learned from marketed and investigational prodrugs. J Med Chem. May 6, 2004;47(10):2393-404.
Evans et al., Metformin and reduced risk of cancer in diabetic patients. BMJ. Jun. 4, 2005;330(7503):1304-5. Epub Apr. 22, 2005.
Fay et al., Energy homeostasis and cancer prevention: the AMP-activated protein kinase. Cancer Prev Res (Phila). Apr. 2009;2(4):301-9. Epub Mar. 31, 2009.
Ferner, Neurofibromatosis 1. Eur J Hum Genet. Feb. 2007;15(2):131-8. Epub Sep. 6, 2006.
Filippopoulos et al., Periorbital changes associated with topical bimatoprost. Ophthal Plast Reconstr Surg. Jul.-Aug. 2008;24(4):302-7.
Fletcher et al., Fibrinogen catabolism in patients with type II and type IV hyperlipidemia. Effect of dietary and clofibrate treatment on laboratory findings. Arteriosclerosis. May-Jun. 1981;1(3):202-9.
Fricke et al., The PGF(2alpha) receptor FP is lost in nevi and melanoma. Pigment Cell Melanoma Res. Feb. 2010;23(1):141-3. Epub Dec. 11, 2009.
Frisch et al., Carcass components at first estrus of rats on high-fat and low-fat diets: body water, protein, and fat. Proc Natl Acad Sci U S A. Jan. 1977;74(1):379-83.
Gaidhu et al., Chronic AMP-kinase activation with AICAR reduces adiposity by remodeling adipocyte metabolism and increasing leptin sensitivity. J Lipid Res. Sep. 2011;52(9):1702-11. Epub Jul. 7, 2011.
Gandelman et al., An eight-week trial investigating the efficacy and tolerability of atorvastatin for children and adolescents with heterozygous familial hypercholesterolemia. Pediatr Cardiol. Apr. 2011;32(4):433-41. Epub Jan. 23, 2011.
García-Rostán et al., Mutation of the PIK3CA gene in anaplastic thyroid cancer. Cancer Res. Nov. 15, 2005;65(22):10199-207.
Ghany et al., Diagnosis, management, and treatment of hepatitis C: an update. Hepatology. Apr. 2009;49(4):1335-74.
Ghosh et al., Feasibility of rosiglitazone maleate for transdermal delivery. Int J Pharma Res Innov. 2011;2:23-31.
Goel et al., Examination of mutations in BRAF, NRAS, and PTEN in primary cutaneous melanoma. J Invest Dermatol. Jan. 2006;126(1):154-60.
Goel et al., Frequent inactivation of PTEN by promoter hypermethylation in microsatellite instability-high sporadic colorectal cancers. Cancer Res. May 1, 2004;64(9):3014-21.
Gorin et al., Evidence for a role of protein kinase C in the stimulation of lipolysis by growth hormone and isoproterenol. Endocrinology. Jun. 1990;126(6):2973-82.
Gray et al., Mutation and expression analysis of the putative prostate tumour-suppressor gene PTEN. Br J Cancer. Nov. 1998;78(10):1296-300.
Gregersen et al., Genetics of autoimmune diseases—disorders of immune homeostasis. Nature Rev Gen. Dec. 2006;7:917-28.
Gregoire et al., Understanding adipocyte differentiation. Physiol Rev. Jul. 1998;78(3):783-809.
Grosskreutz et al., Periorbital Fat Loss and Eyelid Sulcus Deepening after Bimatoprost Therapy. Final Program and Abstract Book, pp. 49 and 53, distributed at the American Glaucoma Society 2006 Annual Meeting, Mar. 2-5, 2006.
Grosskreutz et al., Periorbital Fat Loss and Eyelid Sulcus Deepening after Bimatoprost Therapy. Poster presented at The American Glaucoma Society 2006 Annual Meeting, Charleston, South Carolina. Mar. 2-5, 2006. 1 page.
Grosskreutz, Abstract submitted on Nov. 1, 2005 to the American Glaucoma Society for the American Glaucoma Society 2006 Annual Meeting. 1 page.
Guldberg et al., Disruption of the MMAC1/PTEN gene by deletion or mutation is a frequent event in malignant melanoma. Cancer Res. Sep. 1, 1997;57(17):3660-3.

(56) References Cited

OTHER PUBLICATIONS

Guo et al., The AMPK agonist AICAR inhibits the growth of EGFRvIII-expressing glioblastomas by inhibiting lipogenesis. Proc Natl Acad Sci U S A. Aug. 4, 2009;106(31):12932-7. Epub Jul. 22, 2009.

Gupta et al., Local recurrence in head and neck cancer: relationship to radiation resistance and signal transduction. Clin Cancer Res. Mar. 2002;8(3):885-92.

Gwinn et al., AMPK phosphorylation of raptor mediates a metabolic checkpoint. Mol Cell. Apr. 25, 2008;30(2):214-26.

Hardie, AMP-activated protein kinase: an energy sensor that regulates all aspects of cell function. Genes Dev. Sep. 15, 2011;25(18):1895-908. doi: 10.1101/gad.17420111.

Hata et al., Pharmacology and signaling of prostaglandin receptors: multiple roles in inflammation and immune modulation. Pharmacol Ther. Aug. 2004;103(2):147-66.

Heim, Transdermal Administration of Anti-inflammatory Medications in Sports Injuries: Use of Iontophoresis and Phonophoresis to Enhance Delivery. Int J Pharm Compd. Jan.-Feb. 2006;10(1):14-18.

Hellberg et al., The hydrolysis of the prostaglandin analog prodrug bimatoprost to 17-phenyl-trinor PGF2alpha by human and rabbit ocular tissue. J Ocul Pharmacol Ther. Apr. 2003;19(2):97-103.

Hickey et al., BCR-ABL regulates phosphatidylinositol 3-kinase-p110gamma transcription and activation and is required for proliferation and drug resistance. J Biol Chem. Feb. 3, 2006;281(5):2441-50. Epub Nov. 16, 2005.

Holmstrom et al., Analytic review of bimatoprost, latanoprost and travoprost in primary open angle glaucoma. Curr Med Res Opin. Nov. 2005;21(11):1875-83.

Hu et al., Expression and prognostic role of tumor suppressor gene PTEN/MMAC1/TEP1 in hepatocellular carcinoma. Cancer. Apr. 15, 2003;97(8):1929-40.

Husain et al., Acute effects of PGF2alpha on MMP-2 secretion from human ciliary muscle cells: a PKC- and ERK-dependent process. Invest Ophthalmol Vis Sci. May 2005;46(5):1706-13.

Ichhpujani et al., Comparison of human ocular distribution of bimatoprost and latanoprost. J Ocul Pharmacol Ther. Apr. 2012;28(2):134-45. doi: 10.1089/jop.2011.0097. Epub Dec. 2, 2011.

Inoue et al., Deepening of the Upper Eyelid Sulcus Caused by 5 Types of Prostaglandin Analogs. J Glaucoma. Aug. 29, 2012. [Epub ahead of print] E-pub version. 6 pages.

Izumi et al., Short-term effects of topical tafluprost on retinal blood flow in cats. J Ocul Pharmacol Ther. Oct. 2008;24(5):521-6. doi: 10.1089/jop.2007.0065.

Jabbour et al., A positive feedback loop that regulates cyclooxygenase-2 expression and prostaglandin F2alpha synthesis via the F-series-prostanoid receptor and extracellular signal-regulated kinase 1/2 signaling pathway. Endocrinology. Nov. 2005;146(11):4657-64. Epub Aug. 4, 2005.

Jacob et al., Weight gain in type 2 diabetes mellitus. Diabetes Obes Metab. May 2007;9(3):386-93.

Johannessen et al., TORC1 is essential for NF1-associated malignancies. Curr Biol. Jan. 8, 2008;18(1):56-62. Epub Dec. 27, 2007.

Jonas et al., Drug Class Review: Newer diabetes medications, TZDs, and combinations. Final Original Report. Drug Effectiveness Review Project. Feb. 2011.

Kao, In Vitro Assessment of Dermal Absorption. In: Dermal and Ocular Toxicology: Fundamentals and Methods. Hobson, ed. CRC Press. 1991:267, 272-273.

Karlsson et al., cDNA cloning, tissue distribution, and identification of the catalytic triad of monoglyceride lipase. Evolutionary relationship to esterases, lysophospholipases, and haloperoxidases. J Biol Chem. Oct. 24, 1997;272(43):27218-23.

Kayikcioglu et al., Semicircular lipoatrophy after intragluteal injection of benzathine penicillin. J Pediatr. Jul. 1996;129(1):166-7.

Kim et al., The increase in abdominal subcutaneous fat depot is an independent factor to determine the glycemic control after rosiglitazone treatment. Eur J Endocrinol. Aug. 2007;157(2):167-74.

Kisfalvi et al., Metformin disrupts crosstalk between G protein-coupled receptor and insulin receptor signaling systems and inhibits pancreatic cancer growth. Cancer Res. Aug. 15, 2009;69(16):6539-45.

Klein et al., Absence of an effect of liposuction on insulin action and risk factors for coronary heart disease. N Engl J Med. Jun. 17, 2004;350(25):2549-57.

Klein et al., Non-invasive cryolipolysis for subcutaneous fat reduction does not affect serum lipid levels or liver function tests. Lasers Surg Med. Dec. 2009;41(10):785-90.

Kokubo et al., Reduction of PTEN protein and loss of epidermal growth factor receptor gene mutation in lung cancer with natural resistance to gefitinib (IRESSA). Br J Cancer. May 9, 2005;92(9):1711-9.

Kudchodkar et al., AMPK-mediated inhibition of mTOR kinase is circumvented during immediate-early times of human cytomegalovirus infection. J Virol. Apr. 2007;81(7):3649-51. Epub Jan. 10, 2007.

Kuenzli et al., Effect of topical PPARbeta/delta and PPARgamma agonists on plaque psoriasis. A pilot study. Dermatology. 2003;206(3):252-6.

Kumar et al., Lecithin organogels as a potential phospholipid-structured system for topical drug delivery: a review. AAPS PharmSciTech. Oct. 6, 2005;6(2):E298-310.

Künnecke et al., Quantitative body composition analysis in awake mice and rats by magnetic resonance relaxometry. Obes Res. Oct. 2004;12(10):1604-15.

Lee et al., Chemopreventive effects of deguelin, a novel Akt inhibitor, on tobacco-induced lung tumorigenesis. J Natl Cancer Inst. Nov. 16, 2005;97(22):1695-9.

Lee et al., PIK3CA gene is frequently mutated in breast carcinomas and hepatocellular carcinomas. Oncogene. Feb. 17, 2005;24(8):1477-80.

Lepak et al., Inhibition of adipose differentiation by 9 alpha, 11 beta-prostaglandin F2 alpha. Prostaglandins. Dec. 1993;46(6):511-7.

Lepak et al., Prostaglandin F2 alpha stimulates transforming growth factor-alpha expression in adipocyte precursors. Endocrinology. Aug. 1995;136(8):3222-9.

Lesser et al., Modification of subcutaneous adipose tissue by a methylxanthine formulation: a double-blind controlled study. Dermatol Surg. Jun. 1999;25(6):455-62.

Lin et al., Green tea polyphenol epigallocatechin gallate inhibits adipogenesis and induces apoptosis in 3T3-L1 adipocytes. Obes Res. Jun. 2005;13(6):982-90.

Liszka et al., Effect of lipectomy on growth and development of hyperinsulinemia and hyperlipidemia in the Zucker rat. Plast Reconstr Surg. Sep. 1998;102(4):1122-7.

Liu et al., Postaglandin F2alpha inhibits adipocyte differentiation via a G alpha q-calcium-calcineurin-dependent signaling pathway. J Cell Biochem. Jan. 1, 2007;100(1):161-73.

Löffler et al., Adipose tissue development: the role of precursor cells and adipogenic factors. Part II: The regulation of the adipogenic conversion by hormones and serum factors. Klin Wochenschr. Sep. 1, 1987;65(17):812-7.

Lu et al., Loss of tuberous sclerosis complex-2 function and activation of mammalian target of rapamycin signaling in endometrial carcinoma. Clin Cancer Res. May 1, 2008;14(9):2543-50.

Lu et al., PI3K-Akt signaling is involved in the regulation of p21(WAF/CIP) expression and androgen-independent growth in prostate cancer cells. Int J Oncol. Jan. 2006;28(1):245-51.

Majumder et al., Akt-regulated pathways in prostate cancer. Oncogene. Nov. 14, 2005;24(50):7465-74.

Massion et al., Early involvement of the phosphatidylinositol 3-kinase/Akt pathway in lung cancer progression. Am J Respir Crit Care Med. Nov. 15, 2004;170(10):1088-94. Epub Aug. 18, 2004.

Maxey et al., The hydrolysis of bimatoprost in corneal tissue generates a potent prostanoid FP receptor agonist. Surv Ophthalmol. Aug. 2002;47 Suppl 1:S34-40.

Miller et al., The mechanism of inhibition of 3T3-L1 preadipocyte differentiation by prostaglandin F2alpha. Endocrinology. Dec. 1996;137(12):5641-50.

(56) References Cited

OTHER PUBLICATIONS

Mohammed et al., Long-term effects of large-volume liposuction on metabolic risk factors for coronary heart disease. Obesity (Silver Spring). Dec. 2008;16(12):2648-51. doi: 10.1038/oby.2008.418. Epub Jun. 1, 2009. 8 pages.

Morissette et al., High-throughput crystallization: polymorphs, salts, co-crystals and solvates of pharmaceutical solids. Adv Drug Deliv Rev. Feb. 23, 2004;56(3):275-300.

Morley, Orexigenic and anabolic agents. Clin Geriatr Med. Nov. 2002;18(4):853-66. Review.

Motzer et al., Phase I/II trial of temsirolimus combined with interferon alfa for advanced renal cell carcinoma. J Clin Oncol. Sep. 1, 2007;25(25):3958-64.

Mulholland et al., PTEN and GSK3beta: key regulators of progression to androgen-independent prostate cancer. Oncogene. Jan. 19, 2006;25(3):329-37.

Nafz et al., Interference with energy metabolism by 5-aminoimidazole-4-carboxamide-1-beta-D-ribofuranoside induces HPV suppression in cervical carcinoma cells and apoptosis in the absence of LKB1. Biochem J. May 1, 2007;403(3):501-10.

Nagata et al., PTEN activation contributes to tumor inhibition by trastuzumab, and loss of PTEN predicts trastuzumab resistance in patients. Cancer Cell. Aug. 2004;6(2):117-27.

Nahta et al., Mechanisms of disease: understanding resistance to HER2-targeted therapy in human breast cancer. Nat Clin Pract Oncol. May 2006;3(5):269-80.

Nakajima et al., New fluoroprostaglandin F(2alpha) derivatives with prostanoid FP-receptor agonistic activity as potent ocular-hypotensive agents. Biol Pharm Bull. Dec. 2003;26(12):1691-5.

Nakakura et al., Latanoprost therapy after sunken eyes caused by travoprost or bimatoprost. Optom Vis Sci. Sep. 2011;88(9):1140-4.

Nassif et al., PTEN mutations are common in sporadic microsatellite stable colorectal cancer. Oncogene. Jan. 15, 2004;23(2):617-28.

Nozue et al., Effects of statin on small dense low-density lipoprotein cholesterol and remnant-like particle cholesterol in heterozygous familial hypercholesterolemia. J Atheroscler Thromb. Jun. 2008;15(3):146-53.

Obata et al., Frequent PTEN/MMAC mutations in endometrioid but not serous or mucinous epithelial ovarian tumors. Cancer Res. May 15, 1998;58(10):2095-7.

Ota et al., The IOP-lowering effects and mechanism of action of tafluprost in prostanoid receptor-deficient mice. Br J Ophthalmol. May 2007;91(5):673-6. Epub Nov. 23, 2006.

Pantoja et al., Glucocorticoid signaling defines a novel commitment state during adipogenesis in vitro. Mol Biol Cell. Oct. 2008;19(10):4032-41. Epub Jul. 23, 2008.

Pao et al., KRAS mutations and primary resistance of lung adenocarcinomas to gefitinib or erlotinib. PLoS Med. Jan. 2005;2(1):e17. Epub Jan. 25, 2005.

Park et al., Changes to upper eyelid orbital fat from use of topical bimatoprost, travoprost, and latanoprost. Jpn J Ophthalmol. Jan. 2011;55(1):22-7. Epub Feb. 18, 2011.

Park et al., In vitro skin penetration and pharmacodynamic evaluation of prostaglandin E1 ethyl ester, a vasoactive prodrug of prostaglandin E1, formulated into alcoholic hydrogels. Pharmazie. Nov. 2006;61(11):933-7.

Paula et al., Periorbital Fat Loss and Eyelid Sulcus Deepening after Bimatoprost Therapy. Manuscript submitted to Archives of Ophthalmology, Oct. 21, 2005 (10 pages).

Peplinski et al., Deepening of lid sulcus from topical bimatoprost therapy. Optom Vis Sci. Aug. 2004;81(8):574-7.

Porter et al., Abdominal subcutaneous adipose tissue: a protective fat depot? Diabetes Care. Jun. 2009;32(6):1068-75. doi: 10.2337/dc08-2280. Epub Feb. 24, 2009.

Rattan et al., 5-Aminoimidazole-4-carboxamide-1-beta-D-ribofuranoside inhibits cancer cell proliferation in vitro and in vivo via AMP-activated protein kinase. J Biol Chem. Nov. 25, 2005;280(47):39582-93. Epub Sep. 21, 2005.

Reginato et al., Prostaglandins promote and block adipogenesis through opposing effects on peroxisome proliferator-activated receptor gamma. J Biol Chem. Jan. 23, 1998;273(4):1855-8.

Robin, An accurate comparison of bimatoprost's efficacy and adverse effects. Arch Ophthalmol. Jul. 2002;120(7):999-1000; author reply 1000.

Ross, Does exercise without weight loss improve insulin sensitivity? Diabetes Care. Mar. 2003;26(3):944-5.

Rundle, Drug That Lengthens Eyelashes Sets Off Flutter. Wall Street J. Nov. 19, 2007 (2 pages).

Sales et al., Expression, localization, and signaling of prostaglandin F2 alpha receptor in human endometrial adenocarcinoma: regulation of proliferation by activation of the epidermal growth factor receptor and mitogen-activated protein kinase signaling pathways. J Clin Endocrinol Metab. Feb. 2004;89(2):986-93.

Sales et al., F-prostanoid receptor regulation of fibroblast growth factor 2 signaling in endometrial adenocarcinoma cells. Endocrinology. Aug. 2007;148(8):3635-44. Epub May 3, 2007.

Schiwek et al., Glucocorticoid hormones contribute to the adipogenic activity of human serum. Endocrinology. Feb. 1987;120(2):469-74. Abstract only.

Selliah et al., AL-12182, a novel 11-oxa prostaglandin analog with topical ocular hypotensive activity in the monkey. Bioorg Med Chem Lett. Sep. 6, 2004;14(17):4525-8.

Serrero et al., Prostaglandin F2 alpha inhibits epidermal growth factor binding to cellular receptors on adipocyte precursors in primary culture. Biochem Biophys Res Commun. Jul. 26, 1995;212(3):1125-32.

Serrero et al., Prostaglandin F2 alpha inhibits the differentiation of adipocyte precursors in primary culture. Biochem Biophys Res Commun. Mar. 16, 1992;183(2):438-42.

Serrero et al., Prostaglandin F2alpha receptor (FP receptor) agonists are potent adipose differentiation inhibitors for primary culture of adipocyte precursors in defined medium. Biochem Biophys Res Commun. Apr. 7, 1997;233(1):200-2.

Shah et al., A cross-sectional survey of the association between bilateral topical prostaglandin analogue use and ocular adnexal features. PLoS One. May 1, 2013;8(5):e61638. doi: 10.1371/journal.pone.0061638. Print 2013.7 pages.

Sharif et al., Agonist activity of bimatoprost, travoprost, latanoprost, unoprostone isopropyl ester and other prostaglandin analogs at the cloned human ciliary body FP prostaglandin receptor. J Ocul Pharmacol Ther. Aug. 2002;18(4):313-24.

Shi et al., A glucocorticoid-induced leucine-zipper protein, GILZ, inhibits adipogenesis of mesenchymal cells. EMBO Rep. Apr. 2003;4(4):374-80. Epub Mar. 14, 2003.

Shugart et al., Dexamethasone signaling is required to establish the postmitotic state of adipocyte development. Cell Growth Differ. Oct. 1997;8(10):1091-8.

Singh et al., Local deep tissue penetration of compounds after dermal application: structure-tissue penetration relationships. J Pharmacol Exp Ther. Nov. 1996;279(2):908-17.

Sjöquist et al., The pharmacokinetics of a new antiglaucoma drug, latanoprost, in the rabbit. Drug Metab Dispos. Aug. 1998;26(8):745-54.

Sjöquist et al., Ocular and systemic pharmacokinetics of latanoprost in humans. Surv Ophthalmol. Aug. 2002;47 Suppl 1:S6-12.

Skorski et al., Transformation of hematopoietic cells by BCR/ABL requires activation of a PI-3k/Akt-dependent pathway. EMBO J. Oct. 15, 1997;16(20):6151-61.

Slama et al., Effect of pioglitazone on HIV-1-related lipodystrophy: a randomized double-blind placebo-controlled trial (ANRS 113). Antivir Ther. 2008;13(1):67-76.

Smith et al., Effect of pioglitazone on body composition and energy expenditure: a randomized controlled trial. Metabolism. Jan. 2005;54(1):24-32.

Stella, Prodrugs as therapeutics. Expert Opin Ther Patents. 2004;14(3):277-80.

Sujobert et al., Essential role for the p110delta isoform in phosphoinositide 3-kinase activation and cell proliferation in acute myeloid leukemia. Blood. Aug. 1, 2005;106(3):1063-6. Epub Apr. 19, 2005.

(56) References Cited

OTHER PUBLICATIONS

Swinnen et al., Mimicry of a cellular low energy status blocks tumor cell anabolism and suppresses the malignant phenotype. Cancer Res. Mar. 15, 2005;65(6):2441-8.

Tamburini et al., Constitutive phosphoinositide 3-kinase/Akt activation represents a favorable prognostic factor in de novo acute myelogenous leukemia patients. Blood. Aug. 1, 2007;110(3):1025-8. Epub Apr. 10, 2007.

Tappeiner et al., [Orbital fat atrophy in glaucoma patients treated with topical bimatoprost—can bimatoprost cause enophthalmos?]. Klin Monbl Augenheilkd. May 2008;225(5):443-5. English abstract only.

Testa, Prodrug research: futile or fertile? Biochem Pharmacol. Dec. 1, 2004;68(11):2097-106.

Tong et al., Heightened expression of cyclooxygenase-2 and peroxisome proliferator-activated receptor-delta in human endometrial adenocarcinoma. Neoplasia. Nov.-Dec. 2000;2(6):483-90.

Tornqvist et al., Purification and some properties of a monoacylglycerol-hydrolyzing enzyme of rat adipose tissue. J Biol Chem. Feb. 10, 1976;251(3):813-9.

Tsao et al., Relative reciprocity of NRAS and PTEN/MMAC1 alterations in cutaneous melanoma cell lines. Cancer Res. Apr. 1, 2000;60(7):1800-4.

Tsuboi et al., Prostanoid EP4 receptor is involved in suppression of 3T3-L1 adipocyte differentiation. Biochem Biophys Res Commun. Sep. 24, 2004;322(3):1066-72.

Uddin et al., Role of phosphatidylinositol 3'-kinase/AKT pathway in diffuse large B-cell lymphoma survival. Blood. Dec. 15, 2006;108(13):4178-86. Epub Aug. 31, 2006.

Vippagunta et al., Crystalline solids. Adv Drug Deliv Rev. May 16, 2001;48(1):3-26.

Wagstaff et al., Rosiglitazone: a review of its use in the management of type 2 diabetes mellitus. Drugs. 2002;62(12)1805-37.

Wan et al., CCI-779 inhibits rhabdomyosarcoma xenograft growth by an antiangiogenic mechanism linked to the targeting of mTOR/Hif-1alpha/VEGF Signaling. Neoplasia. May 2006;8(5):394-401.

Wang et al., AMP-activated protein kinase and cancer. Acta Physiol (Oxf). May 2009;196(1):55-63. Epub Feb. 25, 2009.

Wang et al., Homozygous deletion of the PTEN tumor suppressor gene in a subset of prostate adenocarcinomas. Clin Cancer Res. Mar. 1998;4(3):811-5.

Wang et al., Pten deletion leads to the expansion of a prostatic sstem/progenitor cell subpopulation and tumor initiation. Proc Natl Acad Sci U S A. Jan. 31, 2006;103(5):1480-5. Epub Jan. 23, 2006.

Weber et al., Subcutaneous lipectomy causes a metabolic syndrome in hamsters. Am J Physiol Regul Integr Comp Physiol. Sep. 2000;279(3):R936-43.

Whang et al., Inactivation of the tumor suppressor PTEN/MMAC1 in advanced human prostate cancer through loss of expression. Proc Natl Acad Sci U S A. Apr. 28, 1998;95(9):5246-50.

Whiteman et al., Nuclear PTEN expression and clinicopathologic features in a population-based series of primary cutaneous melanoma. Int J Cancer. May 1, 2002;99(1):63-7.

Wilen et al., Strategies in Optical Resolution. Tetrahedron. 1977;33:2725-36.

Wilen, Tables of Resolving Agents and Optical Resolutions. Eliel, Ed. University of Notre Dame Press. Notre Dame, IN. 1972:268-90.

Wolff et al., Burger's Medicinal Chemistry and Drug Discovery. Fifth Edition. vol. I: Principles and Practice. 1994:975-7.

Woodward et al., Prostamides (prostaglandin-ethanolamides) and their pharmacology. Br J Pharmacol. Feb. 2008;153(3):410-9. Epub Aug. 27, 2007.

Woodward et al., The pharmacology of bimatoprost (Lumigan™). Surv Ophthalmol. May 2001;45 Suppl 4:S337-45.

Wu et al., Uncommon mutation, but common amplifications, of the PIK3CA gene in thyroid tumors. J Clin Endocrinol Metab. Aug. 2005;90(8):4688-93. Epub May 31, 2005.

Xin et al., Progression of prostate cancer by synergy of AKT with genotropic and nongenotropic actions of the androgen receptor. Proc Natl Acad Sci U S A. May 16, 2006;103(20):7789-94. Epub May 8, 2006.

Yam et al., Bilateral deepening of upper lid sulcus from topical bimatoprost therapy. J Ocul Pharmacol Ther. Oct. 2009;25(5):471-2.

Zakikhani et al., Metformin is an AMP kinase-dependent growth inhibitor for breast cancer cells. Cancer Res. Nov. 1, 2006;66(21):10269-73. Epub Oct. 23, 2006.

Zateyschikov, Thiazolidinediones and heart failure. Zhurnal Farmateka. 2005;3(99):1-6. http://www.pharmateca.ru/ru/archive/article/5901 [last accessed Apr. 16, 2014].

Ziegler, FDA Approves Latisse Eyelash Growth Product. Last accessed Jul. 24, 2012 at http://voices.yahoo.com/fda-approves-latisse-eyelash-growth-product-3520905.html?cat=39. 3 pages.

TOPICAL DOSAGE REGIMEN

RELATED APPLICATIONS

The present application is a national stage filing under 35 U.S.C. § 371 of international PCT application, PCT/US2015/037323, filed Jun. 24, 2015, which claims priority under 35 U.S.C. § 119(e) to U.S. provisional patent application, U.S. Ser. No. 62/018,233, filed Jun. 27, 2014, the entire contents of each of which are incorporated herein by reference.

FIELD OF THE INVENTION

This invention relates to a novel dosage regimen for a prostaglandin FP receptor agonist (a PFPRA compound), e.g., latanoprost, bimatoprost, tafluprost, travoprost, and prodrugs thereof, administered to the skin. The dosage regimen is useful for local reduction of subcutaneous fat, for example, in individuals with local excesses of subcutaneous fat. The dosage regimen improves a user's comfort and convenience while achieving the desired drug delivery.

BACKGROUND OF THE INVENTION

Local excesses of body fat are an important cause of aesthetic dissatisfaction, reduced self-esteem, and psychosocial distress. These excesses may involve, for example, prominent and undesired deposits of fat on the face, periorbital area, cheeks, chin, neck, chest, breast, abdomen, buttocks, hips, thighs, legs, and/or arms. One approach to reduce local excesses of body fat is to administer a fat-reducing drug. Some fat-reducing drugs are administered topically, i.e., to the skin surface.

Generally, the efficacy of a drug depends on the degree of drug exposure in the target tissue, e.g., the excess adipose tissue, e.g., subcutaneous fat. A standard measure of drug exposure is the area under the time-concentration curve (AUC) in the target tissue.

Many topical skin medications are used on a daily schedule, which is easy for users to remember. Furthermore, many daily skin medications, e.g., retinoids, acne medications, corticosteroids, antibiotics, antimycotics, and moisturizers, are left on the skin indefinitely and removed only incidentally, e.g., when the user next washes the skin.

Instructions that accompany many daily skin medications are silent as to whether and when the product should be removed. Thus, use of daily skin medications can routinely result in skin surface exposure for well over 12 hours, and in some cases 24 hours or more. These extended periods of skin surface exposure can be desirable when the therapeutic purpose is to treat the skin per se, because they maximize skin exposure over the dosage interval.

However, when the efficacy of a topical medication is determined by exposure in tissue other than the skin surface, an opportunity can exist to modify exposure beneficially in one tissue without compromise to the other. For example, exposure on the skin surface may merely be incidental to the route of delivery when exposure in subcutaneous fat (and the dermis adjacent to it) is more relevant to efficacy.

Therefore, there is a need for topical PFPRA dosage regimens to that improve patient comfort and convenience by reducing exposure on the skin surface without reducing exposure in subcutaneous fat and/or dermis.

SUMMARY OF THE INVENTION

The inventors have previously found that compounds of the prostaglandin FP receptor agonist (PFPRA compound) class can be administered to the skin to locally reduce adipose tissue under the skin, i.e., subcutaneous fat. See, e.g., U.S. Pat. No. 8,426,471 and U.S. Publication No. 2010/0234466, incorporated herein by reference.

The present invention arises from the experimental discovery that PFPRA compounds possess unexpectedly different pharmacokinetic properties in subcutaneous fat and dermis, compared to other previously studied compartments, such as plasma and the eye. Briefly, it has been discovered that when a PFPRA compound is applied to surface of skin (for example, in certain ointment and gel formulations), most of the delivery into the dermis or across the skin is achieved within 4-12 hours. Furthermore, the compound (or its active metabolite) remains in the dermis or subcutaneous fat for 24 hours or more. This is surprising, because it is typical for PFPRA compounds to be rapidly metabolized and cleared from the body. For example, when latanoprost is administered intravenously or ophthalmically, the active metabolite, latanoprost free acid, is eliminated with a half-life of about 9-85 minutes. However, it has now been discovered that when latanoprost is administered percutaneously to subcutaneous fat, the active metabolite, latanoprost free acid, is eliminated slowly, with a half-life of about 18-24 hours (Example 5).

Based on the above experimental results, the inventors have recognized that if certain topical compositions comprising a PFPRA compound are removed after most of a daily dose is delivered (e.g., about 4 to 8 hours after application), longer exposure on the skin surface is unnecessary, and the topical composition or residue thereof can be removed from the skin surface. Thus, patient comfort and convenience can be promoted without compromising delivery of the drug to the dermis and fat. Removal of the topical composition, in this instance, means gross removal (e.g., removal of at least 80%, 85%, 90%, 95%, 99%, or 100%) of the remaining topical composition or residue thereof, including any remaining PFPRA compound and any remaining excipients, from the skin surface, e.g., by washing, bathing, scrubbing, scraping, removing patches, and the like, and/or stripping from the skin. It should be understood that some ingredients of the topical composition can be volatile and can evaporate following application to the skin thereby leaving a residue. Other ingredients do not necessarily evaporate. For example, PFPRA compounds are not volatile compounds.

Thus, in one aspect, provided is a prostaglandin FP receptor agonist compound for topical use in reducing body fat, whereby the duration of skin surface exposure to the composition or residue thereof is between about 4 hours and about 12 hours per dose of the composition.

In another aspect, provided is a method for locally reducing body fat in a subject in need thereof, the method comprising administering a topical composition comprising a PFPRA compound to the skin surface, and removing the topical composition or residue thereof from the skin surface between about 4 hours and about 12 hours after said administering. In certain embodiments, the dermis has taken up at least 80% of maximal load by the PFPRA compound (or active metabolite thereof) within about 4 to about 12 hours of administration (with maximal load as defined herein). In certain embodiments, the step of removing comprises removing the composition or residue thereof from the skin surface after the dermis has taken up at least 80% of maximal load. In certain embodiments, more than about 60 percent of the 24-hour transcutaneous flux occurs within 4 to 12 hours after administration. In certain embodiments, the step of removing comprises removing the composition or residue thereof from the skin surface after more than about 60 percent of the 24-hour transcutaneous flux has occurred.

In another aspect, provided is a kit comprising a topical fat-reducing composition and instructions for use, wherein the composition comprises a PFPRA compound, and wherein the instructions provide for a duration of skin surface exposure to the composition or residue thereof of between about 4 hours and about 12 hours per dose of the composition.

In certain embodiments of the uses, methods, and kits described herein, the dose frequency is about once every 24 hours.

In certain embodiments, the PFPRA compound is selected from the group consisting of latanoprost, tafluprost, travoprost, bimatoprost, and pharmaceutically acceptable salts, hydrates, solvates, stereoisomers, polymorphs, tautomers, isotopically enriched derivatives, or prodrugs thereof. In certain embodiments, the PFPRA compound is hydrolyzed in the skin to an active metabolite. For example, in certain embodiments, latanoprost is a prodrug that is hydrolyzed in the skin to yield latanoprost free acid. In certain embodiments, tafluprost is a prodrug that is hydrolyzed in the skin to yield tafluprost free acid. In certain embodiments, travoprost is a prodrug that is hydrolyzed in the skin to yield travoprost free acid (aka fluprostenol). In certain embodiments, bimatoprost is a prodrug that is hydrolyzed in the skin to yield bimatoprost free acid.

Other objects and advantages will become apparent to those skilled in the art from consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Certain compounds as described herein can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds as described herein are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "aliphatic" refers to an alkyl, alkenyl, alkynyl, or carbocyclyl group, as defined herein.

As used herein, alone or as part of another group, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently unsubstituted (an "unsubstituted alkyl") or substituted (a "substituted alkyl") are substituted with one or more substituents. In certain embodiments, the alkyl group is an unsubstituted $C_{1-30}$ alkyl. In certain embodiments, the alkyl group is a substituted $C_{1-30}$ alkyl.

As used herein "perhaloalkyl" as defined herein refers to an alkyl group having from having from 1 to 30 carbon atoms wherein all of the hydrogen atoms are each independently replaced halogen, e.g., selected from fluoro, bromo, chloro or iodo ("$C_{1-30}$ perhaloalkyl"). In some embodiments, the perhaloalkyl has 1 to 20 carbon atoms ("$C_{1-20}$ perhaloalkyl"). In some embodiments, the perhaloalkyl has 1 to 10 carbon atoms ("$C_{1-10}$ perhaloalkyl"). In some embodiments, the perhaloalkyl has 1 to 6 carbon atoms ("$C_{1-6}$ perhaloalkyl"). In some embodiments, the perhaloalkyl has 1 to 5 carbon atoms ("$C_{1-5}$ perhaloalkyl"). In some embodiments, the perhaloalkyl has 1 to 4 carbon atoms ("$C_{1-4}$ perhaloalkyl"). In some embodiments, the perhaloalkyl has 1 to 3 carbon atoms ("$C_{1-3}$ perhaloalkyl"). In some embodiments, the perhaloalkyl has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, "alkyloxy" refers to an alkyl group, as defined herein, substituted with an oxygen atom, wherein the point of attachment is the oxygen atom. In certain embodiments, the alkyl group has 1 to 30 carbon atoms ("$C_{1-30}$ alkyloxy"). In some embodiments, the alkyl group has 1 to 20 carbon atoms ("$C_{1-20}$ alkyloxy"). In some embodiments, the alkyl group has 1 to 10 carbon atoms ("$C_{1-10}$ alkyloxy"). In some embodiments, the alkyl group has 1 to 6 carbon atoms ("$C_{1-6}$ alkyloxy"). In some embodiments, the alkyl group has 1 to 4 carbon atoms ("$C_{1-4}$ alkyloxy"). Examples of $C_{1-4}$alkyloxy groups include methoxy ($C_1$), ethoxy ($C_2$), propoxy ($C_3$), isopropoxy ($C_3$), butoxy ($C_4$), tert-butoxy ($C_5$) and the like. Examples of $C_{1-6}$ alkyloxy groups include the aforementioned $C_{1-4}$ alkyloxy groups as well as pentyloxy ($C_5$), isopentyloxy ($C_5$), neopentyloxy ($C_5$), hexyloxy ($C_6$) and the like. Unless otherwise specified, each instance of the alkyl moiety of the alkyloxy group is independently unsubstituted (an "unsubstituted alkyloxy") or substituted (a "substituted alkyloxy") with one or more substituents. In certain embodiments, the alkyloxy group is an unsubstituted $C_{1-30}$ alkyloxy. In certain embodiments, the alkyloxy group is a substituted $C_{1-30}$ alkyloxy.

As used herein, "alkylcarboxy" refers to a group of the formula —C(=O)OR$^a$ or —OC(=O)R$^a$, wherein R$^a$ is an alkyl group as defined herein. In certain embodiments, the alkyl of the alkylcarboxy group has 1 to 6 carbon atoms ("$C_{1-6}$ alkylcarboxy"). In some embodiments, the alkyl of the alkylcarboxy group has 1 to 5 carbon atoms ("$C_{1-5}$ alkylcarboxy"). In some embodiments, the alkyl of the alkylcarboxy group has 1 to 4 carbon atoms ("$C_{1-4}$ alkylcarboxy"). In some embodiments, the alkyl of the alkylcarboxy group has 1 to 3 carbon atoms ("$C_{1-3}$ alkylcarboxy"). In some embodiments, the alkyl of the alkylcarboxy group has 1 to 2 carbon atoms ("$C_{1-2}$ alkylcarboxy"). Unless otherwise specified, each instance of the alkyl of the alkylcarboxy group is independently unsubstituted (an "unsubstituted alkylcarboxy") or substituted (a "substituted alkylcarboxy") with one or more substituents. In certain embodiments, the alkylcarboxy group is an unsubstituted $C_{1-6}$ alkylcarboxy. In certain embodiments, the alkylcarboxy group is a substituted $C_{1-6}$ alkylcarboxy.

As used herein, alone or as part of another group, "alkenyl" refers to a radical of a straight-chain or branched hydrocarbon group having from 2 to 30 carbon atoms and one or more carbon-carbon double bonds ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-30}$ alkenyl. In certain embodiments, the alkenyl group is a substituted $C_{2-30}$ alkenyl.

As used herein, alone or as part of another group, "alkynyl" refers to a radical of a straight-chain or branched hydrocarbon group having from 2 to 30 carbon atoms and one or more carbon-carbon triple bonds ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atom ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-30}$ alkynyl. In certain embodiments, the alkynyl group is a substituted $C_{2-30}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). Exemplary carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with 1, 2, 3, 4, or 5 substituents as described herein. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-7}$ cycloalkyl groups include the aforementioned $C_{3-6}$ cycloalkyl groups as well as cycloheptyl ($C_7$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-7}$ cycloalkyl. In certain embodiments, the cycloalkyl group is a substituted $C_{3-7}$ cycloalkyl.

As used herein, alone or as part of another group, "heterocyclyl" refers to a radical of a 3- to 8-membered non-aromatic ring system having ring carbon atoms and 1 to 4 ring heteroatoms, wherein each heteroatom is independently selected from nitrogen, oxygen and sulfur ("3-8-membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8-membered heterocyclyl"). In some embodiments, a heterocyclyl group is a 5-6-membered non-aromatic ring system having ring carbon atoms and 1-4 ring heteroatoms, wherein each heteroatom is independently selected from nitrogen, oxygen and sulfur ("5-6-membered heterocyclyl"). In some embodiments, the 5-6-membered heterocyclyl has 1-3 ring heteroatoms selected from nitrogen, oxygen and sulfur. In some embodiments, the 5-6-membered heterocyclyl has 1-2 ring heteroatoms selected from nitrogen, oxygen and sulfur. In some embodiments, the 5-6-membered heterocyclyl has 1 ring heteroatom selected from nitrogen, oxygen and sulfur. Exemplary 3-membered heterocyclyls containing 1 heteroatom include, without limitation, aziridinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-8-membered heterocyclyl. In certain embodiments, the heterocyclyl group is a substituted 3-8-membered heterocyclyl.

As used herein, alone or as part of another group, "aryl" refers to a radical of a monocyclic or polycyclic (e.g., bicyclic or tricyclic) 4n+2 aromatic ring system having 6-10 ring carbon atoms and zero heteroatoms provided in the aromatic ring system ("$C_{6-10}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as described herein. In certain embodiments, the aryl group is an unsubstituted $C_{6-10}$ aryl. In certain embodiments, the aryl group is a substituted $C_{6-10}$ aryl.

As used herein, alone or as part of another group, "heteroaryl" refers to a radical of a 5-14-membered monocyclic or polycyclic (e.g., bicyclic) 4n+2 aromatic ring system having 4-10 ring carbon atoms and 1-4 ring heteroatoms provided in the aromatic ring system, wherein each heteroatom is independently selected from nitrogen, oxygen and sulfur ("5-10-membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10-membered aromatic ring system having ring carbon atoms and 1-4 ring heteroatoms provided in the aromatic ring system, wherein each heteroatom is independently selected from nitrogen, oxygen and sulfur ("5-10-membered heteroaryl"). In some embodiments, a heteroaryl group is a 5-8-membered aromatic ring system having ring carbon atoms and 1-4 ring heteroatoms provided in the aromatic ring system, wherein each heteroatom is independently selected from nitrogen, oxygen and sulfur ("5-8-membered heteroaryl"). In some embodiments, a heteroaryl group is a 5-6-membered aromatic ring system having ring carbon atoms and 1-4 ring heteroatoms provided in the aromatic ring system, wherein each heteroatom is independently selected from nitrogen, oxygen and sulfur ("5-6-membered heteroaryl"). In some embodiments, the 5-6-membered heteroaryl has 1-3 ring heteroatoms selected from nitrogen, oxygen and sulfur. In some embodiments, the 5-6-membered heteroaryl has 1-2 ring heteroatoms selected from nitrogen, oxygen and sulfur. In some embodiments, the 5-6-membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl (aka benzothienyl), isobenzothiophenyl, benzofuranyl, benzoisofuranyl, benzimidazolyl, benzoxazolyl, benzisoxazolyl, benzoxadiazolyl, benzothiazolyl, benzisothiazolyl, benzothiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-10-membered heteroaryl. In certain embodiments, the heteroaryl group is a substituted 5-10-membered heteroaryl.

Alkyl, alkenyl, alkynyl, carbocyclyl, heterocyclyl, aryl, and heteroaryl, referred to without the suffix "-ene," describe a monoradical of alkyl, alkenyl, alkynyl, carbocyclyl, heterocyclyl, aryl, or heteroaryl, respectively, and as defined herein, wherein the monoradical is directly attached to a parent molecule or to another group by one bond (e.g., one single or double bond). Monoradical groups, as defined herein, may also be optionally substituted. Groups referred to with the suffix "-ene", such as alkylene, alkenylene, alkynylene, carbocyclylene, heterocyclylene, arylene and heteroarylene groups, describe a diradical of alkyl, alkenyl, alkynyl, carbocyclyl, heterocyclyl, aryl, or heteroaryl, respectively, and as defined herein, wherein the diradical is between and directly attached to two groups (e.g., between the parent molecule and another group) by two bonds (e.g., single or double bonds). Diradical groups may also be optionally substituted.

Aliphatic, alkyl, alkenyl, alkynyl, carbocyclyl, heterocyclyl, aryl, and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group (e.g., 1, 2, 3, 4, or 5 positions), and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —SC(=O)OR$^{aa}$, —OC(=O)SR$^{aa}$, —SC(=O) R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, or two $R^{aa}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, or two $R^{bb}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, or two $R^{bb}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N(O$R^{ee}$)$R^{ff}$, —SH, —S$R^{ee}$, —SS$R^{ee}$, —C(=O)$R^{ee}$, —CO$_2$H, —C(=O)O$R^{ee}$, —OC(=O)$R^{ee}$, —OC(=O)O$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of e is, independently, selected from hydrogen, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, or two $R^{ff}$ groups are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl), —N($C_{1-6}$ alkyl)$_2$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl), —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl), —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl), —C(=NH)NH($C_{1-6}$ alkyl), —C(=NH)NH$_2$, —OC(=NH) N($C_{1-6}$ alkyl), —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$ ($C_{1-6}$ alkyl), —SO$_2$N($C_{1-6}$ alkyl), —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl), —OSi ($C_{1-6}$ alkyl)-C(=S)N($C_{1-6}$ alkyl), C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O) ($C_{1-6}$ alkyl), —OP(=O)($C_{1-6\ alkyl}$)$_2$, —OP(=O)(O$C_{1-6}$ alkyl)$_2$, $C_{1-6}$ alkyl, $C_{2-6}$ alkenyl, $C_{2-6}$ alkynyl, $C_{3-7}$ carbocyclyl, 3-8-membered-heterocyclyl, $C_{6-10}$ aryl, and 5-10-membered heteroaryl; or two geminal $R^{gg}$ substituents can be joined to form =O or =S.

In certain embodiments, the carbon atom substituent is selected from the group consisting of halogen, —CN, —NO$_2$, —N$_3$, —SO$_2$H, —SO$_3$H, —OH, —O$R^{aa}$, —N($R^{bb}$)$_2$, —SH, —S$R^{aa}$, —C(=O)$R^{aa}$, —CO$_2$H, —CHO, —CO$_2$$R^{aa}$, —OC(=O)$R^{aa}$, —OCO$_2$$R^{aa}$, —C(=O)N($R^{bb}$)$_2$, —OC(=O)N($R^{bb}$)$_2$, —N$R^{bb}$C(=O) $R^{aa}$, —N$R^{bb}$CO$_2$$R^{aa}$, —N$R^{bb}$C(=O)N($R^{bb}$)$_2$, —C(=O) N$R^{bb}$SO$_2$$R^{aa}$, —N$R^{bb}$SO$_2$$R^{aa}$, —SO$_2$N($R^{bb}$)$_2$, —SO$_2$$R^{aa}$, —SO$_2$O$R^{aa}$, —S(=O)$R^{aa}$, —OS(=O)$R^{aa}$, —Si($R^{aa}$)$_3$, $C_{1-6}$ alkyl, $C_{2-6}$ alkenyl, $C_{2-6}$ alkynyl, $C_{3-7}$ carbocyclyl, 3-8-membered heterocyclyl, $C_{6-10}$ aryl, and 5-10-membered heteroaryl, or two $R^{cc}$ groups attached to an N atom are joined to form a 3-8-membered heterocyclyl or 5-10-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

As used herein, the term "hydroxyl" or "hydroxy" refers to the group —OH. The term "substituted hydroxyl" or "substituted hydroxy," by extension, refers to a hydroxyl group wherein the oxygen atom is substituted with a group other than hydrogen, e.g., selected from —O$R^{aa}$, —ON($R^{bb}$)$_2$, —OC(=O)$R^{aa}$, —OC(=O)S$R^{aa}$, —OCO$_2$$R^{aa}$, —OC(=O)N($R^{bb}$)$_2$, —OC(=N$R^{bb}$)$R^{aa}$, —OC(=N$R^{bb}$) O$R^{aa}$, —OC(=N$R^{bb}$)N($R^{bb}$)$_2$, —OS(=O)$R^{aa}$, —OSO$_2$$R^{aa}$, —OSi($R^{aa}$)$_3$, —OP($R^{cc}$)$_2$, —OP($R^{cc}$)$_3$, —OP (=O)$_2$$R^{aa}$, —OP(=O)($R^{aa}$)$_2$, —OP(=O)(O$R^{cc}$)$_2$, —OP (=O)$_2$N($R^{bb}$)$_2$, and —OP(=O)(N$R^{bb}$)$_2$, wherein $R^{aa}$, $R^{bb}$, and $R^{cc}$ are as defined herein.

As used herein, the term "thiol" or "thio" refers to the group —SH. The term "substituted thiol" or "substituted thio," by extension, refers to a thiol group wherein the sulfur atom is substituted with a group other than hydrogen, and includes groups selected from —S$R^{aa}$, —S=S$R^{cc}$, —SC (=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$.

As used herein, the term "substituted amino" refers to a monosubstituted, disubstituted, or trisubstituted amino group, as defined herein.

As used herein, the term "monosubstituted amino" refers to an amino group substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "halo" or "halogen" refers to fluorine (fluoro, —F), chlorine (chloro, —Cl), bromine (bromo, —Br), or iodine (iodo, —I).

As used herein, "nitro" refers to the group —NO$_2$.

As used herein, "cyano" refers to the group —CN.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an "amino protecting group". Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiosuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrroline-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxy-benzenesulfenamide, triphenylmethylsulfenamide, and 3-nitropyridinesulfenamide (Npys).

In certain embodiments, the substituent present on the oxygen atom is an "oxygen protecting group". Oxygen protecting groups include, but are not limited to —R$^{aa}$, —N(R$^{bb}$)$_2$, —C(=O)R$^{aa}$, —C(=O)OR$^{aa}$, —C(=O)SR$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O) (R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, the Examples and in the Claims. The invention is not intended to be limited in any manner by the above exemplary listing of substituents.

As used herein, the terms "salt", "acceptable salt", or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" means a compound that can hydrolyze, oxidize, or otherwise react under biological conditions (e.g., in vitro or in vivo enzymatic conditions) to provide a pharmacologically active compound. In this instance, the "prodrug" is a compound administered to a subject, and the pharmacologically active compound is the "active metabolite thereof." Exemplary prodrugs include esters, amides, and/or thioamides of the parent free acid, and compounds wherein a hydroxyl group on the parent compound (e.g., a pentacyclic hydroxyl group of the PFPRA compound) is acylated. In certain cases, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

Other Definitions

"Disease", "disorder," and "condition" are used interchangeably herein.

As used herein, an "individual" or "subject" to which administration is contemplated includes, but is not limited to, humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the mammal is a human.

As used herein, "local administration" or "administering locally" or "local effect" means administration/application of the active ingredient or active metabolite thereof directly, or in proximity to, a part of the body, tissue, or lesion where said active substance is intended to exert its action. This may include, for example, topical administration to a part of the skin.

As used herein, unless otherwise specified, "topical administration" or "topically" means application to the surface of the skin.

As used herein, and unless otherwise specified, a "therapeutically effective amount" "an amount sufficient" or "sufficient amount" of a compound means the level, amount or concentration of the compound needed to treat a disease, disorder or condition, or to reduce or lower a particular parameter (e.g., body fat) in the body of a subject, without causing significant negative or adverse side effects to body or the treated tissue. The term "therapeutically effective amount" can encompass an amount that improves overall therapy, reduces or avoids symptoms or causes of disease or condition, or enhances the therapeutic efficacy of another therapeutically active agent.

As used herein, the terms "reduce", "reduction", "reducing", "lower", or "lowering" means to diminish or lessen the volume, size, mass, bulk, density, amount, and/or quantity of a substance (e.g., body fat, adipose tissue) in the body of a subject.

As used herein, the term "eliminate" means to completely remove any unwanted or undesired volume, size, mass, bulk, density, amount, and/or quantity of a substance (e.g., excess body fat, excess adipose tissue) in the body of a subject.

As used herein, "suffer," "suffers" or "suffering from" refers to a subject diagnosed with a particular disease or condition. As used herein, "likely to suffer" refers to a subject who has not been diagnosed with a particular disease or condition by a medical practitioner, but has a predisposition (e.g., genetic and/or physiologic predisposition), or exhibits signs or symptoms of the disease or condition.

As used herein, and unless otherwise specified, the terms "treat," "treating" and "treatment" contemplate an action that occurs while a subject is suffering from the specified disease or condition, which reduces the severity of the disease or condition, or retards or slows the progression of the disease or condition.

As used herein, unless otherwise specified, the terms "prevent," "preventing" and "prevention" contemplate an action that occurs before a subject begins to suffer from the specified disease or condition, which inhibits or reduces the severity of the disease or condition.

Conditions for which treatment and prevention are contemplated may be further classified as a medical condition or a cosmetic condition. A "medical condition", as used herein, refers to an abnormal condition that affects the body. A "cosmetic condition", as used herein, refers to a condition other than a medical condition that affects the physical appearance of the body. A cosmetic condition can occur, for example, due to normal processes in a body, such as aging, pregnancy, puberty, and exposure to the sun or the elements, or due to normal features of a body, such as inherited facial features or body shapes that are found in healthy individuals. Various medical and cosmetic conditions are described herein. A "cosmetic method" refers to a method or procedure intended to ameliorate a cosmetic condition in the subject, e.g., for the beautification of the subject's body or a part thereof, e.g., to ameliorate a "cosmetic condition in the subject" is contemplated useful for such purpose. A "therapeutic method" refers to a method or procedure intended to treat a medical condition, and a "pharmaceutical composition" is contemplated useful for such purpose. However, while pharmaceutical compositions are contemplated useful for therapeutic and prophylactic purposes, and cosmetic compositions are contemplated useful for cosmetic purposes, there may be overlap between the two compositions in terms of use of the composition. For example, a pharmaceutical composition is also contemplated useful for beautification purposes.

As used herein, the term "medicament" is used interchangeably with the term "pharmaceutical composition."

As used herein, unless otherwise specified, "excess submental fat" means excess fat on the body region including the mentum, the underside of the jaw, and the anterior neck, for example to the level of the inferior border of the cricoid.

As used herein, unless otherwise specified, "steatoblepharon" refers to a condition characterized by excess fat of the eyelids and/or periorbital tissue. The excess fat can be due to prolapse of orbital or periorbital fat. Steatoblepharon can occur in the lower or upper eyelid, or both. Steatoblepharon can be considered a cause of "eye bags."

The presence, amount, or severity of excess fat can be assessed objectively, e.g., by magnetic resonance imaging, computed tomography, biopsy, or skin calipers, or subjectively, e.g., by a clinician, a patient, or other observer, optionally with reference to a photonumeric, verbal, or descriptive scale or classification system, e.g., a five-step severity scale.

DETAILED DESCRIPTION OF CERTAIN EMBODIMENTS OF THE INVENTION

The inventors have previously found that compounds of the prostaglandin FP receptor agonist (PFPRA compound) class can be administered to the skin to locally reduce adipose tissue under the skin, i.e., subcutaneous fat. See, e.g., U.S. Pat. No. 8,426,471 and U.S. Publication No. 2010/0234466.

The present invention arises from the experimental discovery that PFPRA compounds possess unexpectedly different pharmacokinetic properties in subcutaneous fat and dermis, compared to other previously studied compartments, such as plasma and the eye. Briefly, it has been discovered that when a PFPRA compound is applied to surface of skin (for example, in certain ointment and gel formulations), most of the delivery into the dermis or across the skin is achieved within 4-12 hours. Furthermore, the compound (or its active metabolite) remains in the dermis or subcutaneous fat for 24 hours or more. This is surprising, because it is typical for PFPRA compounds to be rapidly metabolized and cleared from the body. For example, when latanoprost is administered intravenously or ophthalmically, the active metabolite is eliminated with a half-life of about 9-85 minutes. However, it has now been discovered that when the compound is administered percutaneously to subcutaneous fat, the active metabolite is eliminated slowly, with a half-life of about 18-24 hours (Example 5).

Thus, the inventors have recognized that if a topical composition or residue thereof comprising a PFPRA compound is removed from the skin surface after the dermis is maximally loaded (e.g., removed about 4 to about 12 hours, e.g., about 4 to about 8 hours, after application), further exposure on the skin surface can be avoided, and patient comfort and convenience can be promoted, without compromising delivery of the drug to the dermis and fat. Comforts and conveniences include the freedom to wash the skin for hygienic purposes, to apply cosmetics or fragrances to the skin, to wear certain clothing without risk of staining the clothing, and to interact with other persons without the odor or appearance (e.g., sheen or greasiness) of a pharmaceutical composition on one's body. Examples of side effects that can occur with any topical composition, and that can be reduced or avoided by a reduction in the exposure time of a topical composition, include greasy or oily skin, acne, dry skin, irritation, redness, and itch.

Thus, in one aspect, provided is a prostaglandin FP receptor agonist compound for topical use in reducing body fat, whereby the duration of skin surface exposure to the composition or residue thereof is between about 4 hours and about 12 hours per dose of the composition.

In another aspect, provided is a method for locally reducing body fat in a subject in need thereof, the method comprising administering a topical composition comprising a PFPRA compound to the skin surface and removing the topical composition or residue thereof from the skin surface between about 4 hour and about 12 hours, inclusive, after said administering. In certain embodiments, the dermis has taken up at least 80% of maximal load by the PFPRA compound (or active metabolite thereof) within about 4 to about 12 hours of administration. In certain embodiments, the step of removing comprises removing the composition or residue thereof from the skin surface after the dermis has taken up at least 80% of maximal load.

In another aspect, provided is a kit comprising a topical fat-reducing composition and instructions for use, wherein the composition comprises a PFPRA compound, and wherein the instructions provide for a duration of skin surface exposure to the composition or residue thereof of between about 4 hours and about 12 hours per dose of the composition.

In certain embodiments of the uses, methods, and kits described herein, the dose frequency is about once every 24 hours.

PFPRA Compounds

As used herein, a "PFPRA compound" can be any therapeutically relevant, naturally occurring or synthetic prostaglandin or prostaglandin analog, provided that it or its active metabolite (e.g., if an ester, the parent acid) agonizes a prostaglandin FP receptor, e.g., as determined using afunctional assay. "Agonizes" or "agonsim" may refer to, for example, a half maximal effective concentration ($EC_{50}$) of 1 micromolar or less, preferably 100 nanomolar or less. A functional assay may be, for example, assessment of phosphoinositide turnover in HEK293 cells expressing a cloned FP prostaglandin receptor. See, e.g., Sharif et al., *J. Ocular Pharmacol. Ther.* 2002; 18:313-324. Many PFPRA compounds can be classified as prostaglandins, prostanoids, or prostamides. Naturally occurring prostaglandins are a class of structurally related eicosanoid hormones that are derived enzymatically from arachidonic acid. An example of a naturally occurring prostaglandin PFPRA compound is prostaglandin F2α. Exemplary synthetic prostaglandins, which are prostaglandin F2α analogs, include, but are not limited to, latanoprost, latanoprost free acid, bimatoprost, bimatoprost free acid, tafluprost, tafluprost free acid, travoprost, travoprost free acid (a.k.a. fluprostenol), and prodrugs (e.g., 9-, 11-, and/or 15-ester derivatives) thereof.

In certain embodiments, the PFPRA compound is a compound of Formula (I) or (II):

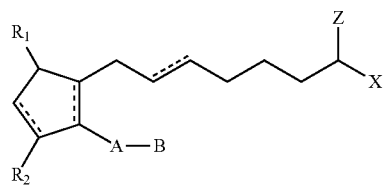

(I)

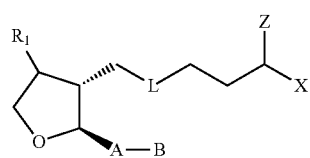

(II)

or a pharmaceutically acceptable salt, hydrate, solvate, stereoisomer, polymorph, tautomer, isotopically enriched derivative, or prodrug thereof;

wherein:

L is a group of the formula

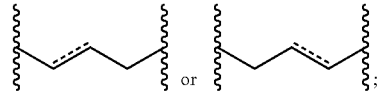

each instance of

----- independently represents a single bond or a double bond which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is –$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(=O)$R_5$, or —C(=O)$OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring;

Z is =O, =S, or =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms;

with regard to the compound of Formula (I), one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$alkyl, optionally substituted $C_{2-20}$alkenyl, optionally substituted $C_{2-20}$ alkynyl, or —$(CH_2)_mR_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl; and with regard to the compound of Formula (II), $R_1$ is =O, —OH, or —O(CO)$R_6$, wherein $R_6$ is an optionally substituted $C_{1-20}$alkyl, optionally substituted $C_{2-20}$alkenyl, optionally substituted $C_{2-20}$ alkynyl, or —$(CH_2)_mR_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, the endocyclic dotted lines of Formula (I) (i.e., depicted in the 5-membered ring) each represent a single bond.

For example, in certain embodiments, wherein the endocyclic dotted lines of Formula (I) each represent a single bond, provided is a compound having any one of the following stereochemistry:

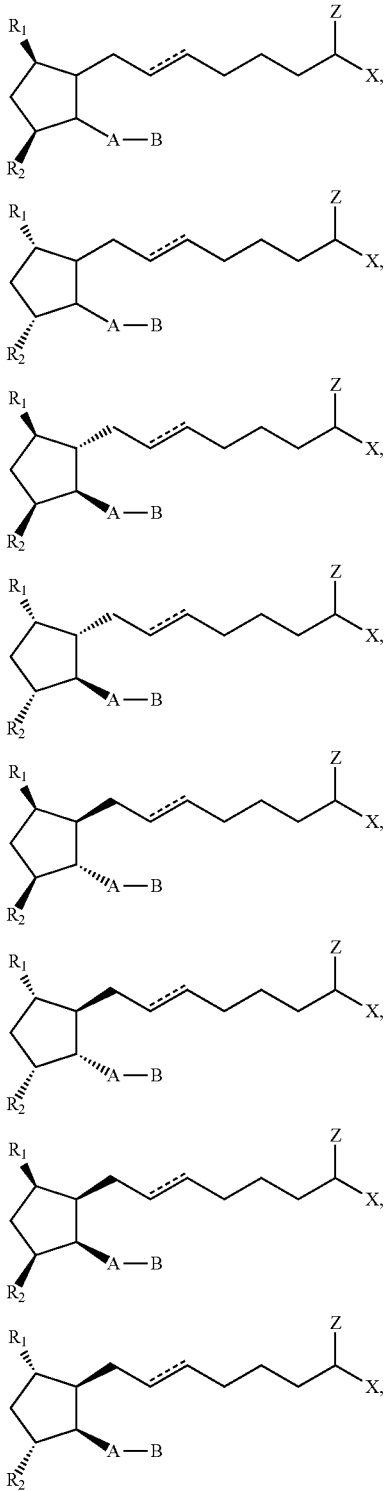

-continued

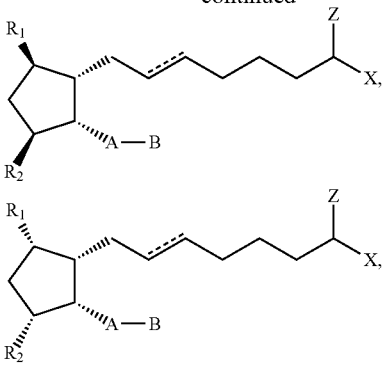

pharmaceutically acceptable salt, hydrate, solvate, stereoisomer, polymorph, tautomer, isotopically enriched derivative, or prodrug thereof, wherein ======, $R_1$, $R_2$, A, B, Z and X are as defined herein.

In certain embodiments, the exocyclic dotted line ====== (i.e., depicted outside of the 5-membered ring) of Formula (I) or (II) or a subset thereof represents a double bond in the cis or trans configuration. In certain embodiments, the exocyclic dotted line ====== represents a double bond in the cis configuration.

In certain embodiments, each instance of ====== independently represents a single bond or a double bond which can be in the cis or trans configuration.

As generally defined above, one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$alkyl, optionally substituted $C_{2-20}$alkenyl, optionally substituted $C_{2-20}$ alkynyl, or —(CH$_2$)$_m$R$_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, $R_1$ is =O; and $R_2$ is H.

In certain embodiments, one of $R_1$ and $R_2$ is —OH, substituted hydroxyl, or —O(CO)$R_6$, and the other one is —OH, substituted hydroxyl, or —O(CO)$R_6$.

In certain embodiments, both $R_1$ and $R_2$ are —OH.

In certain embodiments, one of $R_1$ and $R_2$ is —OH, and the other one is —O(CO)$R_6$. In certain embodiments, $R_1$ is —OH, and $R_2$ is —O(CO)$R_6$. In certain embodiments, $R_2$ is —OH, and $R_1$ is —O(CO)$R_6$. In certain embodiments, $R_6$ is an optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_6$ is —(CH$_2$)$_r$CH$_3$ wherein r is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$.

As generally defined above, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one or more —O— or —S— groups.

In certain embodiments, A is optionally substituted $C_{1-10}$alkylene, optionally substituted $C_{2-10}$alkenylene or optionally substituted C$_{2-10}$alkynylene, wherein the alkylene, alkenylene, or alkynylene group is optionally interrupted by one —O— group.

In certain embodiments, A is optionally substituted C$_{4-6}$alkylene, optionally substituted C$_{4-6}$alkenylene or optionally substituted C$_{4-6}$alkynylene, wherein the alkylene, alkenylene, or alkynylene group is optionally interrupted by one —O— group.

In certain embodiments, A is optionally substituted C$_{4-6}$alkylene optionally interrupted by one —O— group. In certain embodiments, A is optionally substituted C$_{4-6}$alkenylene optionally interrupted by one —O— group. In certain embodiments, A is optionally substituted C$_{4-6}$alkynylene optionally interrupted by one —O— group.

In certain embodiments, A is substituted with one or more groups selected from the group consisting of halogen, —OH, substituted hydroxyl, or —O(CO)R$_8$, wherein R$_8$ is optionally substituted C$_{1-20}$alkyl, optionally substituted C$_{2-20}$alkenyl, optionally substituted C$_{2-20}$alkynyl, or —(CH$_2$)$_m$R$_9$ wherein m is 0 or an integer between 1-10, inclusive, and R$_9$ is optionally substituted C$_{3-7}$carbocyclyl, optionally substituted C$_{6-10}$aryl, and optionally substituted 5-14-membered-heteroaryl.

In certain embodiments, A is substituted with =O.

In certain embodiments, A is substituted with —OC(=O)R$_8$, wherein R$_8$ is optionally substituted C$_{1-20}$alkyl, optionally substituted C$_{2-20}$alkenyl, optionally substituted C$_{2-20}$alkynyl, or —(CH$_2$)$_m$R$_9$, wherein m is 0 or an integer between 1-10, inclusive, and R$_9$ is optionally substituted C$_{3-7}$carbocyclyl, optionally substituted C$_{6-10}$aryl, or optionally substituted 5-14-membered-heteroaryl.

In certain embodiments, A is substituted with —OH or substituted hydroxyl.

In certain embodiments, A is substituted with substituted hydroxyl.

In certain embodiments, A is substituted with —OH.

In certain embodiments, A is a group of the Formula (i), (ii), (iii), (iv), (v), or (vi):

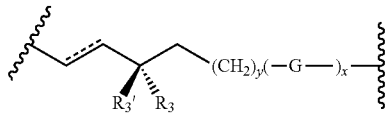

(i)

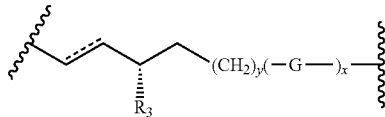

(ii)

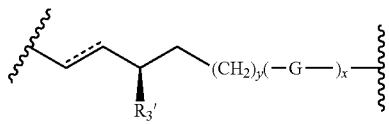

(iii)

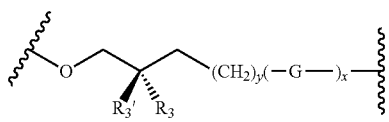

(iv)

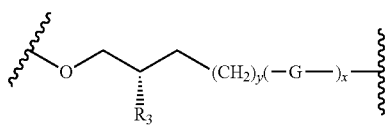

(v)

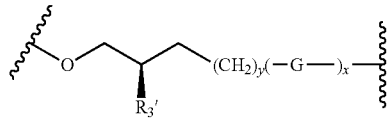

(vi)

wherein each instance of ≡≡≡≡ independently represents a single bond or a double bond which can be in the cis or trans configuration;

each instance of R$_3$ and R$_3$' is hydrogen, halogen, —OH, substituted hydroxyl, or —O(CO)R$_8$, wherein R$_8$ is optionally substituted C$_{1-20}$alkyl, optionally substituted C$_{2-20}$alkenyl, optionally substituted C$_{2-20}$alkynyl, or —(CH$_2$)$_m$R$_9$ wherein m is 0 or an integer between 1-10, inclusive, and R$_9$ is optionally substituted C$_{3-7}$carbocyclyl, optionally substituted C$_{6-10}$aryl, or optionally substituted 5-14-membered-heteroaryl, or R$_3$ and R$_3$' are joined to form =O;

G is —O— or —S—;

y is 0, 1, or 2; and x is 0 or 1.

In certain embodiments, G is —O—. In certain embodiments, G is —S—.

In certain embodiments, ≡≡≡≡ of Formula (i), (ii), or (iii) represents a double bond in the cis configuration.

In certain embodiments, ≡≡≡≡ of Formula (i), (ii), or (iii) represents a double bond in the trans configuration.

In certain embodiments, the group of the Formula (i) is of the formula:

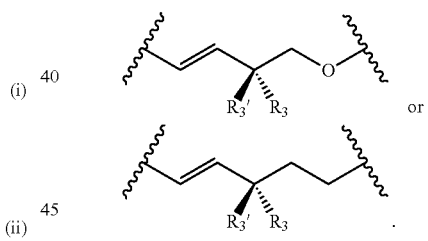

In certain embodiments, the group of the Formula (ii) is of the formula:

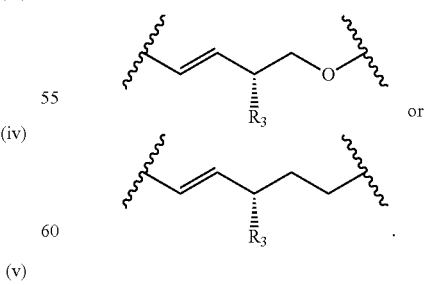

In certain embodiments, ≡≡≡≡ of Formula (i), (ii), or (iii) represents a single bond.

In certain embodiments, the group of the Formula (i) is of the formula:

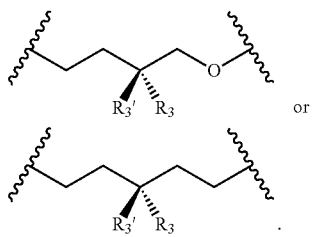

In certain embodiments, the group of the Formula (ii) is of the formula:

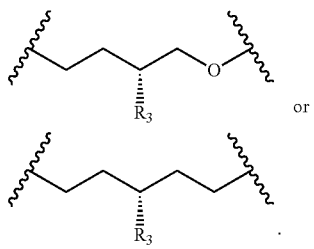

As generally defined above, each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl; or $R_3$ and $R_3'$ are joined to form =O.

In certain embodiments, $R_3$ is hydrogen. In certain embodiments, $R_3'$ is hydrogen. In certain embodiments, $R_3$ is hydrogen and $R_3'$ is a non-hydrogen group. In certain embodiments, $R_3'$ is hydrogen and $R_3$ is a non-hydrogen group. In certain embodiments, however, neither $R_3$ nor $R_3'$ is hydrogen.

In certain embodiments, $R_3$ and $R_3'$ are joined to form =O.

In certain embodiments, $R_3$ and $R_3'$ are the same group. In certain embodiments, $R_3$ and $R_3'$ are different groups.

In certain embodiments, $R_3$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3$ is —O(CO)$R_8$. In certain embodiments, $R_3$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_3$ is —O(CO)$R_8$, and $R_8$ is —(CH$_2$)$_q$CH$_3$ wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_3$ is —OH or substituted hydroxyl. In certain embodiments, $R_3$ is substituted hydroxyl. In certain embodiments, $R_3$ is —OH.

In certain embodiments, $R_3'$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3'$ is —O(CO)$R_8$. In certain embodiments, $R_3'$ is —O(CO)$R_8$, and $R_8$ is optionally substituted $C_{1-20}$alkyl, e.g., optionally substituted $C_{1-15}$alkyl, optionally substituted $C_{1-10}$alkyl, optionally substituted $C_{1-8}$alkyl, optionally substituted $C_{1-6}$alkyl, optionally substituted $C_{1-5}$alkyl, optionally substituted $C_{1-4}$alkyl, optionally substituted $C_{1-3}$alkyl, or optionally substituted $C_{1-2}$alkyl. In certain embodiments, $R_3'$ is —O(CO)$R_8$, and $R_8$ is —(CH$_2$)$_q$CH$_3$ wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_3'$ is —OH or substituted hydroxyl. In certain embodiments, $R_3'$ is substituted hydroxyl. In certain embodiments, $R_3'$ is —OH.

In certain embodiments, $R_3$ is halogen, e.g., selected from fluoro, chloro, bromo, and iodo. In certain embodiments, $R_3'$ is halogen, e.g., selected from fluoro, chloro, bromo, and iodo. In certain embodiments, $R_3$ is halogen and $R_3'$ is halogen, e.g., each independently selected from fluoro, chloro, bromo, and iodo. In certain embodiments, both $R_3$ and $R_3'$ are fluoro.

In certain embodiments, y is 0; and x is 1. In certain embodiments, y is 0; and x is 0. In certain embodiments, y is 1; and x is 1. In certain embodiments, y is 1; and x is 0. In certain embodiments, y is 2; and x is 0. In certain embodiments, y is 2; and x is 1.

As defined generally above, B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl.

In certain embodiments, B is hydrogen.

In certain embodiments, B is optionally substituted $C_{1-30}$alkyl. In certain embodiments, B is optionally substituted $C_{2-30}$alkenyl. In certain embodiments, B is optionally substituted $C_{2-30}$alkynyl.

In certain embodiments, B is optionally substituted $C_{3-7}$carbocyclyl, e.g., optionally substituted cyclohexyl. In certain embodiments, B is optionally substituted 3-8-membered-heterocyclyl. In certain embodiments, B is optionally substituted $C_{6-10}$aryl. In certain embodiments, B is optionally substituted $C_6$aryl (i.e., phenyl). In certain embodiments, B is optionally substituted $C_{10}$aryl (i.e., naphthyl). In certain embodiments, B is optionally substituted 5- to 14-membered heteroaryl. In certain embodiments, B is a monocyclic heteroaryl. In certain embodiments, B is optionally substituted monocyclic 5-membered heteroaryl. In certain embodiments, B is optionally substituted thienyl, e.g., optionally substituted 2-thienyl or optionally substituted 3-thienyl. In certain embodiments, B is 3-(2-methyl)thienyl, 4-(2-methyl)thienyl, 2-(5-methyl)thienyl, 3-(2-chloro)thienyl, 2-(4-bromo)thienyl, 2-(5-bromo)thienyl, 3-(2,5-dichloro)thienyl, or 2-(3-chloro)thienyl. In certain embodiments, B is optionally substituted furanyl, e.g., optionally substituted 2-furanyl or optionally substituted 3-furanyl. In certain embodiments, B is a bicyclic heteroaryl. In certain embodiments, B is an optionally substituted 5,6-bicyclic heteroaryl. In certain embodiments, B is 2-benzofuranyl. In certain embodiments, B is 2-benzothienyl. See, for example, U.S. Pat. No. 5,834,498, the contents of which are incorporated herein by reference.

For example, in certain embodiments, B is an optionally substituted phenyl of the Formula (viii):

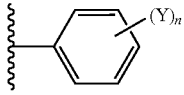
(viii)

wherein:

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino; and n is 0 or an integer of from 1 to 5, inclusive.

In certain embodiments, n is 0 or an integer from 1 to 3, inclusive.

In certain embodiments, n is 0 or an integer from 1 to 2, inclusive.

In certain embodiments, n is 0. In certain embodiments, n is 1. In certain embodiments, n is 2. In certain embodiments, n is 3.

For example, in certain embodiments, wherein n is 1, the group of the Formula (viii) is of the formula:

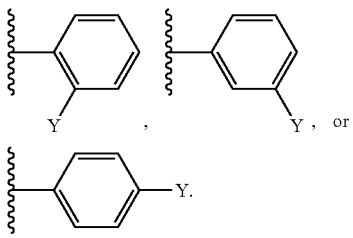

In certain embodiments, wherein n is 2, the group of the Formula (viii) is of the formula:

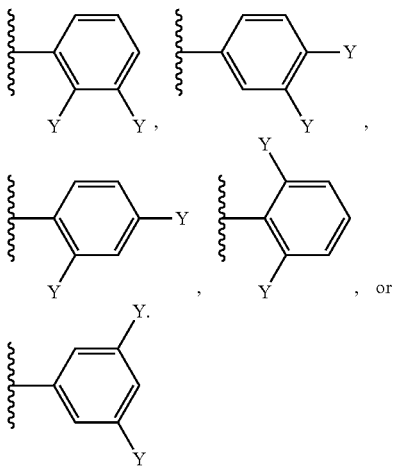

In other embodiments, B is an optionally substituted heteroaryl of the Formula:

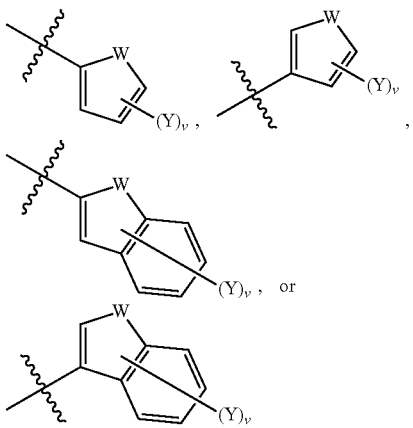

wherein:

W is O or S;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino; and v is 0 or an integer of from 1 to 3, inclusive.

In certain embodiments, v is 0 or an integer from 1 to 2, inclusive. In certain embodiments, v is 0 or 1. In certain embodiments, v is 0. In certain embodiments, v is 1. In certain embodiments, v is 2. In certain embodiments, v is 3.

In certain embodiments, Y is halo, i.e. selected from fluoro, iodo, bromo, or chloro. In certain embodiments Y is chloro. In certain embodiments Y is fluoro.

In certain embodiments, Y is optionally substituted $C_{1-10}$alkyl or $C_{1-10}$perhaloalkyl.

In certain embodiments, Y is optionally substituted $C_{1-10}$alkyl. In certain embodiments, Y is optionally substituted $C_{1-6}$alkyl. In certain embodiments, Y is optionally substituted $C_{1-4}$alkyl. In certain embodiments, Y is optionally substituted $C_{1-3}$alkyl. In certain embodiments, Y is optionally substituted $C_{1-2}$alkyl. In certain embodiments, Y is —$CH_3$, —$CH_2F$, or —$CHF_2$.

In certain embodiments, Y is $C_{1-10}$perhaloalkyl. In certain embodiments, Y is $C_{1-6}$perhaloalkyl. In certain embodiments, Y is $C_{1-4}$perhaloalkyl. In certain embodiments, Y is $C_{1-3}$perhaloalkyl. In certain embodiments, Y is $C_{1-2}$perhaloalkyl. In certain embodiments, Y is —$CF_3$, —$CF_2Cl$, or —$CFCl_2$.

As generally defined above, Z is =O, =S, or =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms.

In certain embodiments, Z is =O.

In certain embodiments, Z is =S.

In certain embodiments, Z is =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl. In certain embodiments, Z is =$NR_Z$ and $R_Z$ is hydrogen.

In certain embodiments, Z represents two hydrogen atoms.

As generally defined above, X is —$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(=O)$R_5$, or —C(=O)$OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring.

In certain embodiments, X is —$OR_4$. In certain embodiments, X is —$OR_4$, and $R_4$ is hydrogen. In certain embodiments, X is —$OR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, wherein $R_4$ is —C(=O)$R_5$, or —C(=O)$OR_5$.

In certain embodiments, X is —$OR_4$, and $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, and $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$. In certain embodiments, X is —$SR_4$, and $R_4$ is hydrogen. In certain embodiments, X is —$SR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, wherein $R_4$ is —C(=O)$R_5$, or —C(=O)$OR_5$.

In certain embodiments, X is —$SR_4$, and $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, and $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$. In certain embodiments, X is —$N(R_4)_2$ and at least one $R_4$ group is hydrogen. In certain embodiments, X is —$N(R_4)_2$ and neither of the two $R_4$ groups are hydrogen. In certain embodiments, X is —$N(R_4)_2$ and at least one $R_4$ is optionally substituted $C_{1-20}$alkyl, optionally substituted $C_{2-20}$alkenyl, or optionally substituted $C_{2-20}$alkynyl. In certain embodiments, X is —$N(R_4)_2$ and at least one $R_4$ is optionally substituted $C_{1-10}$alkyl, optionally substituted $C_{2-10}$alkenyl, or optionally substituted $C_{2-10}$alkynyl. In certain embodiments, X is —$N(R_4)_2$ and at least one $R_4$ is optionally substituted $C_{1-6}$alkyl, e.g., $C_{1-3}$alkyl, $C_{3-4}$alkyl, or $C_{4-6}$alkyl. In certain embodiments, X is —$N(R_4)_2$ and at least one $R_4$ is optionally substituted $C_{2-6}$alkenyl, e.g., $C_{2-3}$alkenyl, $C_{3-4}$alkenyl, or $C_{4-6}$alkenyl. In certain embodiments, X is —$N(R_4)_2$ and at least one $R_4$ is optionally substituted $C_{2-6}$alkynyl, e.g., $C_{2-3}$alkynyl, $C_{3-4}$alkynyl, or $C_{4-6}$alkynyl. However, in certain embodiments, X is not —NH(iPr).

In certain embodiments, X is —$N(R_4)_2$ and at least one $R_4$ is —C(=O)$R_5$, or —C(=O)$OR_5$.

In certain embodiments, X is —$N(R_4)_2$ and at least one $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$ and at least one $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In other embodiments, X is —N(R$_4$)$_2$ and the two R$_4$ groups are joined to form an optionally substituted 3-8-membered-heterocyclyl or optionally substituted 5-14-membered-heteroaryl ring.

In certain embodiments, wherein X is —OR$_4$, —SR$_4$, or —N(R$_4$)$_2$, any one of R$_4$ or R$_5$ is optionally substituted C$_{1-30}$alkyl (e.g., C$_{1-10}$alkyl, C$_{1-6}$alkyl, C$_{1-3}$alkyl, C$_{7-30}$alkyl, C$_{10-30}$alkyl, C$_{7-25}$alkyl, C$_{10-25}$alkyl, C$_{15-25}$alkyl). In certain embodiments, any one of R$_4$ or R$_5$ is optionally substituted C$_{2-30}$alkenyl (e.g., C$_{2-10}$alkenyl, C$_{2-6}$alkenyl, C$_{1-3}$alkenyl, C$_{7-30}$alkenyl, C$_{10-30}$alkenyl, C$_{7-25}$alkenyl, C$_{10-25}$alkenyl, C$_{15-25}$alkenyl). In certain embodiments, any one of R$_4$ or R$_5$ is optionally substituted C$_{2-30}$alkynyl (e.g., alkynyl, C$_{2-6}$alkynyl, C$_{1-3}$alkynyl, C$_{7-30}$alkynyl, C$_{10-30}$alkynyl, C$_{7-25}$alkynyl, C$_{10-25}$alkynyl, C$_{15-25}$alkynyl).

In any of the above embodiments, when R$_4$ or R$_5$ are defined as a C$_{7-30}$alkyl or C$_{7-30}$alkenyl groups, such groups may also be referred to as "lipid tails." Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., C$_{7-12}$ alkyl or C$_{7-12}$ alkenyl), long (i.e., with tails greater than 12 carbons and up to 22 carbons, e.g., C$_{13-22}$ alkyl or C$_{13-22}$ alkenyl), or very long (i.e., with tails greater than 22 carbons, e.g., C$_{23-30}$ alkyl or C$_{23-30}$ alkenyl).

Exemplary unsaturated lipid tails include, but are not limited to:

Myristoleic —(CH$_2$)$_7$CH═CH(CH$_2$)$_3$CH$_3$,
Palmitoleic —(CH$_2$)$_7$CH═CH(CH$_2$)$_5$CH$_3$,
Sapienic —(CH$_2$)$_4$CH═CH(CH$_2$)$_8$CH$_3$,
Oleic —(CH$_2$)$_7$CH═CH(CH$_2$)$_7$CH$_3$,
Linoleic —(CH$_2$)$_7$CH═CHCH$_2$CH═CH(CH$_2$)$_4$CH$_3$,
α-Linolenic —(CH$_2$)$_7$CH═CHCH$_2$CH═CHCH$_2$CH═CHCH$_2$CH$_3$,
Arachidonic —(CH$_2$)$_3$CH═CHCH$_2$CH═CHCH$_2$CH═CHCH$_2$CH═CH(CH$_2$)$_4$CH$_3$,
Eicosapentaenoic —(CH$_2$)$_3$CH═CHCH$_2$CH═CHCH$_2$CH═CHCH$_2$CH═CHCH$_2$CH$_3$,
Erucic —(CH$_2$)$_{11}$CH═CH(CH$_2$)$_7$CH$_3$, and
Docosahexaenoic —(CH$_2$)$_2$CH═CHCH$_2$CH═CHCH$_2$CH═CHCH$_2$CH═CHCH$_2$CH═CHCH$_2$CH═CH—CH$_2$CH$_3$.

Exemplary saturated lipid tails include, but are not limited to:

Lauric —(CH$_2$)$_{10}$CH$_3$,
Myristic —(CH$_2$)$_{12}$CH$_3$,
Palmitic —(CH$_2$)$_{14}$CH$_3$,
Stearic —(CH$_2$)$_{16}$CH$_3$,
Arachidic —(CH$_2$)$_{18}$CH$_3$,
Behenic —(CH$_2$)$_{20}$CH$_3$,
Lignoceric —(CH$_2$)$_{22}$CH$_3$, and
Cerotic —(CH$_2$)$_{24}$CH$_3$.

In certain embodiments of Formula (I), the compound is of Formula (I-a):

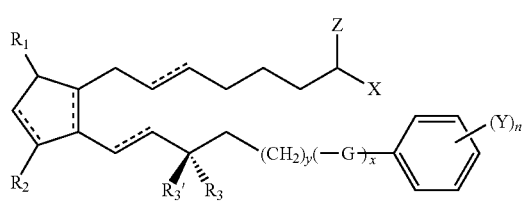

(I-a)

or a pharmaceutically acceptable salt, hydrate, solvate, stereoisomer, polymorph, tautomer, isotopically enriched derivative, or prodrug thereof; wherein R$_1$, R$_2$, Z, and X are as defined herein;

each instance of ═══ independently represents a single bond or a double bond which can be in the cis or trans configuration;

each instance of R$_3$ and R$_3$' is independently hydrogen, halogen, —OH, substituted hydroxyl, or —O(CO)R$_8$, wherein R$_8$ is optionally substituted C$_{1-20}$alkyl, optionally substituted C$_{2-20}$alkenyl, optionally substituted C$_{2-20}$alkynyl, or —(CH$_2$)$_m$R$_9$ wherein m is 0 or an integer between 1-10, inclusive, and R$_9$ is optionally substituted C$_{3-7}$carbocyclyl, optionally substituted C$_{6-10}$aryl, or optionally substituted 5-14-membered-heteroaryl, or R$_3$ and R$_3$' are joined to form ═O;

Y is selected from the group consisting of optionally substituted C$_{1-10}$alkyl, C$_{1-10}$perhaloalkyl, optionally substituted C$_{2-10}$alkenyl, optionally substituted C$_{2-10}$alkynyl, halo, nitro, cyano, thiol, substituted thiol, hydroxyl, substituted hydroxyl, amino, monosubstituted amino, and disubstituted amino;

G is —O— or —S—;
y is 0, 1, or 2;
x is 0 or 1; and
n is 0 or an integer of from 1 to 5, inclusive.

In certain embodiments of Formula (I-a), wherein R$_3$' is hydrogen, the compound is of Formula (I-b):

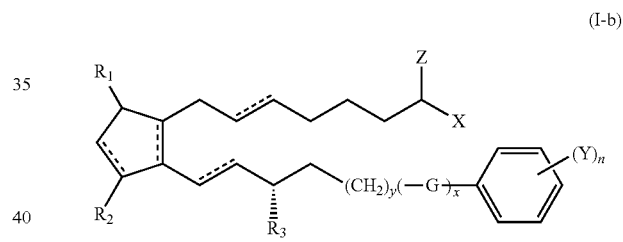

(I-b)

or a pharmaceutically acceptable salt, hydrate, solvate, stereoisomer, polymorph, tautomer, isotopically enriched derivative, or prodrug thereof; wherein ═══, R$_1$, R$_2$, R$_3$, Z, X, Y, G, y, x, and n are as defined herein.

In certain embodiments of Formula (I-a), wherein R$_3$ is hydrogen, the compound is of Formula (I-c):

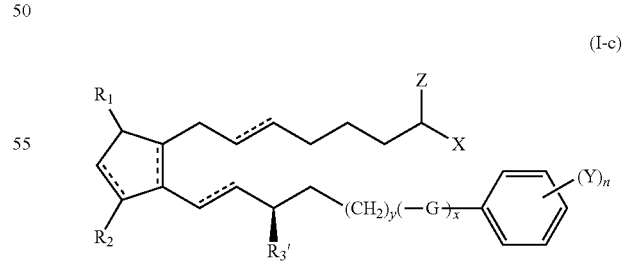

(I-c)

or a pharmaceutically acceptable salt, hydrate, solvate, stereoisomer, polymorph, tautomer, isotopically enriched derivative, or prodrug thereof; wherein ═══, R$_1$, R$_2$, R$_3$', Z, X, Y, G, y, x, and n are as defined herein.

In certain embodiments, G is —O—. In certain embodiments, G is —S—.

In certain embodiments of Formula (I-a), wherein G is
—O—, provided is a compound of Formula (I-a1):

(I-a1)

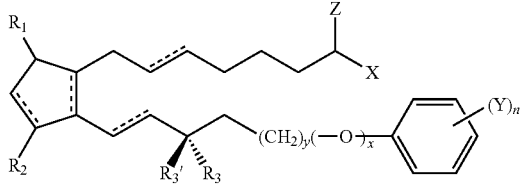

or a pharmaceutically acceptable salt, hydrate, solvate, stereoisomer, polymorph, tautomer, isotopically enriched derivative, or prodrug thereof; wherein $R_1$, $R_2$, $Z$, and $X$ are as defined herein; wherein ══════, $R_1$, $R_2$, $R_3$, $Z$, $X$, $Y$, y, x, and n are as defined herein.

In certain embodiments of Formula (I-b), wherein G is —O—, the compound is of Formula (I-b1):

(I-b1)

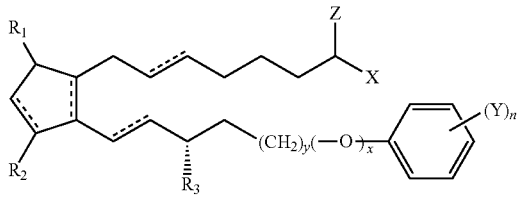

or a pharmaceutically acceptable salt, hydrate, solvate, stereoisomer, polymorph, tautomer, isotopically enriched derivative, or prodrug thereof; wherein ══════, $R_1$, $R_2$, $R_3$, $Z$, $X$, $Y$, y, x, and n are as defined herein.

In certain embodiments of Formula (I-c), wherein G is —O—, the compound is of Formula (I-c1):

(I-c1)

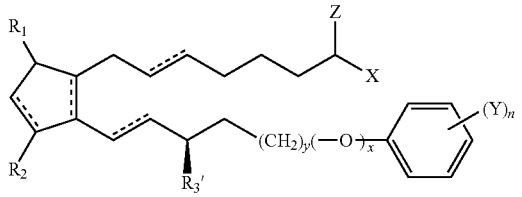

or a pharmaceutically acceptable salt, hydrate, solvate, stereoisomer, polymorph, tautomer, isotopically enriched derivative, or prodrug thereof; wherein ══════, $R_1$, $R_2$, $R_3'$, $Z$, $X$, $Y$, y, x, and n are as defined herein.

In certain embodiments of Formula (I-a), wherein G is —S—, provided is a compound of Formula (I-a2):

(I-a2)

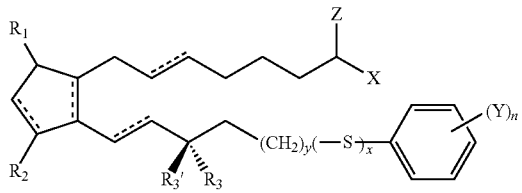

or a pharmaceutically acceptable salt, hydrate, solvate, stereoisomer, polymorph, tautomer, isotopically enriched derivative, or prodrug thereof; wherein $R_1$, $R_2$, $Z$, and $X$ are as defined herein; wherein ══════, $R_1$, $R_2$, $R_3'$, $Z$, $X$, $Y$, y, x, and n are as defined herein.

In certain embodiments of Formula (I-b), wherein G is —S—, the compound is of Formula (I-b2):

(I-b2)

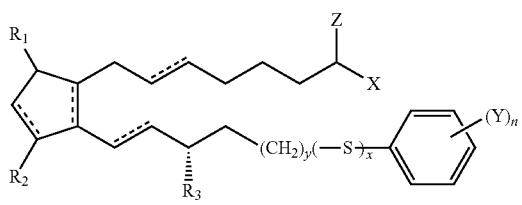

or a pharmaceutically acceptable salt, hydrate, solvate, stereoisomer, polymorph, tautomer, isotopically enriched derivative, or prodrug thereof; wherein ══════, $R_1$, $R_2$, $R_3$, $Z$, $X$, $Y$, y, x, and n are as defined herein.

In certain embodiments of Formula (I-c), wherein G is —S—, the compound is of Formula (I-c2):

(I-c2)

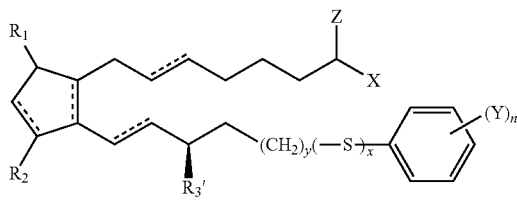

or a pharmaceutically acceptable salt, hydrate, solvate, stereoisomer, polymorph, tautomer, isotopically enriched derivative, or prodrug thereof; wherein ══════, $R_1$, $R_2$, $R_3$, $Z$, $X$, $Y$, y, x, and n are as defined herein.

In certain embodiments, the compound of Formula (I-a) has the following stereochemistry, also referred to herein as a compound of Formula (I-d):

(I-d)

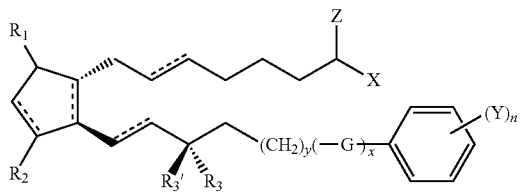

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3'$, Z, X, Y, G, X, y, x, and n are as defined herein.

In certain embodiments of Formula (I-d), wherein $R_3'$ is hydrogen, the compound is of Formula (I-e):

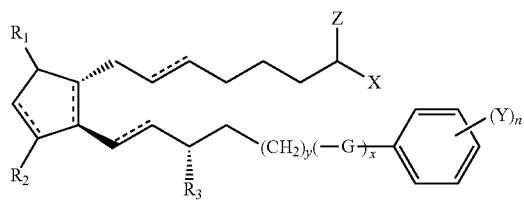

(I-e)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3$, $R_3'$, Z, Y, G, X, y, x, and n are as defined herein.

In certain embodiments of Formula (I-d), wherein $R_3'$ is hydrogen, the compound is of Formula (I-e):

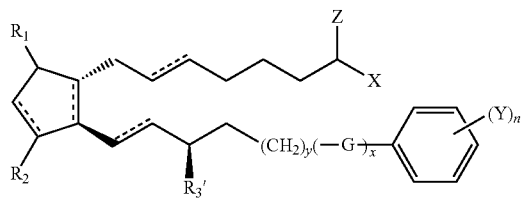

(I-f)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3'$, Z, X, Y, G, y, x, and n are as defined herein.

In certain embodiments, G is —O—. In certain embodiments, G is —S—.

In certain embodiments of Formula (I-d), wherein G is —O—, the compound is of Formula (I-d1):

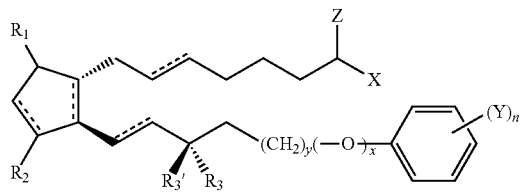

(I-d1)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3$, $R_3'$, Z, Y, X, y, x, and n are as defined herein.

In certain embodiments of Formula (I-e), wherein G is —O—, the compound is of Formula (I-e1):

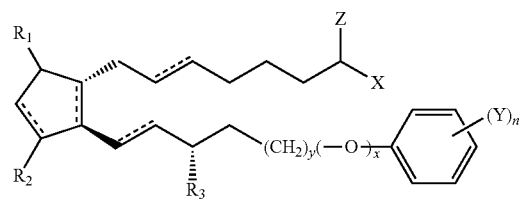

(I-e1)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3$, Z, X, Y, y, x, and n are as defined herein.

In certain embodiments of Formula (I-f), wherein G is —O—, the compound is of Formula (I-f1):

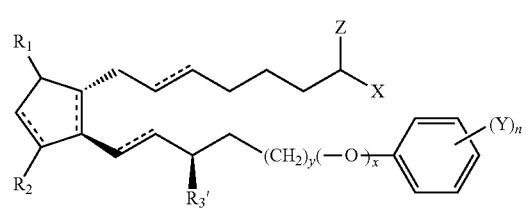

(I-f1)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3'$, Z, X, Y, y, x, and n are as defined herein.

In certain embodiments of Formula (I-d), wherein G is —S—, the compound is of Formula (I-d2):

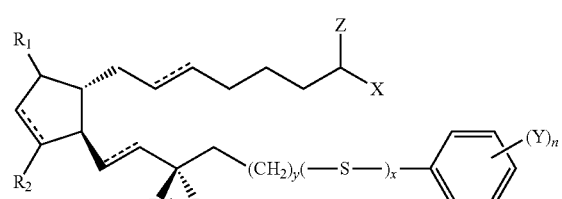

(I-d2)

or a pharmaceutically acceptable salt, hydrate, solvate, stereoisomer, polymorph, tautomer, isotopically enriched derivative, or prodrug thereof; wherein ╌╌╌, $R_1$, $R_2$, $R_3$, $R_3'$, Z, Y, X, y, x, and n are as defined herein.

In certain embodiments of Formula (I-e), wherein G is —S—, the compound is of Formula (I-e2):

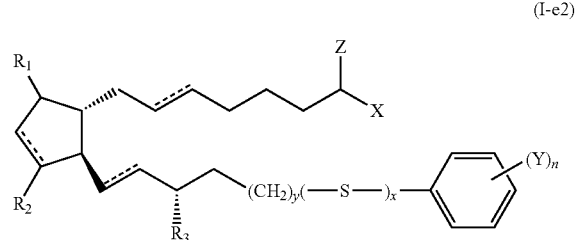

(I-e2)

or a pharmaceutically acceptable salt, hydrate, solvate, stereoisomer, polymorph, tautomer, isotopically enriched derivative, or prodrug thereof; wherein ------, $R_1$, $R_2$, $R_3$, Z, X, Y, y, x, and n are as defined herein.

In certain embodiments of Formula (I-f), wherein G is —S—, the compound is of Formula (I-f2):

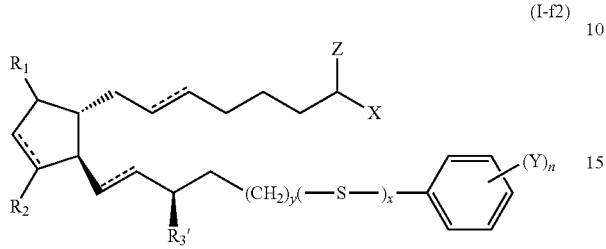

(I-f2)

or a pharmaceutically acceptable salt, hydrate, solvate, stereoisomer, polymorph, tautomer, isotopically enriched derivative, or prodrug thereof; wherein ------, $R_1$, $R_2$, $R_3'$, Z, X, Y, y, x, and n are as defined herein.

In certain embodiments, Z is =O. In certain embodiments, each ------ represents a single bond. In certain embodiments, each endocyclic ------ represents a single bond. In certain embodiments at least one exocyclic ------ represents a cis-double bond. In certain embodiments, each instance of $R_1$ and $R_2$ is —OH. In certain embodiments, each instance of $R_1$ and $R_2$ is —O(CO)$R_6$. In certain embodiments, one of $R_1$ and $R_2$ is —OH, and the other one is —O(CO)$R_6$. In certain embodiments, one of $R_3$ and $R_3.R_3'$ is —O(CO)$R_8$, and the other is hydrogen. In certain embodiments, $R_1$ is —OH, $R_2$ is —O(CO)$R_6$, one of $R_3$ and $R_3.R_3'$ is —OH, and the other is hydrogen. In certain embodiments, $R_2$ is —OH, $R_1$ is —O(CO)$R_6$, one of $R_3$ and $R_3.R_3'$ is —OH, and the other is hydrogen. In certain embodiments, each of $R_1$ and $R_2$ is —OH, and one of $R_3$ and $R_3.R_3'$ is —O(CO)$R_8$, and the other is hydrogen. In certain embodiments, each instance of $R_1$ and $R_2$ is —O(CO)$R_6$, and one of $R_3$ and $R_3.R_3'$ is —O(CO)$R_8$, and the other is hydrogen. In certain embodiments, —O(CO)$R_6$ and —O(CO)$R_8$ attached to the compound are the same group. In certain embodiments, —O(CO)$R_6$ and —O(CO)$R_8$ attached to the compound are different groups.

In certain embodiments of Formula (I-d), wherein Z is =O, each endocyclic ------ represents a single bond, and at least one exocyclic ------ represents a cis-double bond, provided is a compound of Formula (I-d3) having the following stereochemistry:

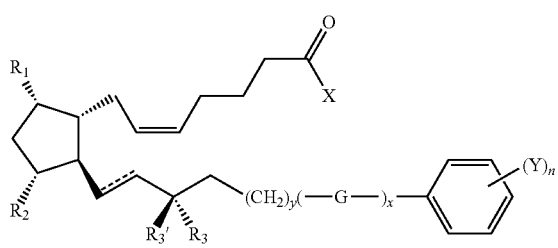

(I-d3)

or a pharmaceutically acceptable salt, hydrate, solvate, stereoisomer, polymorph, tautomer, isotopically enriched derivative, or prodrug thereof; wherein ------, $R_1$, $R_2$, $R_3$, $R_3'$, G, Y, X, y, x, and n are as defined herein.

In certain embodiments of Formula (I-e), wherein Z is =O, each endocyclic ------ represents a single bond, and at least one exocyclic ------ represent a cis-double bond, provided is a compound of Formula (I-e3) having the following stereochemistry:

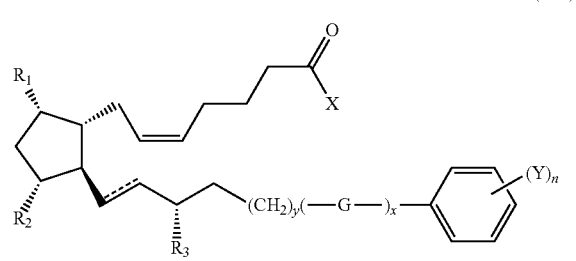

(I-e3)

or a pharmaceutically acceptable salt, hydrate, solvate, stereoisomer, polymorph, tautomer, isotopically enriched derivative, or prodrug thereof; wherein ------, $R_1$, $R_2$, $R_3$, G, X, Y, y, x, and n are as defined herein.

In certain embodiments of Formula (I-f), wherein Z is =O, each endocyclic ------ represents a single bond, and at least one exocyclic ------ represents a cis-double bond, provided is a compound of Formula (I-f3) having the following stereochemistry:

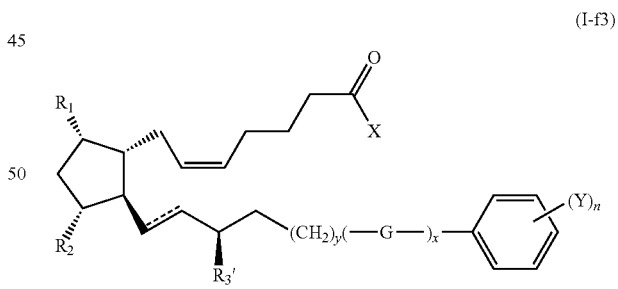

(I-f3)

or a pharmaceutically acceptable salt, hydrate, solvate, stereoisomer, polymorph, tautomer, isotopically enriched derivative, or prodrug thereof; wherein ------, $R_1$, $R_2$, $R_3'$, G, X, Y, y, x, and n are as defined herein.

In certain embodiments of Formula (I-d3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, provided is a compound of Formula (I-d4), (I-d5), and (I-d6) having the following stereochemistry:

(I-d4)
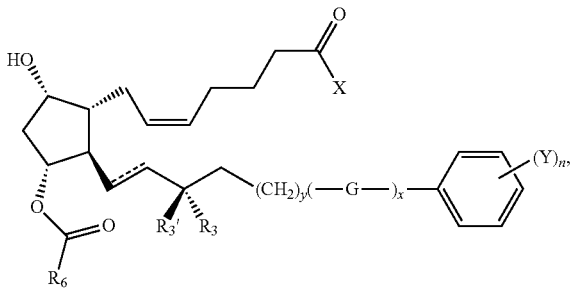

(I-d5)
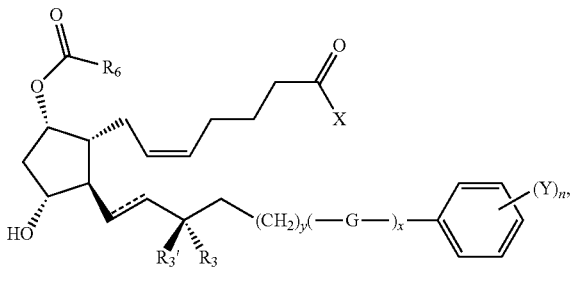

(I-d6)
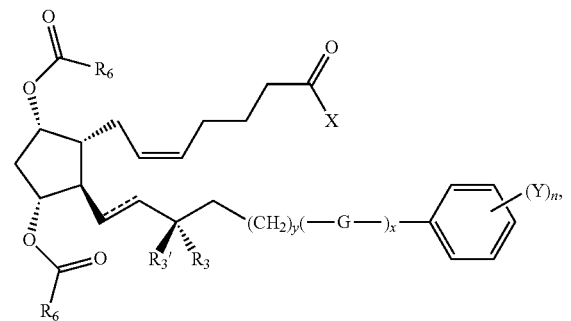

or a pharmaceutically acceptable salt, hydrate, solvate, stereoisomer, polymorph, tautomer, isotopically enriched derivative, or prodrug thereof; wherein ------, $R_6$, $R_3$, $R_3'$, G, Y, X, y, x, and n are as defined herein.

In certain embodiments of Formula (I-d3), wherein $R_3$ is —O(CO)$R_8$ or $R_3'$ is —O(CO)$R_8$, provided is a compound of Formula (I-d7) and (I-d8) having the following stereochemistry:

(I-d7)
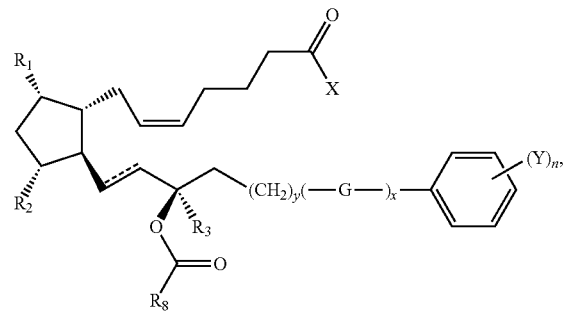

(I-d8)
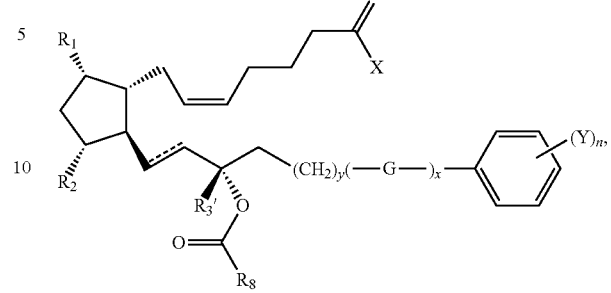

or a pharmaceutically acceptable salt, hydrate, solvate, stereoisomer, polymorph, tautomer, isotopically enriched derivative, or prodrug thereof; wherein ------, $R_1$, $R_2$, $R_3$, $R_3'$, $R_8$, G, Y, X, y, x, and n are as defined herein.

In certain embodiments of Formula (I-d3), wherein $R_1$ and $R_2$ are each —OH and $R_3$ is —O(CO)$R_8$, or wherein $R_1$ and $R_2$ are each —OH and $R_3'$ is —O(CO)$R_8$, provided is a compound of Formula (I-d9) and (I-d10) having the following stereochemistry:

(I-d9)
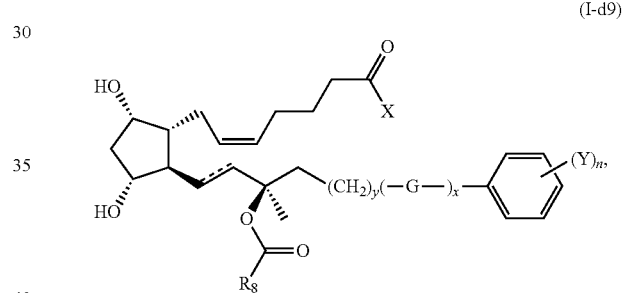

(I-d10)
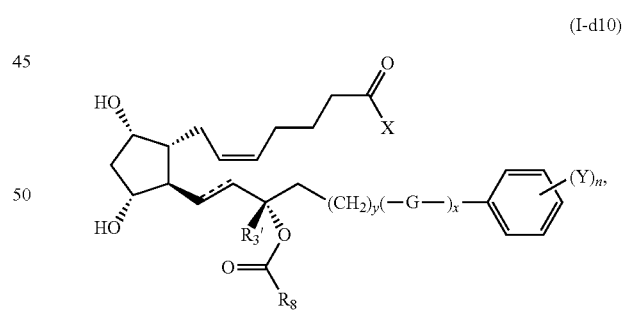

or a pharmaceutically acceptable salt, hydrate, solvate, stereoisomer, polymorph, tautomer, isotopically enriched derivative, or prodrug thereof; wherein ------, $R_3$, $R_3'$, $R_8$, G, Y, X, y, x, and n are as defined herein.

In certain embodiments of Formula (I-e3), wherein $R_1$ is —OH and $R_2$ is —O(CO)$R_6$, or wherein $R_2$ is —OH and $R_1$ is —O(CO)$R_6$, or wherein both $R_1$ and $R_2$ are —O(CO)$R_6$, and $R_3'$ is hydrogen and $R_3$ is —OH, provided is a compound of Formula (I-d11), (I-d12), and (I-d13) having the following stereochemistry:

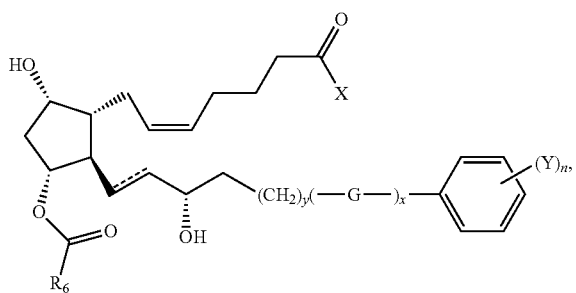

(I-d11)

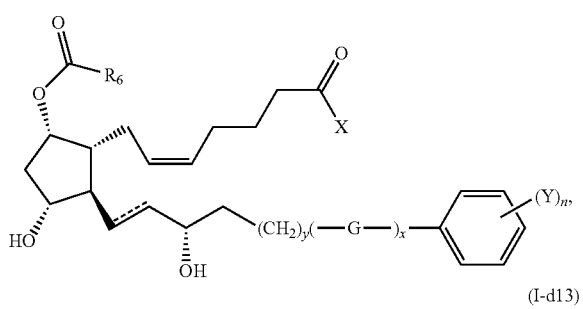

(I-d12)

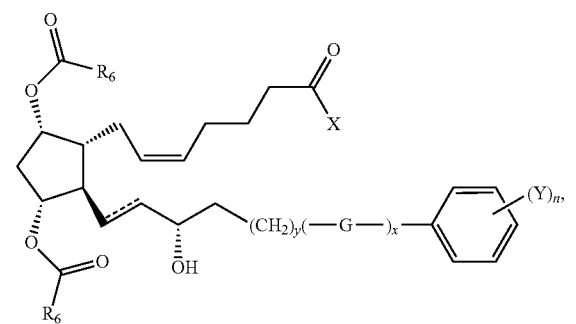

(I-d13)

or a pharmaceutically acceptable salt, hydrate, solvate, stereoisomer, polymorph, tautomer, isotopically enriched derivative, or prodrug thereof; wherein ======, $R_6$, $R_3$, $R_3'$, G, Y, X, y, x, and n are as defined herein.

In certain embodiments of Formula (I-d8), wherein each of $R_1$ and $R_2$ are —O(CO)$R_6$ and $R_3'$ is hydrogen, provided is a compound of Formula (I-d14) having the following stereochemistry:

(I-d14)

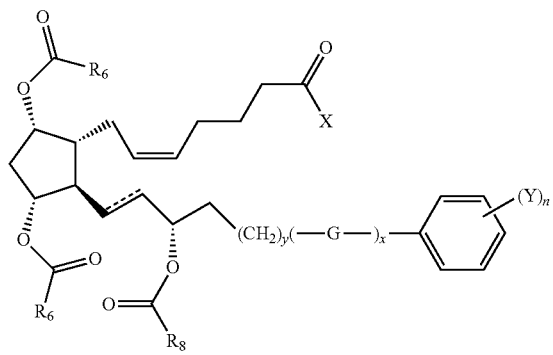

or a pharmaceutically acceptable salt, hydrate, solvate, stereoisomer, polymorph, tautomer, isotopically enriched derivative, or prodrug thereof; wherein ======, $R_6$, $R_8$, G, Y, X, y, x, and n are as defined herein.

In certain embodiments of Formula (I-d2), wherein Z is =O, each instance of $R_1$ and $R_2$ is —OH, and each ====== represents a single bond, provided is a compound of Formula (I-g):

(I-g)

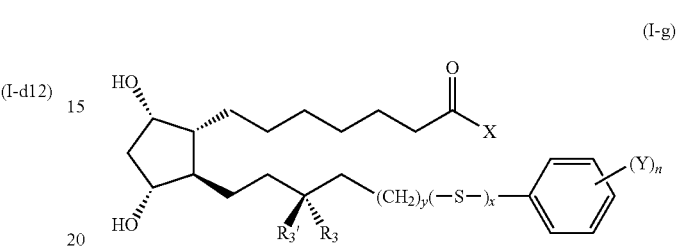

or a pharmaceutically acceptable salt, hydrate, solvate, stereoisomer, polymorph, tautomer, isotopically enriched derivative, or prodrug thereof; wherein X, Y, $R_3$, $R_3'$, y, x, and n are as defined herein.

In certain embodiments of Formula (I-d1), wherein each instance of $R_1$ and $R_2$ is —OH, and Z is =O, provided is a compound of Formula (I-h):

(I-h)

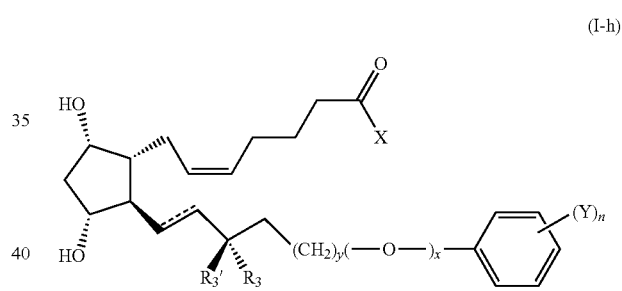

or a pharmaceutically acceptable salt, hydrate, solvate, stereoisomer, polymorph, tautomer, isotopically enriched derivative, or prodrug thereof; wherein ======, $R_3$, $R_3'$, Y, X, y, x, and n are as defined herein.

In certain embodiments of Formula (I-h), wherein $R_3'$ is hydrogen, provided is a compound of Formula (I-i):

(I-i)

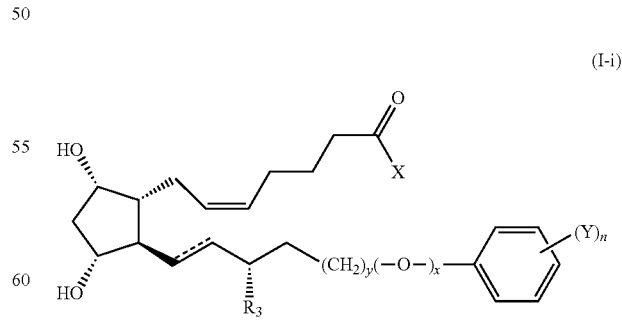

or a pharmaceutically acceptable salt, hydrate, solvate, stereoisomer, polymorph, tautomer, isotopically enriched derivative, or prodrug thereof; wherein ======, $R_3$, Y, X, y, x, and n are as defined herein.

In certain embodiments of Formula (I-i), wherein $R_3$ is —OH, provided is a compound of Formula (I-j):

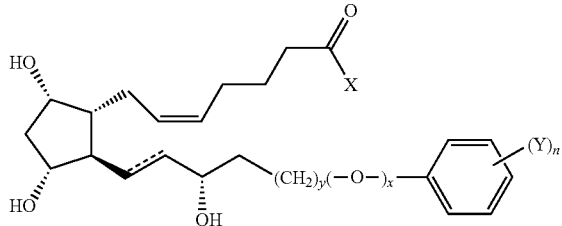
(I-j)

or a pharmaceutically acceptable salt, hydrate, solvate, stereoisomer, polymorph, tautomer, isotopically enriched derivative, or prodrug thereof; wherein Y, X, y, x, and n are as defined herein.

In certain embodiments of Formula (I-h), wherein $R_3$ is F and $R_3'$ is F, provided is a compound of Formula (I-k):

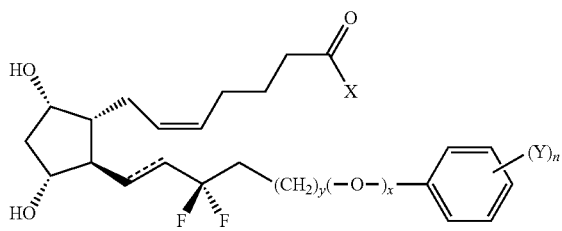
(I-k)

or a pharmaceutically acceptable salt, hydrate, solvate, stereoisomer, polymorph, tautomer, isotopically enriched derivative, or prodrug thereof; wherein ------, Y, X, y, x, and n are as defined herein.

In certain embodiments of Formula (I-i), wherein $R_3$ is —O(CO)$R_8$, provided is a compound of Formula (I-o):

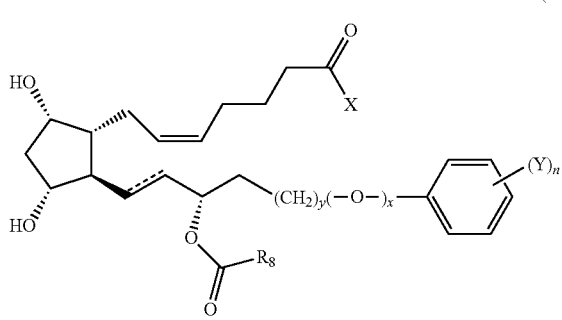
(I-o)

or a pharmaceutically acceptable salt, hydrate, solvate, stereoisomer, polymorph, tautomer, isotopically enriched derivative, or prodrug thereof; wherein $R_8$, Y, X, y, x, and n are as defined herein.

In certain embodiments of Formula (I), the compound of Formula (I-1):

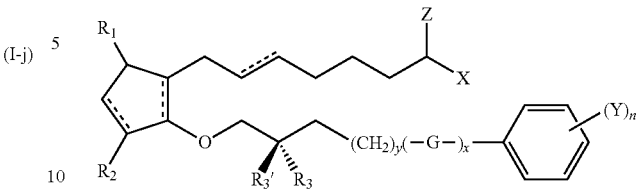
(I-l)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

each instance of ------ independently represents a single bond or a double bond which can be in the cis or trans configuration;

each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form =O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

In certain embodiments of Formula (I-1), wherein Z is =O, and $R_1$ and $R_2$ are each —OH, provided is a compound of Formula (I-m):

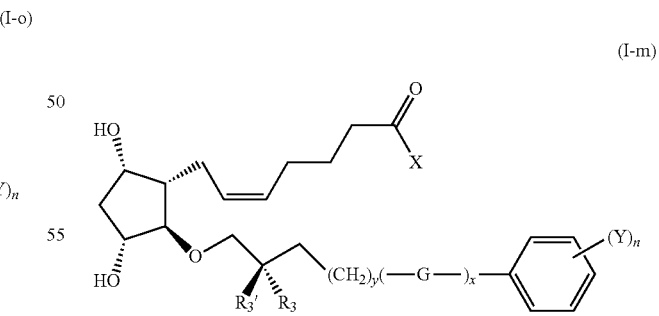
(I-m)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

In certain embodiments of Formula (I-m), wherein $R_3'$ is hydrogen, y is 2 and x is 0, provided is a compound of Formula (I-n):

(I-n)

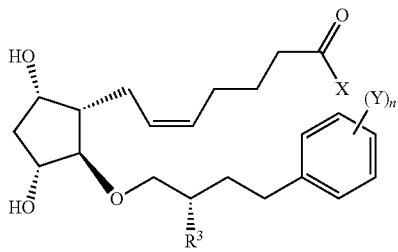

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

As generally defined above, in certain embodiments, provided is a compound of Formula (II):

(II)

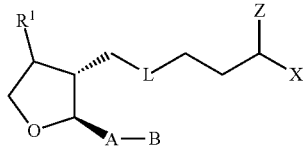

or a pharmaceutically acceptable salt, hydrate, solvate, stereoisomer, polymorph, tautomer, isotopically enriched derivative, or prodrug thereof; wherein A, B, X, Z, L, and $R_1$ are as defined herein are as defined herein.

In certain embodiments, L is a group of the formula

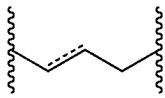

wherein

===== represents a single bond.

In certain embodiments, L is a group of the formula

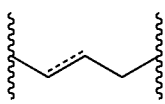

wherein ===== represents a double bond which can be in the cis or trans configuration. In certain embodiments, the double bond is in the cis configuration. In certain embodiments, the double bond is in the trans configuration.

In certain embodiments, L is a group of the formula

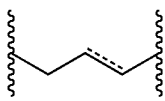

wherein ===== represents a single bond.

In certain embodiments, L is a group of the formula

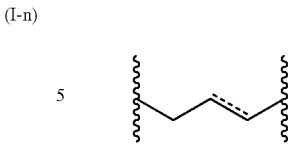

wherein ===== represents a double bond which can be in the cis or trans configuration. In certain embodiments, the double bond is in the cis configuration. In certain embodiments, the double bond is in the trans configuration.

In certain embodiments of Formula (II), the compound of Formula (II-a):

(II-a)

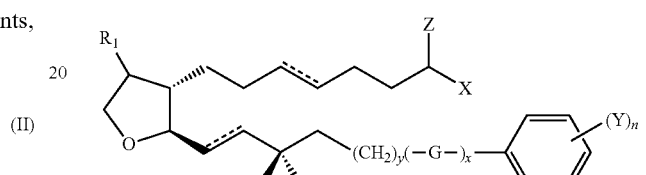

or a pharmaceutically acceptable salt, hydrate, solvate, stereoisomer, polymorph, tautomer, isotopically enriched derivative, or prodrug thereof, wherein =====, $R_1$, Z, X, Y, G, $R_3$, $R_3'$, y, x and n are as defined herein.

In certain embodiments of Formula (II-a), wherein $R_3'$ is hydrogen, the compound is of Formula (II-b):

(II-b)

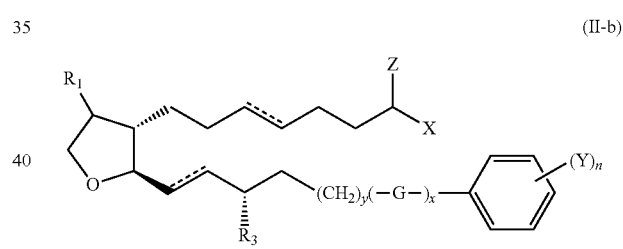

or a pharmaceutically acceptable salt, hydrate, solvate, stereoisomer, polymorph, tautomer, isotopically enriched derivative, or prodrug thereof; wherein =====, $R_1$, $R_3$, Z, X, Y, G, y, x, and n are as defined herein.

In certain embodiments of Formula (II-a), wherein $R_3$ is hydrogen, the compound is of Formula (II-c):

(II-c)

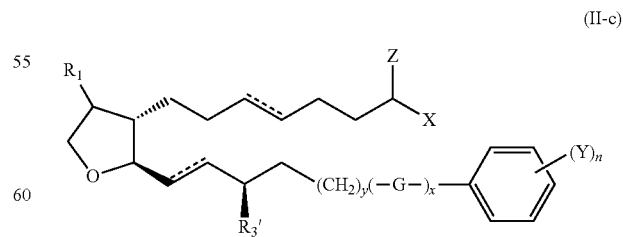

or a pharmaceutically acceptable salt, hydrate, solvate, stereoisomer, polymorph, tautomer, isotopically enriched derivative, or prodrug thereof; wherein =====, $R_1$, $R_2$, $R_3'$, Z, X, Y, G, y, x, and n are as defined herein.

In certain embodiments, G is —O—. In certain embodiments, G is —S—.

In certain embodiments of Formula (II-a), wherein G is —O—, provided is a compound of Formula (II-a1):

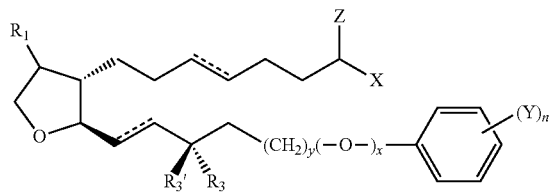

(II-a1)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ------, $R_1$, $R_2$, $R_3'$, Z, X, Y, y, x, and n are as defined herein.

In certain embodiments, Z is =O.

In certain embodiments at least one exocyclic ------ represents a cis-double bond.

For example, in certain embodiments of Formula (II-a1), wherein Z is =O, provided is a compound of Formula (II-d):

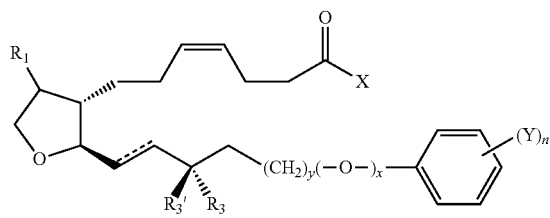

(II-d)

or a pharmaceutically acceptable salt, hydrate, solvate, stereoisomer, polymorph, tautomer, isotopically enriched derivative, or prodrug thereof; wherein ------, $R_1$, $R_3$, $R_3'$, Y, X, y, x, and n are as defined herein.

In certain embodiments of Formula (II-d), wherein $R_1$ is OH, $R_3'$ is hydrogen, $R_3$ is —OH, y is 0, and x is 1, provided is a compound of Formula (II-e):

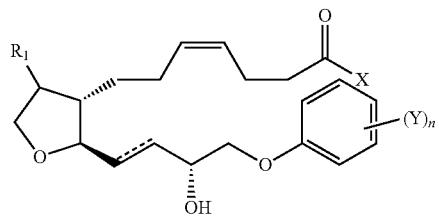

(II-e)

or a pharmaceutically acceptable salt, hydrate, solvate, stereoisomer, polymorph, tautomer, isotopically enriched derivative, or prodrug thereof; wherein ------, Y, X, and n are as defined herein.

Exemplary compounds of Formula (I) include, but are not limited to:

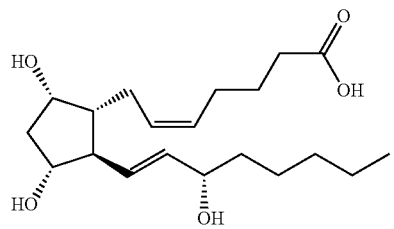 [SMILES: CCCCC[C@H](O)/C=C/[C@@H]1[C@@H](C/C=C\CCCC(=O)O)[C@@H](O)C[C@H]1O]

referred to herein as Prostaglandin F2α;

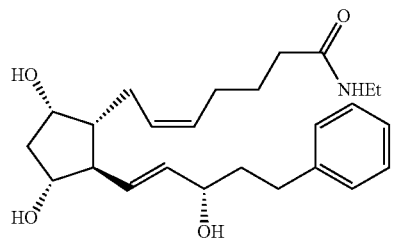

also referred to herein as bimatoprost;

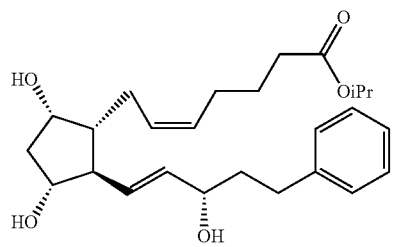 [SMILES: CC(C)OC(=O)CCC/C=C\C[C@@H]1[C@@H](/C=C/[C@@H](O)CCc2ccccc2)[C@H](O)C[C@@H]1O]

also referred to herein as bimatoprost isopropyl ester;

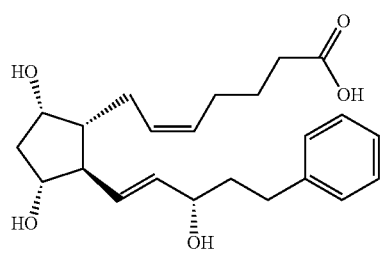 [SMILES: O=C(O)CCC/C=C\C[C@@H]1[C@@H](/C=C/[C@@H](O)CCc2ccccc2)[C@H](O)C[C@@H]1O]

also referred to herein as bimatoprost free acid;

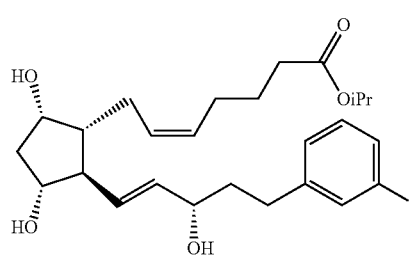

also referred to herein as travoprost;

51

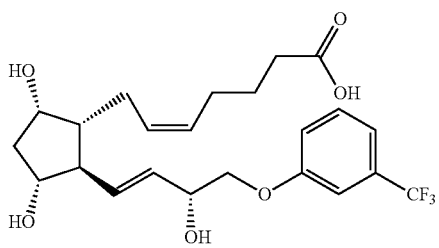 [SMILES: O=C(O)CCC/C=C\C[C@@H]1[C@@H](/C=C/[C@@H](O)COc2cccc(C(F)(F)F)c2)[C@H](O)C[C@@H]1O]

also referred to herein as travoprost free acid or fluprostenol;

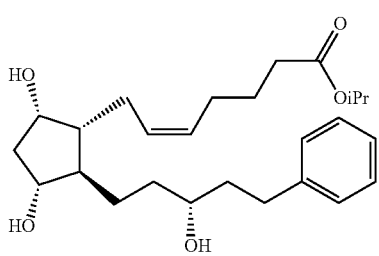 [SMILES: CC(C)OC(=O)CCC/C=C\C[C@@H]1[C@@H](CC[C@@H](O)CCc2ccccc2)[C@H](O)C[C@@H]1O]

also referred to herein as latanoprost;

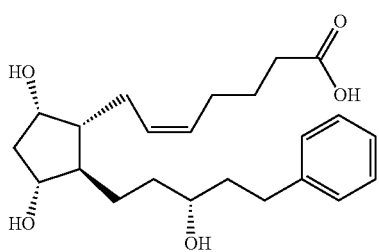 [SMILES: O=C(O)CCC/C=C\C[C@@H]1[C@@H](CC[C@@H](O)CCc2ccccc2)[C@H](O)C[C@@H]1O]

also referred to herein as latanoprost free acid;

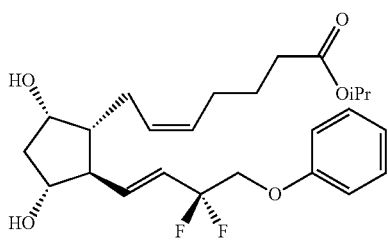

also referred to herein as tafluprost;

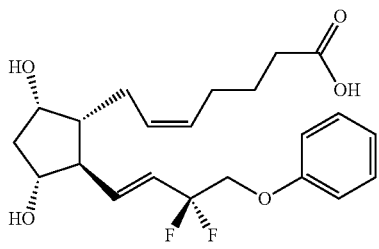

also referred to herein as tafluprost free acid or AFP-172;

52

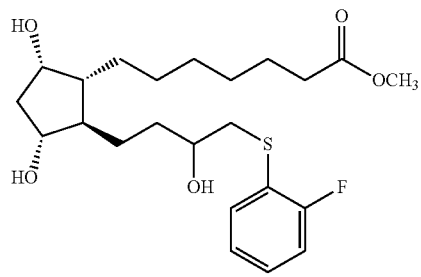 [SMILES: COC(=O)CCCCCC[C@@H]1[C@@H](CCC(O)CSc2ccccc2F)[C@H](O)C[C@@H]1O]

also referred to herein as CAY10509; and

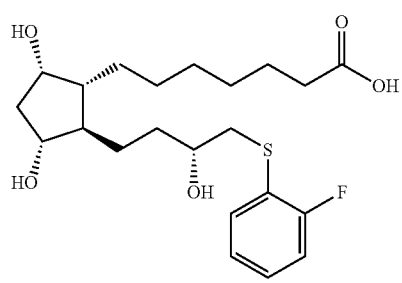 [SMILES: O=C(O)CCCCCC[C@@H]1[C@@H](CC[C@@H](O)CSc2ccccc2F)[C@H](O)C[C@@H]1O]

also referred to herein as CAY10509 free acid;

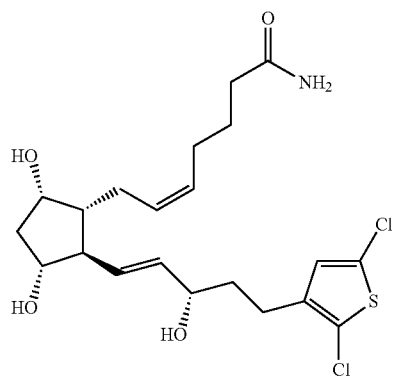 [SMILES: NC(=O)CCC/C=C\C[C@@H]1[C@@H](/C=C/[C@@H](O)CCc2cc(Cl)sc2Cl)[C@H](O)C[C@@H]1O]

also referred to herein as 7-[3α,5α-dihydroxy-2-(3α-hydroxy-5-(3-(2,5-dichloro)thienyl)-1E-pentenyl)cyclopentyl]-5Z-heptenamide;

and 9-, 11-, and/or 15-ester derivatives (e.g., prodrugs) of the above, e.g., of formula:

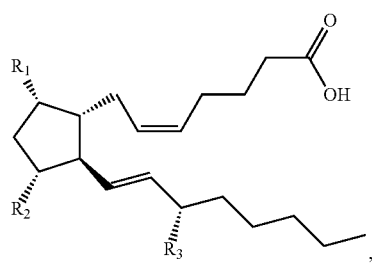

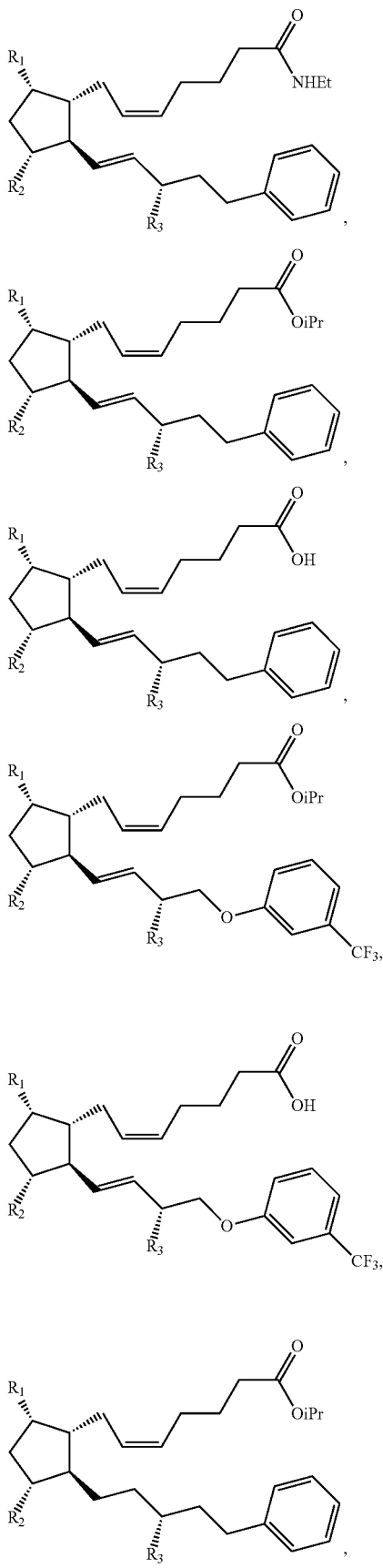

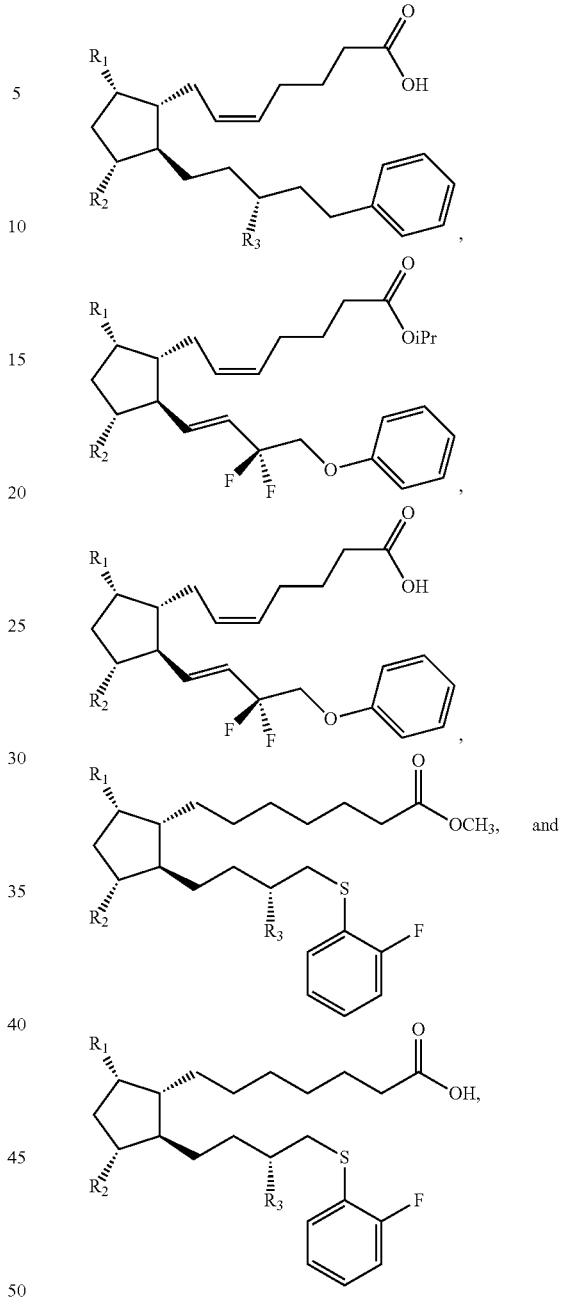

wherein:
R$_1$ is —O(CO)R$_6$ and R$_2$ is —OH, or
R$_1$ is —OH, R$_2$ is —O(CO)R$_6$, or
R$_1$ is —OH, R$_2$ is —OH, and R$_3$ is —O(CO)R$_8$, or
R$_1$ is —OH, R$_2$ is —O(CO)R$_6$, and R$_3$ is —OH, or
R$_1$ is —O(CO)R$_6$, R$_2$ is —O(CO)R$_6$, and R$_3$ is —OH, or
R$_1$ is —O(CO)R$_6$, R$_2$ is —OH, and R$_3$ is —O(CO)R$_8$, or
R$_1$ is —OH, R$_2$ is —O(CO)R$_6$, and R$_3$ is —O(CO)R$_8$, or
R$_1$ is —O(CO)R$_6$, R$_2$ is —O(CO)R$_6$, and R$_3$ is —O(CO)R$_8$, wherein R$_6$ and R$_8$ are as defined herein, and pharmaceutically acceptable salts, hydrates, solvates, stereoisomers, polymorphs, tautomers, isotopically enriched derivatives, and prodrugs thereof. In certain embodiments, R$_8$ is —(CH$_2$)$_q$CH$_3$ wherein q is 0, 1, 2, 3, 4, 5, or 6, —CH(CH$_3$)$_2$, —CH$_2$CH(CH$_3$)$_2$, —CH$_2$C(CH$_3$)$_3$, or —C(CH$_3$)$_3$. In certain embodiments, $R_6$ is —$(CH_2)_r CH_3$ wherein r is 0, 1, 2, 3, 4, 5, or 6, —$CH(CH_3)_2$, —$CH_2CH(CH_3)_2$, —$CH_2C(CH_3)_3$, or —$C(CH_3)_3$.

In certain embodiments, the compound of Formula (I) is selected from the group consisting of latanoprost, latanoprost free acid, tafluprost, tafluprost free acid, travoprost, fluprostenol, bimatoprost, bimatoprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost, latanoprost free acid, tafluprost, tafluprost free acid, and pharmaceutically acceptable salts, hydrates, solvates, stereoisomers, polymorphs, tautomers, isotopically enriched derivatives, and prodrugs thereof. In certain embodiments, the compound of Formula (I) is selected from the group consisting of latanoprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of latanoprost free acid and pharmaceutically acceptable salts, hydrates, solvates, stereoisomers, polymorphs, tautomers, isotopically enriched derivatives, and prodrugs thereof. In certain embodiments, the compound of Formula (I) is latanoprost. In certain embodiments, the compound of Formula (I) is selected from the group consisting of tafluprost and pharmaceutically acceptable hydrates, solvates, stereoisomers, polymorphs, tautomers, isotopically enriched derivatives, and prodrugs thereof. In certain embodiments, the compound of Formula (I) is selected from the group consisting of tafluprost free acid and pharmaceutically acceptable salts, hydrates, solvates, stereoisomers, polymorphs, tautomers, isotopically enriched derivatives, and prodrugs thereof. In certain embodiments, the compound of Formula (I) is tafluprost.

Exemplary compounds of Formula (II) include, but are not limited to,

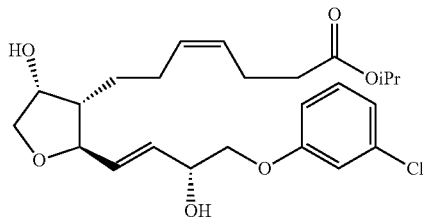 [SMILES: CC(C)OC(=O)CC/C=C\CC[C@H]1[C@@H](O)CO[C@@H]1/C=C/[C@@H](O)COc1cccc(Cl)c1]

also referred to as AL-12182;

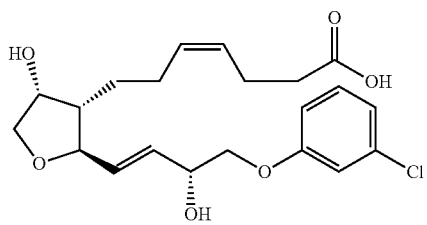 [SMILES: O=C(O)CC/C=C\CC[C@H]1[C@@H](O)CO[C@@H]1/C=C/[C@@H](O)COc1cccc(Cl)c1]

also referred to as AL-12182 free acid;
and ester derivatives (e.g., prodrugs) of the above, e.g., of formula:

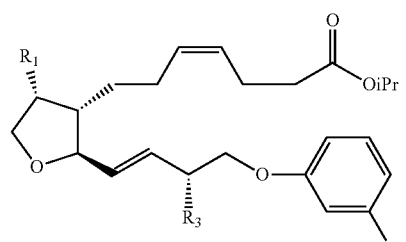

and

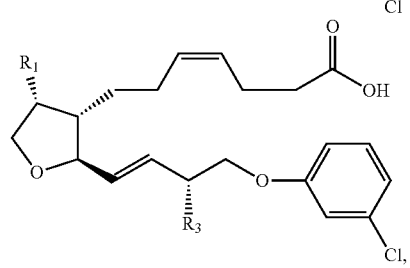

wherein:
$R_1$ is —OH and $R_3$ is —O(CO)$R_8$, or
$R_1$ is —O(CO)$R_6$, and $R_3$ is —OH, or
$R_1$ is —O(CO)$R_6$, and $R_3$ is —O(CO)$R_8$, wherein $R_6$ and $R_8$ are as defined herein, and pharmaceutically acceptable salts, hydrates, solvates, stereoisomers, polymorphs, tautomers, isotopically enriched derivatives, and prodrugs thereof. In certain embodiments, $R_8$ is —$(CH_2)_q CH_3$ wherein q is 0, 1, 2, 3, 4, 5, or 6, —$CH(CH_3)_2$, —$CH_2CH(CH_3)_2$, —$CH_2C(CH_3)_3$, or —$C(CH_3)_3$. In certain embodiments, $R_6$ is —$(CH_2)_r CH_3$ wherein r is 0, 1, 2, 3, 4, 5, or 6, —$CH(CH_3)_2$, —$CH_2CH(CH_3)_2$, —$CH_2C(CH_3)_3$, or —$C(CH_3)_3$—.

In certain embodiments, the compound of Formula (I) or (II) is a prodrug of any one of the compounds described herein. Exemplary prodrugs include esters, amides, and/or thioamides of the parent free acid, and compounds wherein a hydroxyl group on the parent compound (e.g., a pentacyclic hydroxyl group $R_1$ and/or $R_2$ or the hydroxyl group at the $R_3$/and/or $R_3'$ position) is esterified, e.g., 9-, 11-, and/or 15-ester derivatives as described herein, e.g., wherein the ester at said position is a $C_{1-6}$ ester, e.g., 9-propionyl bimatoprost, 11-propionyl bimatoprost, 15-propionyl bimatoprost, 9-butyryl bimatoprost, 11-butyryl bimatoprost, 15-butyryl bimatoprost, and the like.

Compositions and Formulations

As generally described herein, provided are topical compositions for use in any of the inventive methods, described herein, comprising a PFPRA compound (the "active ingredient"), and optionally a pharmaceutically acceptable excipient.

Topical compositions, as used herein, encompass pharmaceutical compositions as well as cosmetic compositions. While pharmaceutical compositions are useful for therapeutic and prophylactic purposes, and cosmetic compositions are useful for beautification purposes.

In addition to the PFPRA compound, the topical composition may additionally comprise one or more pharmaceutically acceptable excipients. Pharmaceutically acceptable excipients include, but are not limited to, any and all solvents, diluents or other liquid vehicles, inert diluents, dispersing and/or granulating agents, surface active agents and/or emulsifiers, thickening agents, disintegrating agents, binding agents, preservatives, buffering agents, lubricating agents, and/or oils. Excipients such as coloring agents, coating agents, perfuming agents, and sunscreens may also be present in the composition. General considerations in the formulation and/or manufacture of the topical compositions can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

In some embodiments, the composition is a non-emulsion, i.e., is not an emulsion. In certain embodiments, the composition is not irritating to the skin.

Exemplary solvents and liquid vehicles include, but are not limited to, organic solvents (e.g., polar protic solvents, polar aprotic solvents), water, saline, buffered aqueous solutions, and mixtures thereof. Exemplary polar protic solvents include, but are not limited to, organic alcohols such as methanol, ethanol, propanol, isopropanol, 1,3-butanediol, ethylene glycol, or propylene glycol, or mixture thereof. However, in certain embodiments, 1,3,-butanediol is excluded. Exemplary polar aprotic solvents include, but are not limited to, dimethylsulfoxide (DMSO), and ethers such as diethyl ether and diethylene glycol monoethyl ether (DEGEE).

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include lipids/natural emulsifiers (e.g. acacia, agar, alginic acid, sodium alginate, tragacanth, chondrus, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. corn starch and starch paste); gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isabgol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In some embodiments, the composition further comprises a viscosity enhancing agent. A viscosity enhancing agent, as used herein, is a substance which increases the viscosity of a solution or liquid/solid mixture. Exemplary viscosity enhancing agents include, but are not limited to, glycerin; cellulose derivatives (e.g., methylcellulose (MC); hydroxypropylmethylcellulose (HPMC); carboxymethylcellulose (CMC); microcrystalline cellulose (CC); ethyl cellulose; hydroxyethyl cellulose (HEC); hydroxypropyl cellulose (HPC); cellulose); gelatin; starch; hetastarch; poloxamers; pluronics; sodium CMC; sorbitol; acacia; povidone; carbopol; polycarbophil; chitosan; alginate; chitosan glutamate; hyaluronic acid; elastin; hyaluronan; maltodextrin DE; deoxyglycocholate (GDC); polymethacrylic acid; glycols (e.g., polymethylene glycol; polyethylene glycol); cyclodextrins (e.g., sulfobutylether B cyclodextrin); sodium taurodihydrofusidate (STDHF); and N-trimethyl chitosan chloride (TMC). In certain embodiments, the viscosity enhancing agent is a cellulose derivative, e.g., hydroxypropyl cellulose (HPC). In certain embodiments, the composition comprises a viscosity enhancing agent between about 0.5% and about 5% by weight, inclusive. In certain embodiments, the composition comprises a viscosity enhancing agent in between about 0.5% and about 4%, between about 0.5% and about 3%, between about 0.5% and about 2%, between about 0.5% and about 1%, between about 0.8% and about 5%, between about 0.8% and about 4%, between about 0.8% and about 3%, between about 0.8% and about 2%, or between about 0.5% and about 1%, inclusive. In certain embodiments, the composition comprises a viscosity enhancing agent in about 0.5%, 0.6%, 0.7%, 0.8%, 0.9%, 1%, 2%, 3%, 4%, or 5% (by weight). In certain embodiments, the composition comprises hydroxypropylcellulose in about 1% by weight.

In certain embodiments, the composition further comprises an antioxidant, e.g., alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. In certain embodiments, the composition comprises an antioxidant in between about 0.001% and about 0.1% by weight, inclusive. In certain embodiments, the composition comprises an antioxidant in between about 0.001% and about 0.05%, 0.001% and about 0.04%, 0.001% and about 0.03%, 0.001% and about 0.02%, 0.001% and about 0.01%, inclusive. In certain embodiments, the composition comprises an antioxidant in about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1% by weight. In certain embodiments, the composition comprises alpha tocopherol in about 0.002% by weight.

In certain embodiments, the composition further comprises a fatty acid and/or fatty acid ester, e.g., of the below formulae:

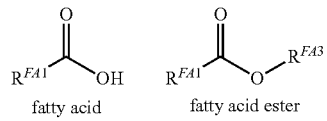

fatty acid    fatty acid ester wherein the alcohol moiety of the ester ($R^{FA3}$) is optionally substituted $C_1$-$C_6$ alkyl, and the acyl moiety of the ester or acid ($R^{FA1}$) is optionally substituted $C_{10}$-$C_{20}$ alkyl or optionally substituted $C_{10}$-$C_{20}$ alkenyl.

In certain embodiments, $R^{FA3}$ is an optionally substituted $C_{1-5}$alkyl, $C_{1-4}$alkyl, $C_{1-3}$alkyl, $C_{1-2}$alkyl, $C_{2-6}$alkyl, $C_{2-5}$alkyl, $C_{2-4}$alkyl, $C_{2-3}$alkyl, $C_{3-6}$alkyl, $C_{3-5}$alkyl, $C_{3-4}$alkyl, $C_{4-6}$alkyl, $C_{4-5}$alkyl, or $C_{5-6}$alkyl. In certain embodiments, $R^{FA3}$ is a branched alkyl group, e.g., for example, isopropyl, isobutyl, sec-butyl, tert-butyl, or neopentyl. In certain embodiments, $R^{FA3}$ is an unbranched alkyl group, e.g., for example, methyl, ethyl, n-propyl, n-butyl, n-pentyl, or n-hexyl. In certain embodiments, $R^{FA3}$ is an unsubstituted alkyl group, i.e., comprising only carbon and hydrogen atoms. In certain embodiments, $R^{FA3}$ is a substituted alkyl group, e.g., substituted by halogen atoms.

In certain embodiments, $R^{FA1}$ is an optionally substituted $C_{10}$-$C_{19}$ alkyl, $C_{10}$-$C_{18}$ alkyl, $C_{10}$-$C_{17}$ alkyl, $C_{10}$-$C_{16}$ alkyl, $C_{10}$-$C_{15}$ alkyl, $C_{10}$-$C_{14}$ alkyl, $C_{10}$-$C_{13}$ alkyl, $C_{11}$-$C_{20}$ alkyl, $C_{11}$-$C_{19}$ alkyl, $C_{11}$-$C_{18}$ alkyl, $C_{11}$-$C_{17}$ alkyl, $C_{11}$-$C_{16}$ alkyl, $C_{11}$-$C_{15}$ alkyl, $C_{11}$-$C_{14}$ alkyl, $C_{11}$-$C_{13}$ alkyl, $C_{12}$-$C_{19}$ alkyl, $C_{12}$-$C_{18}$ alkyl, $C_{12}$-$C_{17}$ alkyl, $C_{12}$-$C_{16}$ alkyl, $C_{12}$-$C_{15}$ alkyl, $C_{12}$-$C_{14}$ alkyl, $C_{12}$-$C_{13}$ alkyl, $C_{13}$-$C_{20}$ alkyl, $C_{13}$-$C_{19}$ alkyl, $C_{13}$-$C_{18}$ alkyl, $C_{13}$-$C_{17}$ alkyl, $C_{13}$-$C_{16}$ alkyl, $C_{13}$-$C_{15}$ alkyl, $C_{13}$-$C_{14}$ alkyl, $C_{14}$-$C_{20}$ alkyl, $C_{14}$-$C_{19}$ alkyl, $C_{14}$-$C_{18}$ alkyl, $C_{14}$-$C_{17}$ alkyl, $C_{14}$-$C_{16}$ alkyl, $C_{14}$-$C_{15}$ alkyl, $C_{15}$-$C_{20}$ alkyl, $C_{15}$-$C_{19}$ alkyl, $C_{15}$-$C_{18}$ alkyl, $C_{15}$-$C_{17}$ alkyl, or $C_{15}$-$C_{16}$ alkyl. In certain embodiments, $R^{FA1}$ is a straight chain (unbranched) alkyl group. In certain embodiments, $R^{FA1}$ is an unsubstituted alkyl group, i.e., comprising only carbon and hydrogen atoms. In certain embodiments, $R^{FA1}$ is a substituted alkyl group, e.g., substituted by halogen atoms.

In certain embodiments, $R^{FA1}$ is an optionally substituted $C_{10}$-$C_{19}$ alkenyl, $C_{10}$-$C_{18}$ alkenyl, $C_{10}$-$C_{17}$ alkenyl, $C_{10}$-$C_{16}$ alkenyl, $C_{10}$-$C_{15}$ alkenyl, $C_{10}$-$C_{14}$ alkenyl, $C_{10}$-$C_{13}$ alkenyl, $C_{11}$-$C_{20}$ alkenyl, $C_{11}$-$C_{19}$ alkenyl, $C_{11}$-$C_{18}$ alkenyl, $C_{11}$-$C_{17}$ alkenyl, $C_{11}$-$C_{16}$ alkenyl, $C_{11}$-$C_{15}$ alkenyl, $C_{11}$-$C_{14}$ alkenyl, $C_{11}$-$C_{13}$ alkenyl, $C_{12}$-$C_{19}$ alkenyl, $C_{12}$-$C_{18}$ alkenyl, $C_{12}$-$C_{17}$ alkenyl, $C_{12}$-$C_{16}$ alkenyl, $C_{12}$-$C_{15}$ alkenyl, $C_{12}$-$C_{14}$ alkenyl, $C_{12}$-$C_{13}$ alkenyl, $C_{13}$-$C_{20}$ alkenyl, $C_{13}$-$C_{19}$ alkenyl, $C_{13}$-$C_{18}$ alkenyl, $C_{13}$-$C_{17}$ alkenyl, $C_{13}$-$C_{16}$ alkenyl, $C_{13}$-$C_{15}$ alkenyl, $C_{13}$-$C_{14}$ alkenyl, $C_{14}$-$C_{20}$ alkenyl, $C_{14}$-$C_{19}$ alkenyl, $C_{14}$-$C_{18}$ alkenyl, $C_{14}$-$C_{17}$ alkenyl, $C_{14}$-$C_{16}$ alkenyl, $C_{14}$-$C_{15}$ alkenyl, $C_{15}$-$C_{20}$ alkenyl, $C_{15}$-$C_{19}$ alkenyl, $C_{15}$-$C_{18}$ alkenyl, $C_{15}$-$C_{17}$ alkenyl, $C_{15}$-$C_{16}$ alkenyl. In certain embodiments, $R^{FA1}$ is a unbranched alkenyl group. In certain embodiments, $R^{FA1}$ is an unsubstituted alkenyl group, i.e., comprising only carbon and hydrogen atoms. In certain embodiments, $R^{FA1}$ is a substituted alkenyl group, e.g., substituted by halogen atoms. In certain embodiments, $R^{FA1}$ is an alkenyl group comprising 1, 2, 3, or 4 double bonds, each independently cis or trans.

In certain embodiments, $R^{FA1}$ is an alkenyl group comprising at least one cis double bond, e.g., 1, 2, 3, or 4 cis double bonds. In certain embodiments, $R^{FA1}$ is an alkenyl group of formula (a):

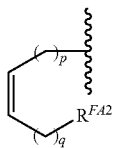

(a)

wherein:
p is an integer between 2 and 8, inclusive;
q is an integer between 1 and 8, inclusive; and
$R^{FA2}$ is an optionally substituted $C_1$-$C_{10}$ alkyl, or an optionally substituted $C_2$-$C_{10}$ alkenyl,
provided the sum of carbons of formula (a) does not exceed 20.

In certain embodiments, $R^{FA2}$ is an optionally substituted $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_{10}$ alkyl, $C_2$-$C_9$ alkyl, $C_2$-$C_8$ alkyl, $C_2$-$C_7$ alkyl, $C_2$-$C_6$ alkyl, $C_2$-$C_5$ alkyl, $C_2$-$C_4$ alkyl, $C_2$-$C_3$ alkyl, $C_3$-$C_{10}$ alkyl, $C_3$-$C_9$ alkyl, $C_3$-$C_8$ alkyl, $C_3$-$C_7$ alkyl, $C_3$-$C_6$ alkyl, $C_3$-$C_5$ alkyl, $C_3$-$C_4$ alkyl, $C_4$-$C_{10}$ alkyl, $C_4$-$C_9$ alkyl, $C_4$-$C_8$ alkyl, $C_4$-$C_7$ alkyl, $C_4$-$C_6$ alkyl, $C_4$-$C_5$ alkyl, $C_5$-$C_{10}$ alkyl, $C_5$-$C_9$ alkyl, $C_5$-$C_8$ alkyl, $C_5$-$C_7$ alkyl, $C_5$-$C_6$ alkyl, $C_6$-$C_{10}$ alkyl, $C_6$-$C_9$ alkyl, $C_6$-$C_8$ alkyl, $C_6$-$C_7$ alkyl, $C_7$-$C_{10}$ alkyl, $C_7$-$C_9$ alkyl, $C_7$-$C_8$ alkyl, $C_8$-$C_{10}$ alkyl, $C_8$-$C_9$ alkyl, or $C_9$-$C_{10}$ alkyl. In certain embodiments, $R^{FA2}$ is a straight chain (unbranched) alkyl group. In certain embodiments, $R^{FA2}$ is an unsubstituted alkyl group, i.e., comprising only carbon and hydrogen atoms. In certain embodiments, $R^{FA2}$ is a substituted alkyl group, e.g., substituted by halogen atoms.

In certain embodiments, $R^{FA2}$ is an optionally substituted $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl, $C_3$-$C_{10}$ alkenyl, $C_3$-$C_9$ alkenyl, $C_3$-$C_8$ alkenyl, $C_3$-$C_7$ alkenyl, $C_3$-$C_6$ alkenyl, $C_3$-$C_5$ alkenyl, $C_3$-$C_4$ alkenyl, $C_4$-$C_{10}$ alkenyl, $C_4$-$C_9$ alkenyl, $C_4$-$C_8$ alkenyl, $C_4$-$C_7$ alkenyl, $C_4$-$C_6$ alkenyl, $C_4$-$C_5$ alkenyl, $C_5$-$C_{10}$ alkenyl, $C_5$-$C_9$ alkenyl, $C_5$-$C_8$ alkenyl, $C_5$-$C_7$ alkenyl, $C_5$-$C_6$ alkenyl, $C_6$-$C_{10}$ alkenyl, $C_6$-$C_9$ alkenyl, $C_6$-$C_8$ alkenyl, $C_6$-$C_7$ alkenyl, $C_7$-$C_{10}$ alkenyl, $C_7$-$C_9$ alkenyl, $C_7$-$C_8$ alkenyl, $C_8$-$C_{10}$ alkenyl, $C_8$-$C_9$ alkenyl, or $C_9$-$C_{10}$ alkenyl. In certain embodiments, $R^{FA2}$ is a straight chain (unbranched) alkenyl group. In certain embodiments, $R^{FA2}$ is an unsubstituted alkenyl group, i.e., comprising only carbon and hydrogen atoms. In certain embodiments, $R^{FA2}$ is a substituted alkenyl group, e.g., substituted by halogen atoms. In certain embodiments, $R^{FA2}$ is a substituted alkenyl group, e.g., substituted by halogen atoms. In certain embodiments, $R^{FA2}$ is an alkenyl group comprising 1 or 2 double bonds, each independently cis or trans.

In certain embodiments, p is 2, 3, 4, 5, 6, 7, or 8. In certain embodiments, q is 1, 2, 3, 4, 5, 6, 7, or 8. In certain embodiments, p is 4, 5, 6, or 7. In certain embodiments, q is 1. In certain embodiments, q is 3, 4, or 5. In certain embodiments, q is 6, 7, or 8.

In certain embodiments, $R^{FA1}$ is selected from any one of the following saturated or unsaturated fatty acyl moieties:
Lauric —$(CH_2)_{10}CH_3$ (11 aliphatic carbons),
Myristic —$(CH_2)_{12}CH_3$ (13 aliphatic carbons),
Palmitic —$(CH_2)_{14}CH_3$ (15 aliphatic carbons),
Stearic —$(CH_2)_{16}CH_3$ (17 aliphatic carbons),
Myristoleic —$(CH_2)_7CH$=$CH(CH_2)_3CH_3$,
i.e., of formula

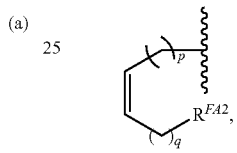

wherein p=7, q=3, $R^{FA2}$=—$CH_3$ (13 aliphatic carbons)
Palmitoleic —$(CH_2)_7CH$=$CH(CH_2)_5CH_3$,
i.e., of formula

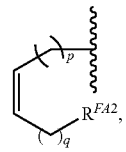

wherein p=7, q=5, $R^{FA2}$=—$CH_3$ (15 aliphatic carbons)
Sapienic —$(CH_2)_4CH$=$CH(CH_2)_8CH_3$,
i.e., of formula

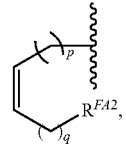

wherein p=4, q=8, $R^{FA2}$=—$CH_3$ (15 aliphatic carbons)
Oleic —$(CH_2)_7CH$=$CH(CH_2)_7CH_3$,
i.e., of formula

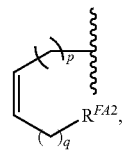

wherein p=7, q=7, $R^{FA2}$=—CH$_3$ (17 aliphatic carbons)
Linoleic —(CH$_2$)$_7$CH=CHCH$_2$CH=CH(CH$_2$)$_4$CH$_3$,
i.e., of formula

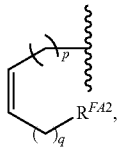

wherein p=7, q=1, $R^{FA2}$=C$_7$-alkenyl (17 aliphatic carbons)
α-Linolenic —(CH$_2$)$_7$
CH=CHCH$_2$CH=CHCH$_2$CH=CHCH$_2$CH$_3$,
i.e., of formula

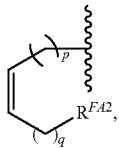

wherein p=7, q=1, $R^{FA2}$=C$_7$-alkenyl (17 aliphatic carbons)

In certain embodiments, the total number of aliphatic carbons atoms in the fatty acid is between 11 and 19, inclusive, i.e., 11, 12, 13, 14, 15, 16, 17, 18, or 19 aliphatic carbon atoms total. In certain embodiments, the total number of aliphatic carbons in the fatty acid is selected to approximate the aliphatic chain length of the PFPRA compound (e.g., latanoprost has 13 aliphatic carbons if the cyclizing carbons 9 through 11 of the cyclopentyl ring are not counted). For example, in certain embodiments, the total carbon atoms in the aliphatic chain of the PFPRA compound is between 11 and 19, inclusive, i.e., 11, 12, 13, 14, 15, 16, 17, 18, or 19 aliphatic carbon atoms total.

In certain embodiments, the total number of carbons atoms in the fatty acid ester, which include the number of carbons of $R^{FA1}$ and $R^{FA3}$ is between 11 and 19, inclusive, i.e., 11, 12, 13, 14, 15, 16, 17, 18, or 19 carbon atoms total. In some embodiments, the total number of carbons in the fatty acid ester is selected to approximate the total carbon atoms in the sum of the aliphatic chain and ester moiety of the PFPRA compound. For example, in certain embodiments, the total carbon atoms in the sum of the aliphatic chain and ester moiety of the PFPRA compound is between 11 and 19, inclusive, i.e., 11, 12, 13, 14, 15, 16, 17, 18, or 19 carbon atoms total.

In some embodiments, fatty acid or fatty acid ester is selected such that its predicted length (e.g. by molecular modeling) is similar (e.g., within ±3 Å) to the predicted length of the PFPRA compound. For example, the fatty acid oleic acid has a predicted length (between the two most distant heavy atoms) of about 19 Å, and the fatty acid ester isopropyl myristate has a predicted length (between the two most distant heavy atoms) of about 20 Å, each of which compares favorably with a length of about 17 Å for latanoprost free acid, tafluprost free acid, and bimatoprost free acid; 18 Å for latanoprost and tafluprost; about 19 Å for bimatoprost and travoprost free acid (i.e., fluprostenol), and about 20 Å for travoprost. In some embodiments, the predicted length is in an energy-minimized conformation. In some embodiments, the predicted length is in an energy-minimized conformation. In some embodiments, the predicted length is of a conformation whereby freely rotating bonds are rotated as to provide a maximal length.

In some embodiments, the final concentration of the fatty acid is between about 1 percent to about 20 percent by weight, inclusive. In some embodiments, the final concentration of the fatty acid is between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the fatty acid is 1, 2, 3, 4, 5, 6, 7, 8, 9, 10, 11, 12, 13, 14, 15, 16, 17, 18, 19, or 20 percent by weight.

In some embodiments, the final concentration of the fatty acid ester is between about 1 percent to about 20 percent by weight, inclusive. In some embodiments, the final concentration of the fatty acid ester is between about 5 and about 15 percent, about 1 and about 10 percent, about 1 and about 2 percent, about 1 and about 3 percent, about 1 and about 5 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the fatty acid ester is 1, 2, 3, 4, 5, 6, 7, 8, 9, 10, 11, 12, 13, 14, 15, 16, 17, 18, 19, or 20 percent by weight.

In some embodiments, fatty acid ester is isopropyl myristate. In some embodiments, the composition comprises isopropyl myristate and one or more additional different fatty acid esters. Alternatively, in some embodiments, isopropyl myristate cannot be replaced with a different fatty acid ester. In some embodiments, the composition comprises isopropyl myristate and does not comprise one or more additional different fatty acid esters.

In some embodiments, the composition further comprises an organic alcohol, e.g., methanol, ethanol, propanol, isopropanol, 1,3-butanediol, ethylene glycol, or propylene glycol. In some embodiments, the final concentration of an organic alcohol is between about 5 percent and about 99 percent by weight.

In some embodiments, the composition comprises an organic alcohol which acts as a base excipient (i.e., constituting the major component of the composition, such as for example, provided in greater than 50% by weight). In some embodiments, the final concentration of the organic alcohol base excipient is greater than 50 percent and about 99 percent by weight, inclusive. In some embodiments, the final concentration of the organic alcohol base excipient is between about 51 percent and 60 percent, 51 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent, inclusive. In certain embodiments, the organic alcohol which acts as a base excipient is ethanol.

In some embodiments, the composition comprises an organic alcohol which is not the base component of the composition (e.g., provided as a component in 50% or less by weight). In certain embodiments, the final concentration of the organic alcohol is between about 5 percent and about 50 percent by weight, inclusive. In some embodiments, the final concentration of the organic alcohol is between about 5 percent and 10 percent, about 5 percent and about 15 percent, about 10 percent and about 15 percent, about 10 percent and about 20 percent, about 15 percent and about 20 percent, about 15 percent and about 25 percent, about 20 percent and about 25 percent, about 20 percent and 30 percent, about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. In certain embodiments, the composition comprises an organic alcohol in 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight. In certain embodiments, the organic alcohol is propylene glycol.

In certain embodiments, the composition further comprises an ointment base. As used herein, an ointment base is a homogeneous, viscous, semi-solid preparation, which comprises a greasy, ointment base having a medium-to-high viscosity, that is intended for topical application to the skin. Exemplary ointment bases include, but are not limited to, hydrocarbon bases/waxes (e.g., plant and animal waxes (e.g., beeswax, lanolin, carnauba wax), petroleum derived waxes (e.g., hard paraffin wax or soft paraffin wax, i.e., petroleum jelly), microcrystalline wax, ceresine wax, white wax, yellow wax, and cetyl esters wax). In certain embodiments, the ointment base is a hydrocarbon base, e.g., petroleum jelly. Petroleum jelly (also known as petrolatum, white petrolatum, soft paraffin wax or multi-hydrocarbon wax) is a semi-solid preparation typically comprising (or consisting of) one or more saturated hydrocarbons with carbon numbers mainly higher than 25 (typically 25 to 50, such as 25 to 40, such as 25 to 35). It typically has a boiling point of from about 250° C. to about 350° C., such as about 280° C. to about 320° C., preferably about 300° C., and a melting point typically from about 36° C. to about 60° C. In certain embodiments, the petroleum jelly is obtained in sterile form or is sterilized prior to manufacturing the composition. In certain embodiments, the petroleum jelly is pure ultra white petroleum jelly. In some embodiments, the final concentration of ointment base is between about 50 percent and about 99 percent by weight. In some embodiments, the final concentration of ointment base is between about 50 percent and 60 percent, 50 percent and about 70 percent, about 60 percent and about 70 percent, about 60 percent and about 80 percent, about 70 percent and about 80 percent, about 70 percent and about 90 percent, about 80 percent and about 90 percent, about 85 percent and about 95 percent, about 90 percent and about 95 percent, about 90 percent and about 99 percent, and about 95 percent and about 99 percent.

Topical compositions as described herein can be prepared by any method known in the art of pharmacology. In general, such preparatory methods include the steps of bringing the PFPRA compound into association with an excipient and/or one or more other accessory ingredients, and then, if necessary and/or desirable, shaping and/or packaging the product into a dosage form.

Compositions for topical administration of the PFPRA compound may include ointments, pastes, creams, lotions, gels, powders, solutions, sprays, and/or patches. Generally, the PFPRA compound is admixed under sterile conditions with a pharmaceutically acceptable excipient and/or any needed preservatives and/or buffers as can be required. Furthermore, a PFPRA compound can be combined with, incorporated into, and/or delivered by means of a patch or dressing, which often have the added advantage of providing controlled delivery of the PFPRA compound to the skin and/or subcutaneous fat. Such dosage forms can be prepared, for example, by dissolving and/or dispensing the PFPRA compound in the proper medium. Alternatively or additionally, the rate can be controlled by either providing a rate controlling membrane and/or by dispersing the PFPRA compound in a polymer matrix and/or gel. In some embodiments, skin surface exposure can be controlled by applying or removing the patch or dressing.

As used herein, the term "dose" or "dosed" means the measured amount of a composition to be administered at one time. Relative amounts of the dose to be administered (e.g., comprising the PFPRA compound, the pharmaceutically acceptable excipient, and/or any additional ingredients) in the topical composition will vary, depending upon the identity, size, and/or condition of the subject treated and further depending upon the route by which the composition is to be administered. By way of example, a dose of the topical composition may comprise between about 0.0001% and about 10% (w/w) of the PFPRA compound. In some embodiments, the concentration of the PFPRA compound is between about 0.0001 percent and about 1 percent, about 0.0001 and about 0.0003 percent, about 0.0001 and about 0.001 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, or about 0.3 and about 1 percent (by weight), inclusive, per dose of the topical composition.

In certain embodiments, the composition comprises a PFPRA compound, fatty acid ester (e.g., isopropyl myristate), and an ointment base. In some embodiments, the composition further comprises an organic alcohol, e.g., methanol, ethanol, propanol, isopropanol, 1,3-butanediol, ethylene glycol, or propylene glycol. In certain embodiments, the organic alcohol is propylene glycol. In certain embodiments, the composition comprises latanoprost, isopropyl myristate, and an ointment base. In certain embodiments, the composition comprises tafluprost, isopropyl myristate, and an ointment base. In certain embodiments, the composition consists essentially of the above-recited components. In certain embodiments, the composition is not irritating to the skin. In certain embodiments, the composition is sterile, endotoxin-free or essentially endotoxin-free, ophthalmic, and/or ophthalmically compatible.

Kalayoglu (PCT/US2012/021692; WO2012/099942) teaches certain formulations for systemic (transdermal) delivery of a PFPRA to the bloodstream. These include two emulsions (Lipoderm or pluronic lecithin organogel). Emulsions are challenging to manufacture and susceptible to phase separation; e.g., for example, pluronic lecithin organogel is prone to phase separation at temperatures of about 5° C. or below. Thus, in some embodiments, the composition is a non-emulsion, i.e., is not an emulsion. In some embodiments, the composition in a non-emulsion comprising a PFPRA compound, fatty acid ester (e.g., isopropyl myristate), and an ointment base. In some embodiments, the composition is a non-emulsion comprising a PFPRA compound, fatty acid ester (e.g., isopropyl myristate), an organic alcohol, and an ointment base.

In some embodiments, the final concentration of the PFPRA compound provided in the composition is between about 0.0001 percent and about 1 percent (by weight). In some embodiments, the final concentration is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive. These percentages are expressed by weight of the total weight of the composition.

In some embodiments, the PFPRA compound is latanoprost and the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, about 0.05 and about 5 percent, or about 0.3 and about 1 percent (by weight), inclusive.

In some embodiments, the PFPRA compound is tafluprost and the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, about 0.05 and about 5 percent, or about 0.3 and about 1 percent (by weight), inclusive. These percentages are expressed by weight of the total weight of the composition.

In some embodiments, the final concentration of the fatty acid ester (e.g., isopropyl myristate) is between about 1 percent to about 20 percent by weight, inclusive. In some embodiments, the final concentration is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, inclusive. In certain embodiments, the final concentration of the fatty acid ester (e.g., isopropyl myristate) is 1, 2, 3, 4, 5, 6, 7, 8, 9, 10, 11, 12, 13, 14, 15, 16, 17, 18, 19, or 20 percent by weight. These percentages are expressed by weight of the total weight of the composition.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 and about 5 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive. These percentages are expressed by weight of the total weight of the composition.

In some embodiments, the composition comprises an ointment base, e.g., a hydrocarbon base. In some embodiments, the hydrocarbon base is selected from the group consisting of white wax, yellow wax, hard paraffin wax, petroleum jelly, and cetyl esters wax. In some embodiments, the final concentration of ointment base is between about 50 percent and about 99 percent by weight. In some embodiments, the final concentration of ointment base is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. In some embodiments, the ointment base is petroleum jelly, and the final concentration of petroleum jelly is between about 50 percent and about 99 percent by weight, inclusive. In some embodiments, the final concentration of petroleum jelly is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 and about 5 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the composition further comprises an organic alcohol (e.g., propylene glycol). In some embodiments, the final concentration of propylene glycol is between about 5 percent and about 50 percent by weight, inclusive. In some embodiments, the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.03 and about 0.1 percent, about 0.1 and about 0.3 percent, about 0.1 and about 1 percent, about 0.05 and about 5 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; and the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive. These percentages are expressed by weight of the total weight of the composition.

In some embodiments, the PFPRA compound is latanoprost; the final concentration of latanoprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the PFPRA compound is tafluprost; the final concentration of tafluprost is between about 0.001 percent and about 1 percent, 0.001 and about 0.003 percent, about 0.001 and about 0.01 percent, about 0.003 and about 0.01 percent, about 0.01 and about 0.03 percent, about 0.01 and about 0.1 percent, about 0.05 and about 5 percent, about 0.03 and about 0.1 percent, about 0.1 and about 0.3 percent, about 0.1 and about 1 percent, or about 0.3 and about 1 percent (by weight), inclusive; and the final concentration of fatty acid ester (e.g., isopropyl myristate) is between about 5 and about 15 percent, about 1 and about 10 percent, about 1 and about 2 percent, about 1 and about 3 percent, about 2 and about 4 percent, about 3 and about 5 percent, about 3 and about 7 percent, about 4 and about 6 percent, about 5 and about 7 percent, about 6 and about 8 percent, about 7 and about 10 percent, about 10 and about 20 percent, about 10 and about 15 percent, or about 15 and about 20 percent, by weight, inclusive; the final concentration of the organic alcohol (e.g., propylene glycol) is between about 5 percent and 10 percent, about 5 percent and about 15 percent, about 5 percent and about 20 percent, about 10 percent and about 15 percent, about 10 percent and about 20 percent, about 15 percent and about 20 percent, about 15 percent and about 25 percent, about 20 percent and about 25 percent, about 20 percent and 30 percent about 25 percent and about 30 percent, about 25 percent and about 35 percent, about 30 percent and about 35 percent, about 30 percent and about 40 percent, about 35 percent and about 40 percent, about 35 percent and about 45 percent, about 40 percent and about 50 percent, about 40 percent and about 45 percent, or about 45 percent and about 50 percent, inclusive; and the final concentration of the ointment base (e.g., petroleum jelly) is between about 50 percent and 60 percent, 50 percent and about 70 percent, about 60 percent and about 70 percent, about 60 percent and about 80 percent, about 70 percent and about 80 percent, about 70 percent and about 90 percent, about 70 percent and about 99 percent, about 80 percent and about 90 percent, about 85 percent and about 95 percent, about 90 percent and about 95 percent, about 90 percent and about 99 percent, and about 95 percent and about 99 percent, inclusive. These percentages are expressed by weight of the total weight of the composition.

In some embodiments, the composition is sterile. Generally, methods of manufacturing a sterile composition include gamma irradiation, heat (e.g., autoclave or dry heat), and microfiltration (e.g., with a 0.2 micron filter); however, some of these methods can be unsuitable for certain compositions. For example, gamma irradiation or heat can cause degradation of the PFPRA compound; oleaginous bases such as petroleum jelly are not amenable to autoclave sterilization; and some excipients may be incompatible or poorly compatible with a 0.2 micron filter.

Although the descriptions of the topical compositions provided herein are principally directed to compositions that are suitable for administration to humans, it will be understood by the skilled artisan that such compositions are generally suitable for administration to animals of all sorts. Modification of the topical composition suitable for administration to humans in order to render the composition suitable for administration to various animals is well understood, and the ordinarily skilled veterinary pharmacologist can design and/or perform such modification with ordinary experimentation. General considerations in the composition and/or manufacture of compositions can be found, for example, in *Remington: The Science and Practice of Pharmacy* 21st ed., Lippincott Williams & Wilkins, 2005.

Still further encompassed by the invention are kits comprising a topical composition as described herein and instructions for use. Kits provided may comprise a provided composition and a container (e.g., a tube, vial, ampoule, bottle, syringe, and/or dispenser package, or other suitable container).

Dosing Regimen for Reduction of Subcutaneous Fat

As generally described herein, the topical compositions as described herein are contemplated useful in the reduction of subcutaneous fat in a subject in need thereof.

In one aspect, provided is a prostaglandin FP receptor agonist compound for topical use in reducing body fat, whereby the duration of skin surface exposure to the composition or residue thereof is between about 4 hour and about 12 hours per dose of the composition.

In another aspect, provided is a method for locally reducing body fat in a subject in need thereof, the method comprising administering a topical composition comprising a PFPRA compound to the skin surface, and removing the topical composition or residue thereof from the skin surface between about 4 hour and about 12 hours after said administering. In certain embodiments, at the dermis has taken up at least 80% of maximal load by the PFPRA compound (or active metabolite thereof) within about 4 to about 12 hours of administration (with maximal load as defined herein). In certain embodiments, the step of removing comprises removing the composition or residue thereof from the skin surface after the dermis has taken up at least 80% of maximal load. In certain embodiments, more than about 60 percent of the 24-hour transcutaneous flux occurs within 4 to 12 hours after administration. In certain embodiments, the step of removing comprises removing the composition or residue thereof from the skin surface after more than about 60 percent of the 24-hour transcutaneous flux has occurred.

In another aspect, provided is a kit comprising a topical fat-reducing composition and instructions for use, wherein the composition comprises a PFPRA compound, and wherein the instructions provide for a duration of skin surface exposure to the composition or residue thereof of between about 4 hours and about 12 hours per dose of the composition.

In certain specific embodiments, provided is latanoprost for use in reducing body fat, wherein the latanoprost is provided in a topical composition, and whereby the duration of skin surface exposure to the composition or residue thereof is between about 4 hours and about 12 hours, inclusive, per dose of the composition. In certain embodiments, the duration is between about 4 hours and about 10 hours, inclusive, per dose of the composition. In certain embodiments, the duration is between about 4 hours and about 8 hours, inclusive, per dose of the composition. In certain embodiments, the duration is between about 6 hours and about 10 hours, inclusive, per dose of the composition. In certain embodiments, the composition is administered about once every 24 hours.

In certain specific embodiments, further provided is a method for locally reducing body fat in a subject in need thereof, the method comprising the steps of administering a composition comprising latanoprost to the skin surface; and removing the composition or residue thereof from the skin surface between about 4 hours and about 12 hours, inclusive, after said administering. In certain embodiments, the removing is between about 4 hours and about 10 hours, inclusive, after said administering. In certain embodiments, the removing is between about 4 hours and about 8 hours, inclusive, after said administering. In certain embodiments, the removing is between about 6 hours and about 10 hours, inclusive, after said administering. In certain embodiments, more than about 60 percent of the 24-hour flux of latanoprost or an active metabolite thereof occurs within 4 to 12 hours, inclusive, after the step of administering, and wherein the step of removing is after more than about 60 percent of the 24-hour flux has occurred. In certain embodiments, the dermis is fully loaded with latanoprost, an active metabolite thereof, or a combination thereof, within 4 to 12 hours, inclusive, after the administering, and wherein the step of removing is after the dermis is fully loaded.

In certain specific embodiments, provided is tafluprost for use in reducing body fat, wherein the tafluprost is provided in a topical composition, and whereby the duration of skin surface exposure to the composition or residue thereof is between about 4 hours and about 12 hours, inclusive, per dose of the composition. In certain embodiments, the duration is between about 4 hours and about 10 hours, inclusive, per dose of the composition. In certain embodiments, the duration is between about 4 hours and about 8 hours, inclusive, per dose of the composition. In certain embodiments, the duration is between about 6 hours and about 10 hours, inclusive, per dose of the composition. In certain embodiments, the composition is administered about once every 24 hours.

In certain specific embodiments, further provided is a method for locally reducing body fat in a subject in need thereof, the method comprising the steps of administering a composition comprising tafluprost to the skin surface; and removing the composition or residue thereof from the skin surface between about 4 hours and about 12 hours, inclusive, after said administering. In certain embodiments, the removing is between about 4 hours and about 10 hours, inclusive, after said administering. In certain embodiments, the removing is between about 4 hours and about 8 hours, inclusive, after said administering. In certain embodiments, the removing is between about 6 hours and about 10 hours, inclusive, after said administering. In certain embodiments, more than about 60 percent of the 24-hour flux of tafluprost or an active metabolite thereof occurs within 4 to 12 hours, inclusive, after the step of administering, and wherein the step of removing is after more than about 60 percent of the 24-hour flux has occurred. In certain embodiments, the dermis is fully loaded with tafluprost, an active metabolite thereof, or a combination thereof, within 4 to 12 hours, inclusive, after the administering, and wherein the step of removing is after the dermis is fully loaded.

In certain specific embodiments, provided is travoprost for use in reducing body fat, wherein the travoprost is provided in a topical composition, and whereby the duration of skin surface exposure to the composition or residue thereof is between about 4 hours and about 12 hours, inclusive, per dose of the composition. In certain embodiments, the duration is between about 4 hours and about 10 hours, inclusive, per dose of the composition. In certain embodiments, the duration is between about 4 hours and about 8 hours, inclusive, per dose of the composition. In certain embodiments, the duration is between about 6 hours and about 10 hours, inclusive, per dose of the composition. In certain embodiments, the composition is administered about once every 24 hours.

In certain specific embodiments, further provided is a method for locally reducing body fat in a subject in need thereof, the method comprising the steps of administering a composition comprising travoprost to the skin surface; and removing the composition or residue thereof from the skin surface between about 4 hours and about 12 hours, inclusive, after said administering. In certain embodiments, the removing is between about 4 hours and about 10 hours, inclusive, after said administering. In certain embodiments, the removing is between about 4 hours and about 8 hours, inclusive, after said administering. In certain embodiments, the removing is between about 6 hours and about 10 hours, inclusive, after said administering. In certain embodiments, more than about 60 percent of the 24-hour flux of travoprost or an active metabolite thereof occurs within 4 to 12 hours, inclusive, after the step of administering, and wherein the step of removing is after more than about 60 percent of the 24-hour flux has occurred. In certain embodiments, the dermis is fully loaded with travoprost, an active metabolite thereof, or a combination thereof, within 4 to 12 hours, inclusive, after the administering, and wherein the step of removing is after the dermis is fully loaded.

In certain specific embodiments, provided is bimatoprost for use in reducing body fat, wherein the bimatoprost is provided in a topical composition, and whereby the duration of skin surface exposure to the composition or residue thereof is between about 4 hours and about 12 hours, inclusive, per dose of the composition. In certain embodiments, the duration is between about 4 hours and about 10 hours, inclusive, per dose of the composition. In certain embodiments, the duration is between about 4 hours and about 8 hours, inclusive, per dose of the composition. In certain embodiments, the duration is between about 6 hours and about 10 hours, inclusive, per dose of the composition. In certain embodiments, the composition is administered about once every 24 hours.

In certain specific embodiments, further provided is a method for locally reducing body fat in a subject in need thereof, the method comprising the steps of administering a composition comprising bimatoprost to the skin surface; and removing the composition or residue thereof from the skin surface between about 4 hours and about 12 hours, inclusive, after said administering. In certain embodiments, the removing is between about 4 hours and about 10 hours, inclusive, after said administering. In certain embodiments, the removing is between about 4 hours and about 8 hours, inclusive, after said administering. In certain embodiments, the removing is between about 6 hours and about 10 hours, inclusive, after said administering. In certain embodiments, more than about 60 percent of the 24-hour flux of bimatoprost or an active metabolite thereof occurs within 4 to 12 hours, inclusive, after the step of administering, and wherein the step of removing is after more than about 60 percent of the 24-hour flux has occurred. In certain embodiments, the dermis is fully loaded with bimatoprost, an active metabolite thereof, or a combination thereof, within 4 to 12 hours, inclusive, after the administering, and wherein the step of removing is after the dermis is fully loaded.

In certain specific embodiments, further provided is a kit comprising a topical fat-reducing composition and instructions for use, wherein the composition comprises a prostaglandin FP receptor agonist compound, and wherein the instructions provide for a duration of skin surface exposure to the composition or residue thereof of between about 4 hours and about 12 hours, inclusive, per dose of the composition. In certain embodiments, the duration is between about 4 hours and about 10 hours, inclusive, per dose of the composition. In certain embodiments, the duration is between about 4 hours and about 8 hours, inclusive, per dose of the composition. In certain embodiments, the duration is between about 6 hours and about 10 hours, inclusive, per dose of the composition. In certain embodiments, the dose frequency is about once every 24 hours.

As used herein, the term "skin surface exposure" means the duration in which the PFPRA compound is in contact with the surface of the skin, prior to removal of the composition or residue thereof. For example, skin surface exposure begins when the topical composition comprising the PFPRA compound is applied to the skin and ends when the topical composition or residue thereof (which may or may not comprise unabsorbed PFPRA compound) is removed from the skin. Removal of the topical composition, in this instance, means gross removal (e.g., removal of 90%, 95%, 99%, or 100%) of the remaining topical composition, including any remaining PFPRA compound and any remaining excipients, from the skin surface, e.g., by washing, scrubbing, scraping, removing patches and the like, and/or stripping the skin. It should be understood that some ingredients of the topical composition can be volatile and can evaporate following application to the skin. Other ingredients do not necessarily evaporate. For example, PFPRA compounds are not generally considered to be volatile compounds.

As used herein, the "residue" of a composition refers to the portion(s) of a composition that remain on the skin surface after a period of time, taking into account losses due to absorption into the skin, evaporation, perspiration, chemical reaction, incidental physical losses, and the like.

As used herein in reference to a tissue, "maximal load," or "maximum load," or "maximally loaded" refer to the maximal concentration of a compound in a tissue (e.g., dermis or fat) during the dosing interval (e.g., 24 hours). The concentration can be expressed in terms of mass of compound per mass of tissue, for example, ng of compound per mg of tissue. Alternatively, the concentration can be expressed in terms of mass of compound per $cm^2$ of skin surface area. The maximal concentration can be the maximum value observed in the course of in vitro or in vivo pharmacokinetic experiment, or can be the calculated maximum based on any generally accepted method of regression or pharmacokinetic modeling (e.g., a nonlinear model).

In some embodiments, the maximal load is between about 0.01 nanograms (ng) and about 1000 nanograms (ng) of PFPRA compound per milligram of tissue. In some embodiments, the maximal load is between about 0.01 ng about 0.1 ng, about 0.01 ng and about 1 ng, about 0.01 ng and about 10 ng, about 0.01 ng and about 100 ng, about 0.1 ng to about 1 ng, about 0.1 ng and about 10 ng, about 0.1 ng and about 100 ng, about 1 ng and about 10 ng, about 1 ng and about 100 ng, about 10 ng and about 100 ng, about 10 ng and about 1000 ng, and about 100 ng and about 1000 ng of PFPRA compound per milligram of tissue.

In some embodiments, the maximal load is between about 1 ng and about 100,000 ng of PFPRA compound per $cm^2$ square of skin. In some embodiments, the maximal load is between about 1 ng about 10 ng, about 1 ng and about 100 ng, about 1 ng and about 1000 ng, about 1 ng and about 10,000 ng, about 10 ng to about 100 ng, about 10 ng and about 1000 ng, about 1 ng and about 10,000 ng, about 100 ng and about 1000 ng, about 100 ng and about 10,000 ng, about 1000 ng and about 10,000 ng, about 1000 ng and about 100,000 ng, and about 10,000 ng and about 100,000 ng of PFPRA per $cm^2$ of skin.

As used herein, the term "24-hour flux" (or interchangeably, "24-hour transcutaneous flux") means the cumulative amount of a PFPRA compound that crosses the skin and/or is detected in subcutaneous fat over the 24-hour period that commences upon application to the skin. In some cases, 24-hour flux can be determined or estimated by the amount of a PFPRA compound (or metabolite thereof) that has crossed the skin (e.g., into a serosal receptor compartment) in an in vitro or ex vivo skin permeation experiment (e.g., Franz cell); in subcutaneous fat in an in vivo experiment; or in blood (e.g., plasma or serum) in an in vivo experiment. In some cases, 24-hour flux is the determined or estimated by the area under a time-concentration curve. In some cases, 24-hour flux can be determined by use of chromatography, spectroscopy, immunoassay, or autoradiography. In some cases, 24-hour flux is normalized for the surface area of treated skin. In some cases, 24-hour flux is normalized for the dose, volume, and/or dose concentration of the composition. The skilled artisan will further appreciate that as the concept of 24-hour flux is particularly suitable for a 24-hour dose interval, the concept can be generalized for other dose intervals, e.g., a 72-hour flux for a 72-hour dose interval.

In some embodiments, 24-hour flux is between about 0.01 micrograms (µg) and about 1000 micrograms (µg) of PFPRA compound per $cm^2$ square of skin. In some embodiments, 24-hour flux is between about 0.01 µg about 0.1 µg, about 0.01 µg and about 1 µg, about 0.01 µg and about 10 µg, about 0.01 µg and about 100 µg, about 0.1 µg to about 1 µg, about 0.1 µg and about 10 µg, about 0.1 µg and about 100 µg, about 1 µg and about 10 µg, about 1 µg and about 100 µg, about 10 µg and about 100 µg, about 10 µg and about 1000 µg, and about 100 µg and about 1000 µg of PFPRA compound per $cm^2$ of skin.

In some embodiments wherein the area of treated skin is about 10 $cm^2$ and about 100 $cm^2$, 24-hour flux is between about 0.1 µg and about 100,000 µg of PFPRA compound. In some embodiments wherein the area of treated skin is about 10 and about 100 $cm^2$, 24-hour flux is between about 0.1 µg and about 1 µg, about 0.1 µg and about 10 µg, about 0.1 µg and about 100 µg, about 0.1 µg and about 1,000 µg, about 0.1 µg and about 10,000n, about 1 µg and about 10 µg, about 1 µg and about 100 µg, about 1 µg and about 1000 µg, about 1 µg and about 10,000n, about 10 µg and about 100 µg, about 10 µg and about 1000 µg, about 10 µg and about 10,000n, about 10 µg and about 100,000n, about 100 µg and about 1000 µg, about 100 µg and about 10,000n, about 100 µg and about 100,000 µg, about 1000 µg and about 10,000 µg, about 1000 µg and about 100,000 µg, and about 10,000 µg and about 100,000 µg of PFPRA compound.

In some embodiments, the composition is washed with water, and optionally with soap. In some embodiments, the composition is removed with the aid of a solvent. In some embodiments, the solvent comprises water, ethanol, and/or isopropanol. In some embodiments, the composition is removed mechanically. In some embodiments, composition is removed with the aid of an adhesive, tape (e.g., by epidermal stripping), or scraper. In some embodiments, wherein the composition is delivered by use of a patch or dressing, the composition is removed by removing the patch or dressing.

Fat reduction can include reducing fat as measured by at least one of volume, size, mass, bulk, density, amount, and/or quantity. The present invention is expected to reduce fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%. For example, fat reduction can also include reducing fat cell amount (for example, fat cell number), reducing fat cell volume, reducing fat cell maturation, and/or dedifferentiating a fat cell.

In certain embodiments, the body fat is local, e.g., concentrated on the face, periorbital area, cheeks, chin, neck, chest, breast, abdomen, buttocks, hips, thighs, legs, and/or arms.

In some embodiments of any of the above aspects of the invention, the duration of skin surface exposure to the composition is between about 4 hours and about 12 hours per dose of the composition, or about 6 hours and about 10 hours per dose of the composition. For example, in certain embodiments, the composition is administered to the skin surface, and then the remainder of the composition is removed after 4 hours, 5 hours, 6 hours, 7 hours, 8 hours, 9 hours, 10 hours, 11 hours, or 12 hours, after this application to the skin.

In any embodiment where the duration of skin surface exposure is described by an approximate range, e.g., between about 4 hours and about 12 hours, a corresponding exact range can be used, e.g., between 4 hours and 12 hours. Therefore, in some embodiments, the duration of skin surface exposure can be between 4 hours and 12 hours, between 4 hours and 8 hours, between 4 hours and 10 hours, or between 6 hours and 10 hours.

In certain embodiments of any of the above aspects of the invention, optionally wherein the dosing interval is about once per 24 hours, the dermis has more than 80% of maximal load within 4 to 12 hours after administration, e.g., within 4, 5, 6, 7, 8, 9, 10, 11, or 12 hours after administration. In certain embodiments, this dermis has more than about more than about 75 percent, more than about 80 percent, more than about 85 percent, more than about 90 percent, or more than about 95 percent of the maximal load within 4 to 12 hours after administration, e.g., within 4, 5, 6, 7, 8, 9, 10, 11, or 12 hours after administration. In certain embodiments, the step of removing comprises removing the composition or residue thereof from the skin surface after more than about 70 percent of the maximal load has occurred, or is considered to have occurred based on prior experimental evidence.

In some embodiments wherein 24-hour flux is about 100 nanograms per $cm^2$ of skin, the step of removing comprises removing the composition or residue thereof from the skin surface after more than about 60 to about 95 nanograms per $cm^2$ of flux have occurred. In some embodiments wherein 24-hour flux is about 100 nanograms per $cm^2$ of skin, the step of removing comprises removing the composition or residue thereof from the skin surface after more than about 60, about 65, about 70, about 75, about 80, about 85, about 90, or about 95 nanograms per $cm^2$ of flux have occurred.

In some embodiments wherein 24-hour flux is about 1 microgram per $cm^2$ of skin, the step of removing comprises removing the composition or residue thereof from the skin surface after more than about 0.6 to about 0.95 micrograms per $cm^2$ of flux have occurred. In some embodiments wherein 24-hour flux is about 1 microgram per $cm^2$ of skin, the step of removing comprises removing the composition or residue thereof from the skin surface after more than about 0.6, about 0.65, about 0.7, about 0.75, about 0.8, about 0.85, about 0.9, or about 0.95 micrograms per $cm^2$ of flux have occurred.

In some embodiments wherein 24-hour flux is about 10 micrograms per $cm^2$ of skin, the step of removing comprises removing the composition or residue thereof from the skin surface after more than about 6 to about 9.5 micrograms per $cm^2$ of flux have occurred. In some embodiments wherein 24-hour flux is about 10 micrograms per $cm^2$ of skin, the step of removing comprises removing the composition or residue thereof from the skin surface after more than about 6, about 6.5, about 7, about 7.5, about 8, about 8.5, about 9, or about 9.5 micrograms per $cm^2$ of flux have occurred.

In some embodiments wherein 24-hour flux is about 100 micrograms per $cm^2$ of skin, the step of removing comprises removing the composition or residue thereof from the skin surface after more than about 60 to about 95 micrograms per $cm^2$ of flux have occurred. In some embodiments wherein 24-hour flux is about 100 micrograms per $cm^2$ of skin, the step of removing comprises removing the composition or residue thereof from the skin surface after more than about 60, about 65, about 70, about 75, about 80, about 85, about 90, or about 95 micrograms per $cm^2$ of flux have occurred.

In certain embodiments of any of the above aspects of the invention, more than about 60 percent of the 24-hour flux occurs within 4 to 12 hours after administration, e.g., within 4, 5, 6, 7, 8, 9, 10, 11, or 12 hours after administration. In certain embodiments, more than about 65 percent, more than about 70 percent, more than about 75 percent, more than about 80 percent, more than about 85 percent, more than about 90 percent, or more than about 95 percent of the 24-hour flux occurs within 1 to 12 hours after administration, e.g., within 4, 5, 6, 7, 8, 9, 10, 11, or 12 hours after administration. In certain embodiments, the step of removing comprises removing the composition or residue thereof from the skin surface after more than 60 percent of the 24-hour flux has occurred, or is likely to have occurred based on prior experimental evidence.

In some embodiments wherein 24-hour flux is about 10 nanograms per $cm^2$ of skin, the step of removing comprises removing the composition or residue thereof from the skin surface after more than about 6 to about 9.5 nanograms per $cm^2$ of flux have occurred. In some embodiments wherein 24-hour flux is about 10 micrograms per $cm^2$ of skin, the step of removing comprises removing the composition or residue thereof from the skin surface after more than about 6, about 6.5, about 7, about 7.5, about 8, about 8.5, about 9, or about 9.5 nanograms per $cm^2$ of flux have occurred.

In some embodiments wherein 24-hour flux is about 100 nanograms per $cm^2$ of skin, the step of removing comprises removing the composition or residue thereof from the skin surface after more than about 60 to about 95 nanograms per $cm^2$ of flux have occurred. In some embodiments wherein 24-hour flux is about 100 nanograms per $cm^2$ of skin, the step of removing comprises removing the composition or residue thereof from the skin surface after more than about 60, about 65, about 70, about 75, about 80, about 85, about 90, or about 95 nanograms per $cm^2$ of flux have occurred.

In some embodiments wherein 24-hour flux is about 1 microgram per $cm^2$ of skin, the step of removing comprises removing the composition or residue thereof from the skin surface after more than about 0.6 to about 0.95 micrograms per $cm^2$ of flux have occurred. In some embodiments wherein 24-hour flux is about 1 microgram per $cm^2$ of skin, the step of removing comprises removing the composition or residue thereof from the skin surface after more than about 0.6, about 0.65, about 0.7, about 0.75, about 0.8, about 0.85, about 0.9, or about 0.95 micrograms per $cm^2$ of flux have occurred.

In some embodiments wherein 24-hour flux is about 10 micrograms per $cm^2$ of skin, the step of removing comprises removing the composition or residue thereof from the skin surface after more than about 6 to about 9.5 micrograms per $cm^2$ of flux have occurred. In some embodiments wherein 24-hour flux is about 10 micrograms per $cm^2$ of skin, the step of removing comprises removing the composition or residue thereof from the skin surface after more than about 6, about 6.5, about 7, about 7.5, about 8, about 8.5, about 9, or about 9.5 micrograms per $cm^2$ of flux have occurred.

In some embodiments wherein 24-hour flux is about 100 micrograms per $cm^2$ of skin, the step of removing comprises removing the composition or residue thereof from the skin surface after more than about 60 to about 95 micrograms per $cm^2$ of flux have occurred. In some embodiments wherein 24-hour flux is about 100 micrograms per $cm^2$ of skin, the step of removing comprises removing the composition or residue thereof from the skin surface after more than about 60, about 65, about 70, about 75, about 80, about 85, about 90, or about 95 micrograms per $cm^2$ of flux have occurred.

As used herein, unless otherwise defined by the context, the term "steady state" or "steady-state" means a condition in which the overall (e.g., daily) penetration of a PFPRA compound into subcutaneous fat is roughly in dynamic equilibrium with its removal from subcutaneous fat. Removal can occur, for example, by systemic absorption, (re)distribution into another compartment, and/or local metabolism to an inactive metabolite.

In certain embodiments, more than about 60 percent of steady-state exposure in subcutaneous fat is attributable to delivery of a PFPRA within 4 to 12 hours after administration e.g., within 4, 5, 6, 7, 8, 9, 10, 11, or 12 hours after administration. This is measured, for example, as the ratio of steady-state exposure in subcutaneous fat for 12 hours vs. 24 hours of skin surface exposure. In certain embodiments, more than about 65 percent, more than about 70 percent, more than about 75 percent, more than about 80 percent, more than about 85 percent, more than about 90 percent, or more than about 95 percent of steady-state exposure in subcutaneous fat is attributable to delivery of a PFPRA within 4 to 12 hours after administration, e.g., within 4, 5, 6, 7, 8, 9, 10, 11, or 12 hours after administration.

In some embodiments of any of the above aspects of the invention, the dose frequency is about once every 24 hours, about once every day, about once every 48 hours, about once every two days, about once every three days, about once every week, about once every two weeks, or about once every four weeks, or about once every month.

In some embodiments, steady-state in subcutaneous fat occurs after about 4 doses, about 5 doses, about 6 doses, about 7 doses, about 8 doses, about 9 doses, about 10 doses, about 15 doses, about 4 days, about 5 days, about 6 days, about 7 days, about 10 days, about 2 weeks, about 3 weeks, or about 1 month.

In some embodiments, treatment period is for about 1 weeks, about 2 weeks, about 3 weeks, about 4 weeks, about 6 weeks, about 7 weeks, about 8 weeks, about 9 weeks, about 10 weeks, about 1 month, about 2 months, about 3 months, about 4 months, about 5 months, about 6 months, about 7 months, about 8 months, about 9 months, about 10 months, about 11 months, about 12 months, about 18 months, about 2 years, or about 3 years. In some embodiments, treatment period continues indefinitely.

In some embodiments, a higher dose ("loading dose") is administered at or around the beginning of a treatment period, compared to subsequent doses in the treatment period. In some embodiments, the loading dose is achieved by use of higher dose concentration, higher dose volume, or higher dose frequency. In some embodiments, the loading dose is 1.5 time or greater than the subsequent dose(s), e.g., between about 1.5 times to about 5 times the subsequent dose(s), e.g., about 1.5 times, about 2 times, about 3 times, about 4 times, or about 5 times the subsequent dose(s).

EXAMPLES

Throughout the description, where compositions are described as having, including, or comprising specific components, it is contemplated that these compositions may also consist essentially of, or consist of, the recited components. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

Example 1

The following example describes a single-dose tissue pharmacokinetic experiment of topical latanoprost in minipigs. A composition comprising 0.8% latanoprost by weight was applied at different time points, each time to a separate but comparable application area on the back of an adult minipig. Twenty-four hours after the first dose, the animal was sacrificed and the skin was washed. Samples of skin, subcutaneous fat, and muscle were dissected en bloc from each application area and flash-frozen. Resulting fat samples were surface-washed with methanol, weighed, pulverized, resuspended, and homogenized. The content of latanoprost free acid (LFA, the active metabolite of latanoprost) in each sample was determined by an LC/MS/MS assay. The results are shown in Table 1.

TABLE 1

| Composition | Time since dose (h) | LFA concentration in subcutaneous fat (nanomolar) |
| --- | --- | --- |
| Latanoprost 0.8% in DMSO | 1 | 15 |
| | 2 | 7 |

TABLE 1-continued

| Composition | Time since dose (h) | LFA concentration in subcutaneous fat (nanomolar) |
|---|---|---|
| | 3 | 8 |
| | 8 | 23 |
| | 24 | 7 |

Thus, in an animal model with skin and subcutaneous fat similar to those of a human, a biphasic LFA concentration curve was seen in subcutaneous fat, with peak concentrations at about 8 hours after a single topical dose of latanoprost. Thus, most of the latanoprost to be delivered over a 24-hour period is delivered in the first 8 hours.

Example 2

Skin permeation studies were conducted with compositions of latanoprost, ex vivo, on fresh human skin. Skin was obtained from live donors undergoing abdominoplasty and mounted on a standard (Franz-type) diffusion cell apparatus. All test articles contained 0.8% latanoprost (by weight) and were applied uniformly to a skin surface of 0.8 cm$^2$. Each study was replicated on skin from at least two different donors. Treated skin was left open to the atmosphere to simulate clinical conditions. Receptor fluid flowed continuously over 24 hours and was collected in fractions. The amount of active drug metabolite (LFA) in these fractions was determined by Liquid Chromatography/Tandem Mass Spectrometry (LC/MS/MS). Table 2 shows the relative amounts of LFA delivered at different time intervals for each formulation, i.e. the percentage of 24-hour flux that occurred in each time interval. [Ethanol formulation 1 consisted essentially of 27% propylene glycol and 3% oleic acid in a base of about 69% ethanol.

TABLE 2

| Composition | 0-4 hours | 4-12 hours | 12-24 hours |
|---|---|---|---|
| DMSO (experiment 1) | 14% | 69% | 17% |
| DMSO (experiment 2) | 4% | 57% | 39% |
| Ethanol formulation 1 | 6% | 57% | 36% |

Thus, when DMSO- or ethanol-based compositions of latanoprost were applied to human skin in vitro, proportionately more permeation of latanoprost (and/or its active metabolite) occurred at initial application (0 hours) to about 12 hours compared to 12-24 hours after latanoprost administration. For DMSO-based formulations, about 61% to about 84% of the 24-hour flux occurred within 12 hours of application. For an ethanol-based formulation, about 63% of the 24-hour flux occurred within 12 hours of application.

Example 3

Skin permeation studies were conducted with a petroleum jelly composition of latanoprost, ex vivo, on fresh pig skin. The composition consisted essentially of 0.3% latanoprost, 5% isopropyl myristate, and 95% petroleum jelly. Skin was mounted on a standard (Franz-type) diffusion cell apparatus. All test articles were applied uniformly to a skin surface of 0.8 cm$^2$. Each study was replicated on skin from at least two different donors. Treated skin was left open to the atmosphere to simulate clinical conditions. After 1, 2, 4 or 8 hours, the test articles were removed by wiping with a swab soaked in a soap-and-water solution, followed by wiping with a dry swab. After 24 hours, samples were removed from the diffusion cells, and the dermis was isolated. The amount of active drug metabolite (LFA) in each dermis samples was determined by Liquid Chromatography/Tandem Mass Spectrometry (LC/MS/MS). Table 3 shows the results of this experiment.

TABLE 3

| Time product removed (h) | Total drug (latanoprost plus LFA) (ng) in dermis | % maximal load |
|---|---|---|
| 1 | 125 | 35% |
| 2 | 253 | 71% |
| 4 | 357 | 100% |
| 8 | 344 | 96% |

Thus, when a petroleum jelly-based composition of latanoprost was applied to skin in vitro, the dermis became fully loaded with drug (latanoprost or LFA) within 4 hours of skin contact.

Example 4

A randomized, placebo-controlled trial of topical latanoprost was conducted on male and female minipigs. Animals were randomized to no treatment, placebo (vehicle only), latanoprost 0.16%, or latanoprost 0.8% in an emulsion consisting essentially of water, poloxamer, lecithin, and isopropyl palmitate. The treatment was applied once daily to a 400 cm$^2$ area on the dorsum, with a semi-occlusive dressing. Treatment continued for 42 days.

Animals received a full panel of local and systemic safety assessments over the course of the study. Plasma toxicokinetics (TK) were assessed at various timepoints. After 42 days of treatment, animals were sacrificed. Samples of skin and subcutaneous fat were dissected from the treatment area in a controlled fashion and submitted for microscopic examination by a veterinary pathologist who was not informed of the compound tested or its therapeutic purpose.

At steady state, TK showed a peak LFA plasma concentration at about 2 to 3 hours after latanoprost application. There was evidence of accumulation of latanoprost and/or LFA in subcutaneous fat, with a plasma exposure accumulation ratio (steady state vs. first dose) of about 5 to 6 at the 0.8% dose. Such accumulation does not occur in plasma (half-life in humans is about 17 minutes) and can only be explained by redistribution from another tissue compartment. The methods of Example 1 were used to verify that substantial levels of LFA had in fact remained in subcutaneous fat after the 24-hours dose interval. The result was a mean concentration of 9600 nM at the 0.8% dose.

Dose-dependent depletion of subcutaneous fat was noted on microscopic examination of treated subcutaneous fat. Reduction of subcutaneous fat thickness was quantified using ImageJ software. In the high-dose group the mean reduction was 2.2 cubic centimeters of fat per 100 cm$^2$ of treated skin.

Thus, in a controlled trial of daily topical latanoprost in minipigs, there was evidence of peak latanoprost/LFA penetration at about 2-3 hours, accumulation and persistence of LFA in subcutaneous fat beyond 24 hours, and dose-dependent reduction of subcutaneous fat.

Example 5

A pharmacokinetic (PK) experiment was conducted on male and female minipigs (n=6 per sex). Ointment comprising latanoprost 0.5% w/w in a vehicle comprising petroleum jelly and isopropyl myristate was applied once daily for 91 days to skin over 10% of body surface area. After the last topical application, plasma PK was assessed by sampling all animals through 24 hours, and in 2 animals per sex over for an additional 48 hours. Table 4 shows the results.

TABLE 4

| Time after last dose (h) | Mean LFA concentration (pg/mL) |
|---|---|
| 0 | 1260 |
| 24 | 932 |
| 48 | 255 |
| 72 | 186 |

The results at 24, 48, and 72 hours, which correspond to the elmination (beta) phase of the time-concentration curve, were fit to a first-order kinetic model, which indicated a surprisingly long terminal elimination half-life of about 18-24 hours. This result can be attributed to redistribution from subcutaneous fat and/or dermis. The result is in contrast to a half-life of about 9-17 minutes or about 17-85 minutes, respectively, for LFA after intravenous or ocular administration. (See Sjoquist B et al., The pharmacokinetics of a new antiglaucoma drug, latanoprost, in the rabbit, Drug Metabol Distribution 1998; 26:745-754; and Sjoquist B and Stjernschantz J, Ocular and systemic pharmacokinetics of latanoprost in humans, Surv Ophthalmol 2002; 47:S6-S12).

Example 6

A randomized, double-blind, placebo-controlled trial of topical latanoprost applied to the submental area was conducted with adult men and women with excess submental fat. In one cohort, participants were randomized to receive latanoprost in an ethanol-based composition, or a matching placebo composition. In another cohort, participants were randomized to receive latanoprost in a petroleum jelly-based composition, or a matching placebo composition. The composition was applied at bedtime to a controlled 50 cm² area of submental skin. Participants were instructed to wash the 50 cm² area after 8-10 hours, so as to remove the composition. Treatment continued for 42 days. Topical latanoprost was well tolerated.

Example 7

A kit is provided comprising a tube of a topical composition comprising a PFPRA compound, e.g., latanoprost, tafluprost, travoprost, or bimatoprost, for reducing subcutaneous fat, and instructions for use. The instructions for use comprise instructions to apply the composition in a thin film to a particular area of the body once nightly, e.g., at bedtime, and to remove the gel, e.g., by washing with soap and water, 6 to 10 hours after application.

Example 8

A randomized, double-masked, placebo-controlled trial of latanoprost ointment applied to lower eyelids was conducted with adult men and women with lower lid steatoblepharon, i.e., eye bags. Participants received a kit comprising a tube of latanoprost ointment and instructions to apply the topical composition to the lower eyelids once nightly at bedtime. Participants were instructed to wash the lower eyelids 8-10 hours after ointment application, so as to remove the ointment or residue thereof. Treatment continued for 10 weeks. Latanoprost ointment was associated with statistically significant improvements in patient- and clinician reported measures of eyelid fat volume, patient appearance, and patient satisfaction over the course of the study. The topical latanoprost composition was well tolerated.

Example 9

A topical composition comprising a compound of the formula:

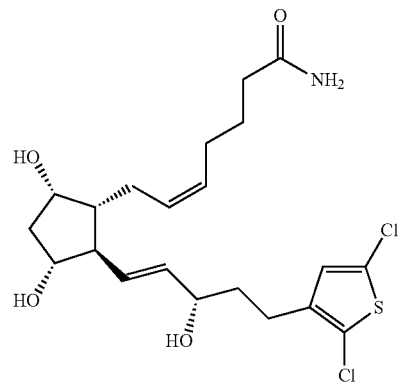 [SMILES: NC(=O)CCC/C=C\C[C@@H]1[C@@H](/C=C/[C@@H](O)CCc2cc(Cl)sc2Cl)[C@H](O)C[C@@H]1O]

(at a concentration between about 0.03% and about 3% w/w) and one or more pharmaceutically acceptable excipients (e.g., water, ethanol, propylene glycol, petrolatum, mineral oil, white wax, isopropyl myristate, and/or diethylene glycol monoethyl ether), is administered once daily to an area of skin (e.g., eyelid, face and/or submental region) on a patient for a period between about 1 to 6 months. After each administration the composition is removed after about 6 to 12 hours. It is contemplated that after 1 to 6 months of repeated administration, subcutaneous fat will be reduced at the site of administration.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for locally reducing body fat in a subject in need thereof, the method comprising the steps of: administering a composition comprising latanoprost to the skin surface; and removing the composition or residue thereof from the skin surface between about 4 hours and about 12 hours, inclusive, after said administering;
   wherein more than about 60 percent of the 24-hour flux of latanoprost or an active metabolite thereof occurs within 4 to 12 hours, inclusive, after the step of administering, and wherein the step of removing is after more than about 60 percent of the 24-hour flux has occurred.

2. The method of claim 1, wherein the removing is between about 4 hours and about 10 hours, inclusive, after said administering.

3. The method of claim 2, wherein the removing is between about 4 hours and about 8 hours, inclusive, after said administering.

4. The method of claim 2, wherein the removing is between about 6 hours and about 10 hours, inclusive, after said administering.

5. A method for locally reducing body fat in a subject in need thereof, the method comprising the steps of: administering a composition comprising latanoprost to the skin surface; and removing the composition or residue thereof from the skin surface between about 4 hours and about 12 hours, inclusive, after said administering; wherein the dermis is fully loaded with latanoprost, an active metabolite thereof, or a combination thereof, within 4 to 12 hours, inclusive, after the administering, and wherein the step of removing is after the dermis is fully loaded.

6. The method of claim 1, wherein the dose frequency is once every 24 hours.

7. The method of claim 1, wherein the body fat is eyelid fat.

8. The method of claim 1, wherein the composition is an ointment.

9. The method of claim 1, wherein the composition comprises petroleum jelly.

10. The method of claim 9, wherein the composition further comprises isopropyl myristate.

11. The method of claim 1, wherein the composition comprises isopropyl myristate.

12. The method of claim 5, wherein the removing is between about 4 hours and about 10 hours, inclusive, after said administering.

13. The method of claim 12, wherein the removing is between about 4 hours and about 8 hours, inclusive, after said administering.

14. The method of claim 12, wherein the removing is between about 6 hours and about 10 hours, inclusive, after said administering.

15. The method of claim 5, wherein the dose frequency is once every 24 hours.

16. The method of claim 5, wherein the body fat is eyelid fat.

17. The method of claim 5, wherein the composition is an ointment.

18. The method of claim 5, wherein the composition comprises petroleum jelly.

19. The method of claim 18, wherein the composition further comprises isopropyl myristate.

20. The method of claim 5, wherein the composition comprises isopropyl myristate.

* * * * *